(12) United States Patent
Scianamblo

(10) Patent No.: US 8,932,056 B2
(45) Date of Patent: *Jan. 13, 2015

(54) SWAGGERING ENDODONTIC INSTRUMENTS

(71) Applicant: Michael Scianamblo, Tiburon, CA (US)

(72) Inventor: Michael Scianamblo, Tiburon, CA (US)

(*) Notice: Subject to any disclaimer, the term of this patent is extended or adjusted under 35 U.S.C. 154(b) by 12 days.

This patent is subject to a terminal disclaimer.

(21) Appl. No.: 13/794,629

(22) Filed: Mar. 11, 2013

(65) Prior Publication Data

US 2013/0302749 A1  Nov. 14, 2013

Related U.S. Application Data

(63) Continuation of application No. 11/402,207, filed on Apr. 10, 2006, now Pat. No. 8,454,361.

(60) Provisional application No. 60/669,409, filed on Apr. 8, 2005.

(51) Int. Cl.
*A61C 5/02* (2006.01)

(52) U.S. Cl.
CPC ..................... *A61C 5/023* (2013.01)
USPC ........................................ 433/102

(58) Field of Classification Search
USPC ............................. 433/102, 81, 224, 165–166
See application file for complete search history.

(56) References Cited

U.S. PATENT DOCUMENTS

| | | |
|---|---|---|
| 4,044,468 A * | 8/1977 | Kahn ............................ 433/102 |
| 4,353,698 A | 10/1982 | McSpadden |
| 4,457,710 A | 7/1984 | McSpadden |
| 4,536,159 A | 8/1985 | Roane |
| 4,538,989 A | 9/1985 | Apairo, Jr. et al. |
| 4,889,487 A * | 12/1989 | Lovaas ......................... 433/102 |
| 4,934,934 A | 6/1990 | Arpaio, Jr. et al. |
| 4,992,048 A | 2/1991 | Goof |
| 5,503,554 A | 4/1996 | Schoeffel |
| 5,605,460 A | 2/1997 | Heath et al. |
| 5,676,541 A | 10/1997 | Maillefer et al. |
| 5,775,904 A | 7/1998 | Riitano |
| 5,836,764 A | 11/1998 | Buchanan |
| 5,842,862 A | 12/1998 | Nissan |
| 5,882,198 A * | 3/1999 | Taylor et al. .................. 433/102 |
| 5,897,316 A | 4/1999 | Buchanan |
| 5,902,106 A | 5/1999 | McSpadden |
| 5,921,775 A | 7/1999 | Buchanan |
| 5,938,440 A | 8/1999 | McSpadden |

(Continued)

FOREIGN PATENT DOCUMENTS

| | | |
|---|---|---|
| EP | 0 120 542 | 10/1984 |
| FR | 2 798 277 | 3/2001 |
| WO | WO02/065938 | 8/2002 |
| WO | WO 2004/098438 | 11/2004 |

OTHER PUBLICATIONS spiral. (n. d.). Dictionary.com Unabridged. Retrieved Feb. 4, 2014, from Dictionary.com website: http://dictionary.reference.com/browse/spiral.*

(Continued)

*Primary Examiner* — Heidi M Eide
(74) *Attorney, Agent, or Firm* — Fish & Richardson P.C.

(57) ABSTRACT

Endodontic instruments are described which have at least a section with a center of mass offset from an axis of rotation so that when the instrument is rotated, the section bends away from the axis of rotation.

20 Claims, 33 Drawing Sheets

(56) References Cited

U.S. PATENT DOCUMENTS

| | | | |
|---|---|---|---|
| 6,106,296 | A | 8/2000 | Johnson |
| 6,299,445 | B1 | 10/2001 | Garman |
| 6,315,558 | B1 | 11/2001 | Farzin-Nia et al. |
| 6,419,488 | B1 | 7/2002 | McSpadden et al. |
| 6,575,748 | B1 * | 6/2003 | Filhol ............... 433/102 |
| 6,702,579 | B1 * | 3/2004 | Hoppe et al. ............ 433/102 |
| 6,890,134 | B1 | 5/2005 | Wagner et al. |
| 6,929,078 | B1 | 8/2005 | Randall |
| 6,942,484 | B2 | 9/2005 | Scianamblo |
| 7,094,056 | B2 | 8/2006 | Scianamblo |
| 7,955,078 | B2 | 6/2011 | Scianamblo |
| 2004/0023186 | A1 | 2/2004 | McSpadden |
| 2004/0131993 | A1 | 7/2004 | Rouiller et al. |
| 2004/0185414 | A1 | 9/2004 | Badoz |
| 2005/0026109 | A1 * | 2/2005 | Buchanan ............... 433/102 |
| 2005/0266375 | A1 | 12/2005 | Brock et al. |
| 2006/0216668 | A1 | 9/2006 | Scianamblo |
| 2006/0228668 | A1 | 10/2006 | McSpadden |
| 2006/0228669 | A1 | 10/2006 | Scianamblo |
| 2007/0059663 | A1 | 3/2007 | Scianamblo |
| 2007/0184406 | A1 | 8/2007 | Mason |
| 2011/0217673 | A1 | 9/2011 | Scianamblo |
| 2013/0273497 | A1 | 10/2013 | Scianamblo |

OTHER PUBLICATIONS

Partial European Search Report, European Application Serial No. EP 06 00 7527, Jun. 26, 2006, 6 pages.

EP 04 75 1290 Supplementary European Search Report, Jun. 5, 2007, 5 pages.

EP 04 75 0878 Supplementary European Search Report, Jun. 5, 2007, 3 pages.

Communication pursuant to Article 94(3) EPC for Application No. EP 06 00 7527.2-1265, dated Jun. 17, 2009, 5 pages.

Linear definition from Merriam-Webster on-line. Retrieved on Feb. 20, 2009, from http://.www.merriam-webster.com/dictionary/linear, 3 pages.

Straight. (n. d.). Dictionary.com Unabridged. Retrieved Feb. 11, 2010, from Dictionary.com website: http://dictionary.reference.com/browse/straight, 12 pages.

USPTO Non-Final Office Action in U.S. Appl. No. 11/402,207, mailed Feb. 26, 2009, 16 pages.

USPTO Final Office Action in U.S. Appl. No. 11/402,207, mailed Oct. 6, 2009, 9 pages.

USPTO Non-Final Office Action in U.S. Appl. No. 11/402,207, mailed Feb. 19, 2010, 10 pages.

USPTO Non-Final Office Action in U.S. Appl. No. 11/226,059, mailed Mar. 31, 2008, 5 pages.

USPTO Final Office Action in U.S. Appl. No. 11/226,059, mailed May 13, 2009, 8 pages.

USPTO Non-Final Office Action in U.S. Appl. No. 11/226,059, mailed Oct. 21, 2009, 9 pages.

USPTO Final Office Action in U.S. Appl. No. 11/226,059, mailed May 17, 2010, 9 pages.

Office Action in U.S. Appl. No. 11/402,207, mailed Aug. 25, 2010, 13 pages.

USPTO Non-Final Office Action in U.S. Appl. No. 11/402,207, mailed Aug. 28, 2012, 7 pages.

* cited by examiner

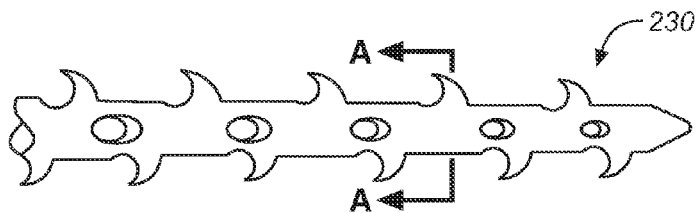 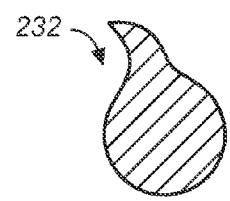
FIG. 2C
(PRIOR ART)
FIG. 2D
(PRIOR ART)
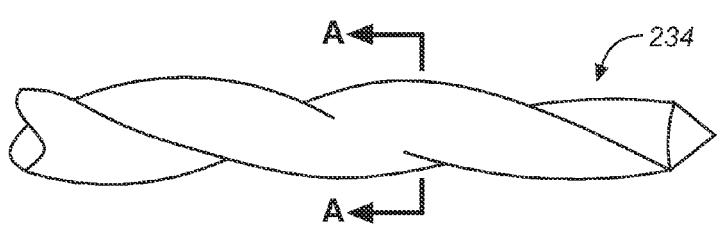 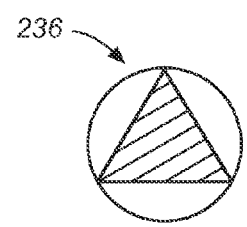
FIG. 2E
(PRIOR ART)
FIG. 2F
(PRIOR ART)
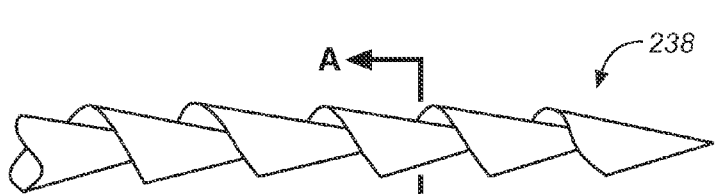 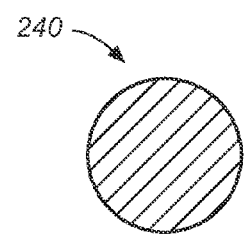
FIG. 2G
(PRIOR ART)
FIG. 2H
(PRIOR ART)
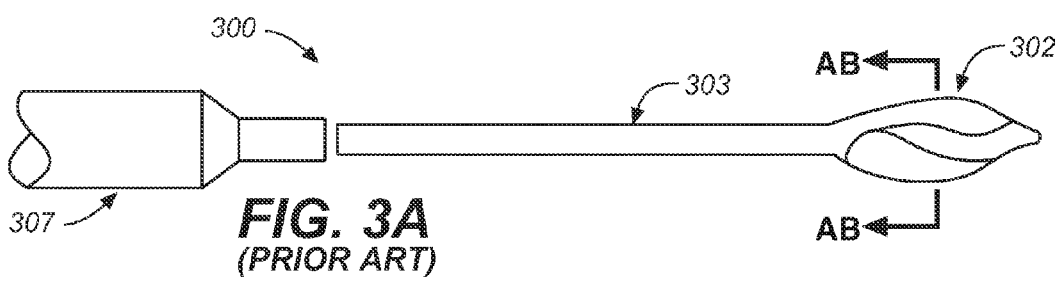
FIG. 3A
(PRIOR ART)
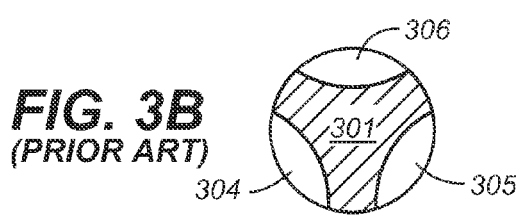
FIG. 3B
(PRIOR ART)

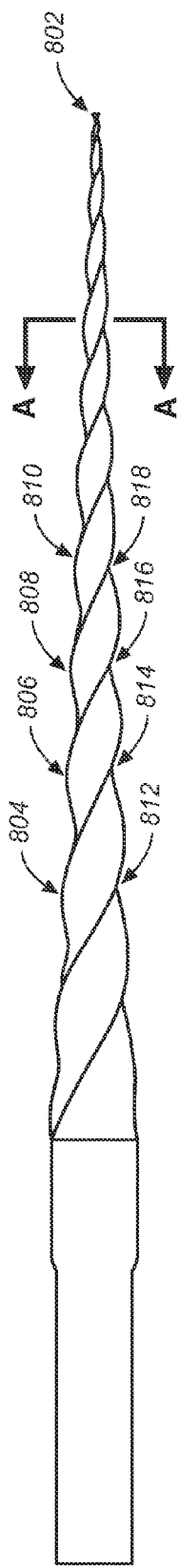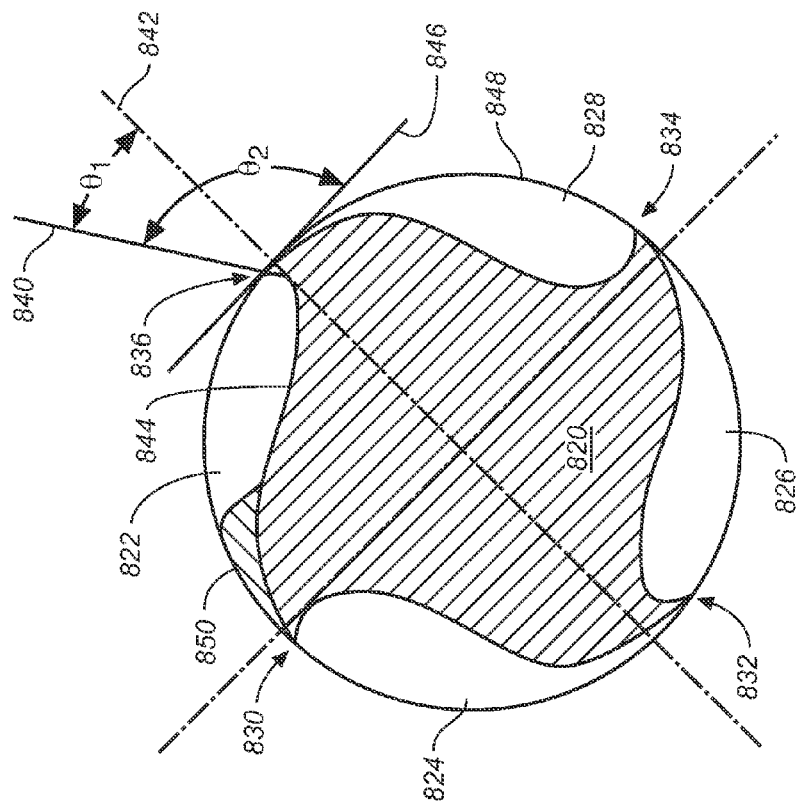
FIG. 8A
FIG. 8B

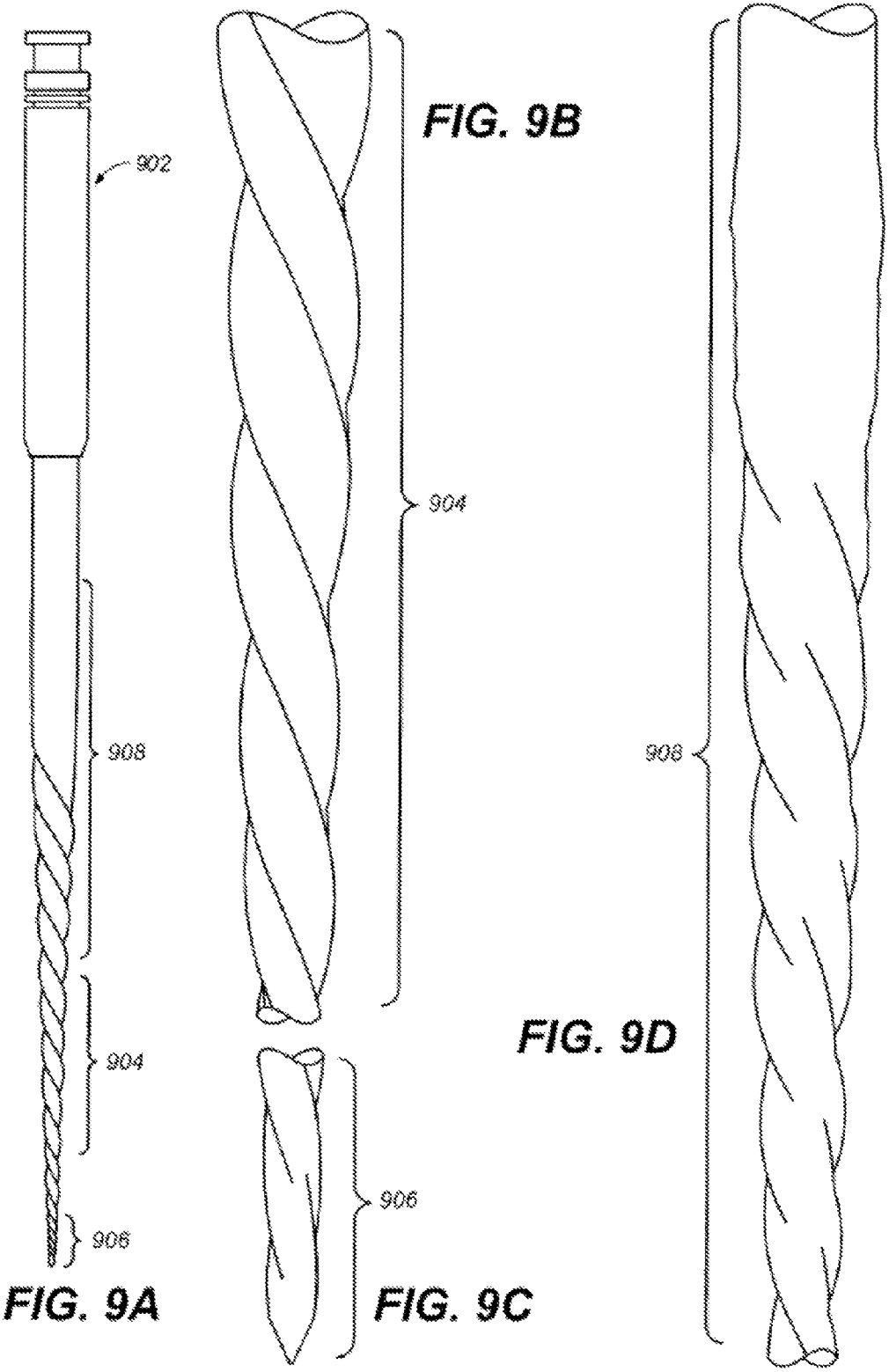

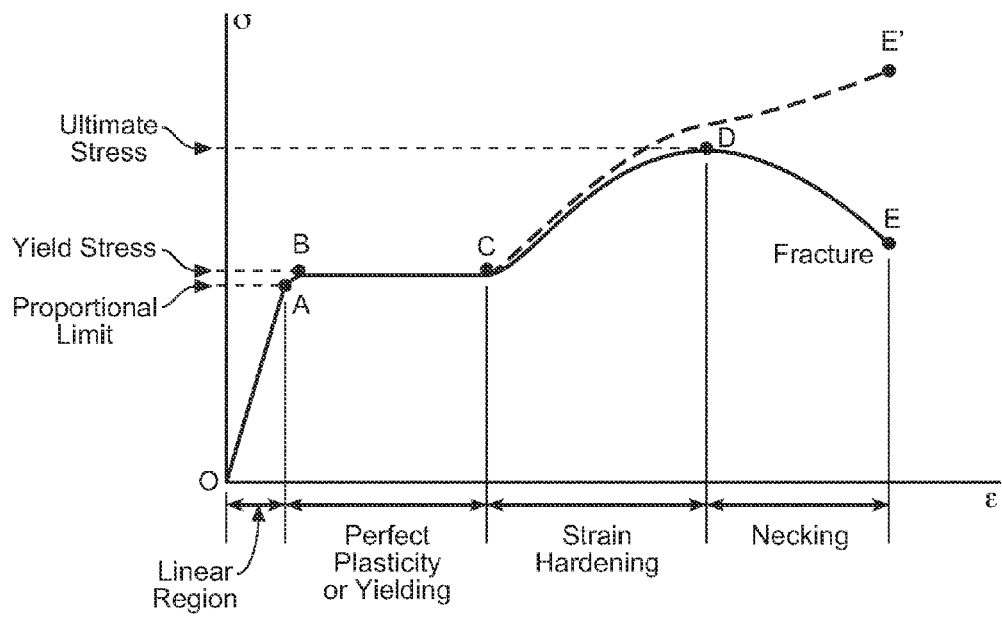
FIG. 17
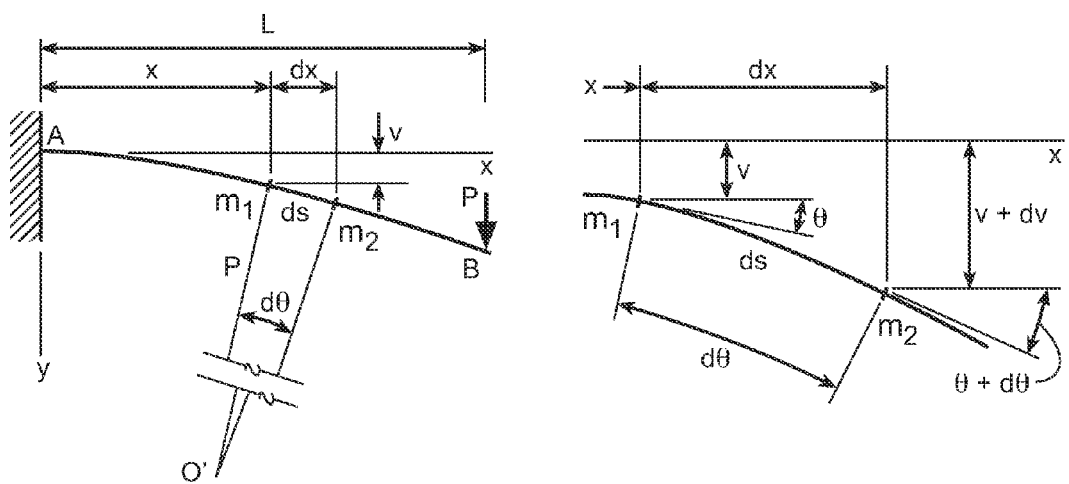
FIG. 18A  FIG. 18B

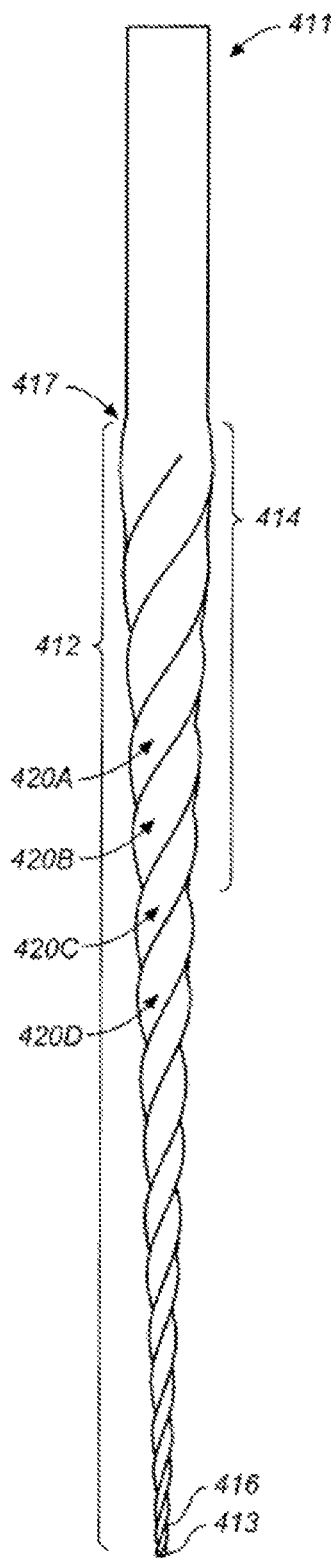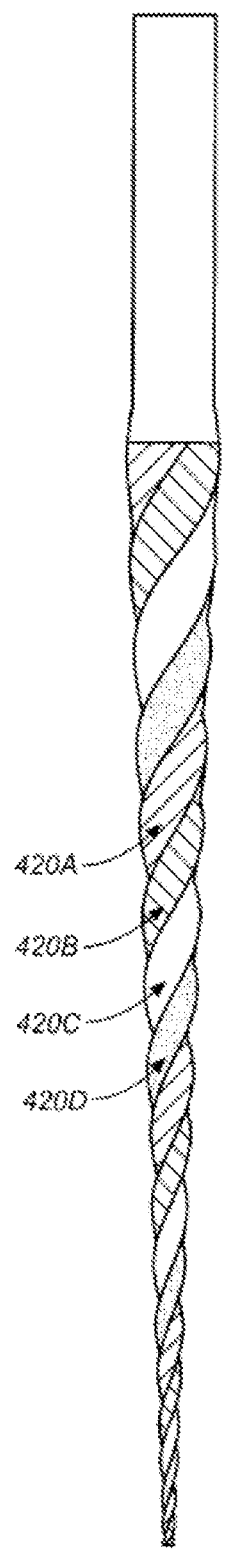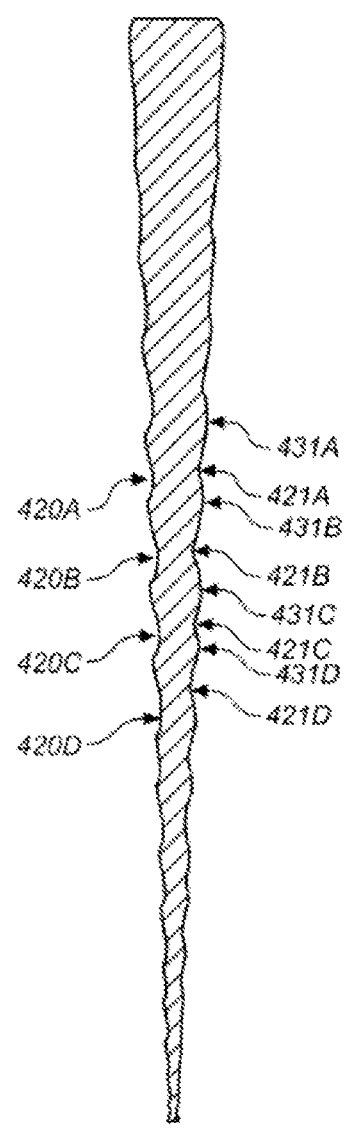
*FIG. 25A*  *FIG. 25B*  *FIG. 25C*

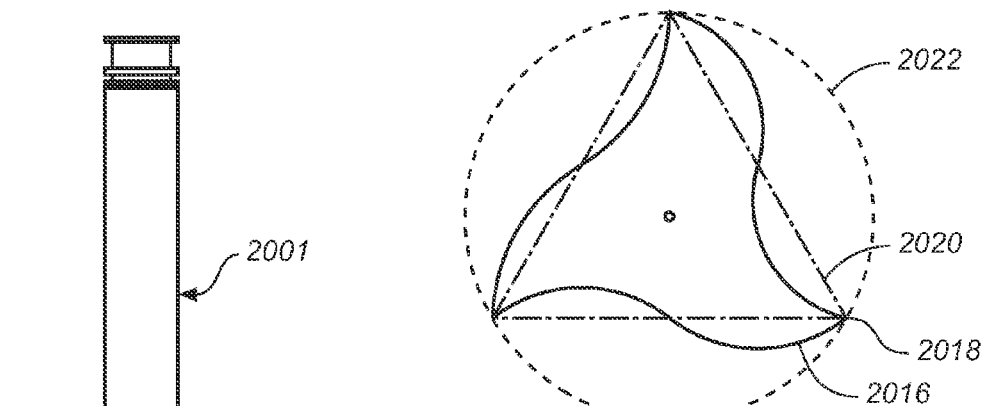
FIG. 27A
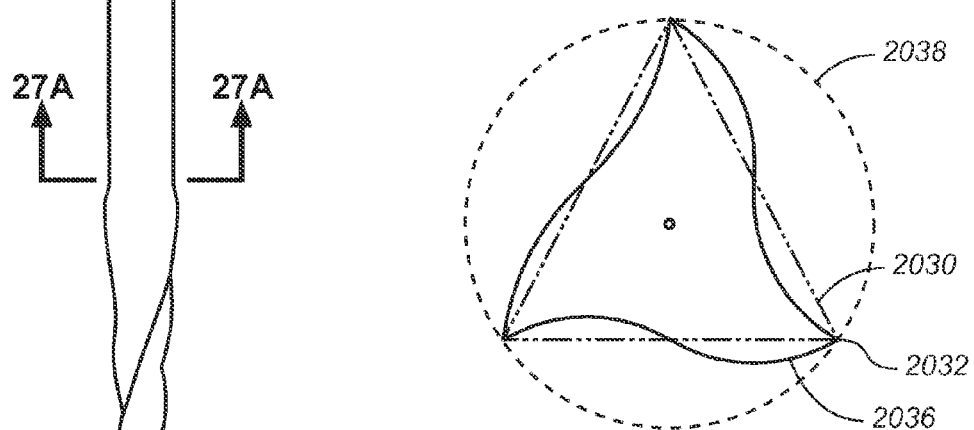
FIG. 27B
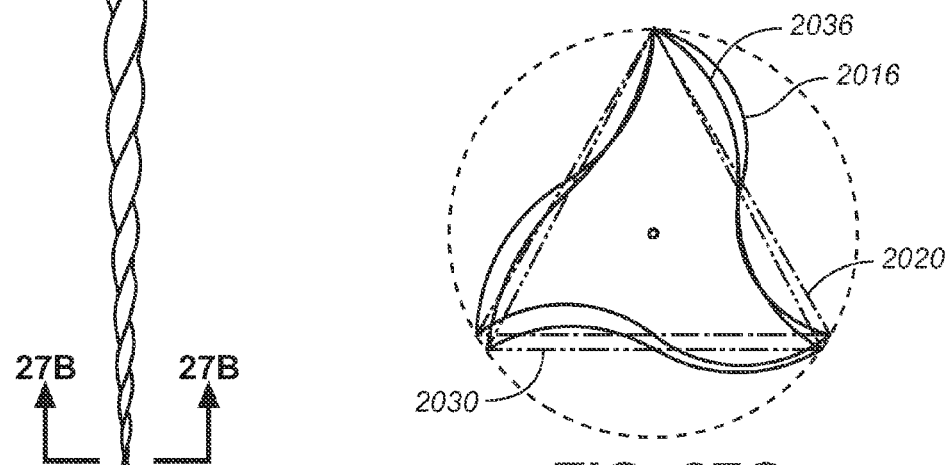
FIG. 27C
FIG. 27

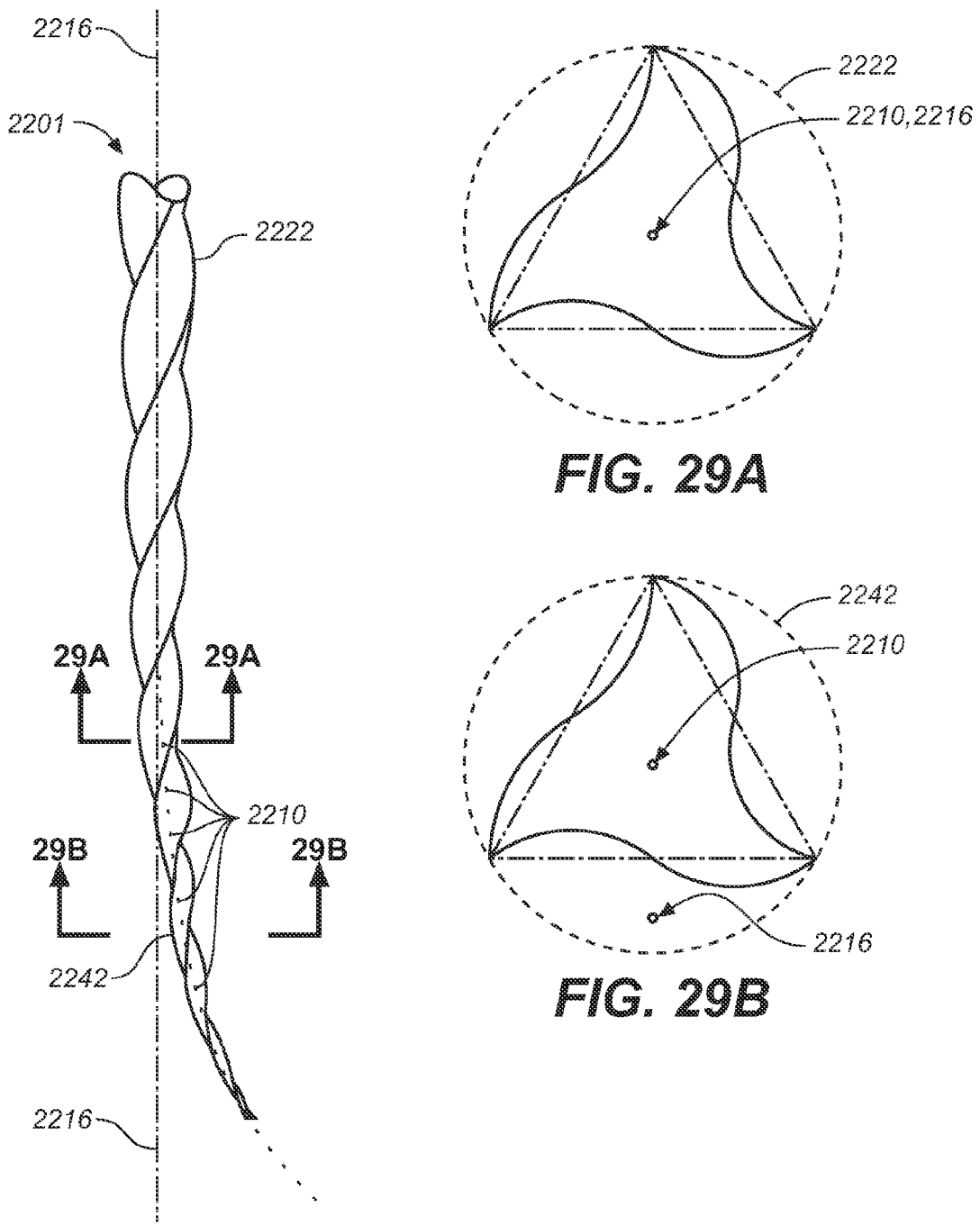

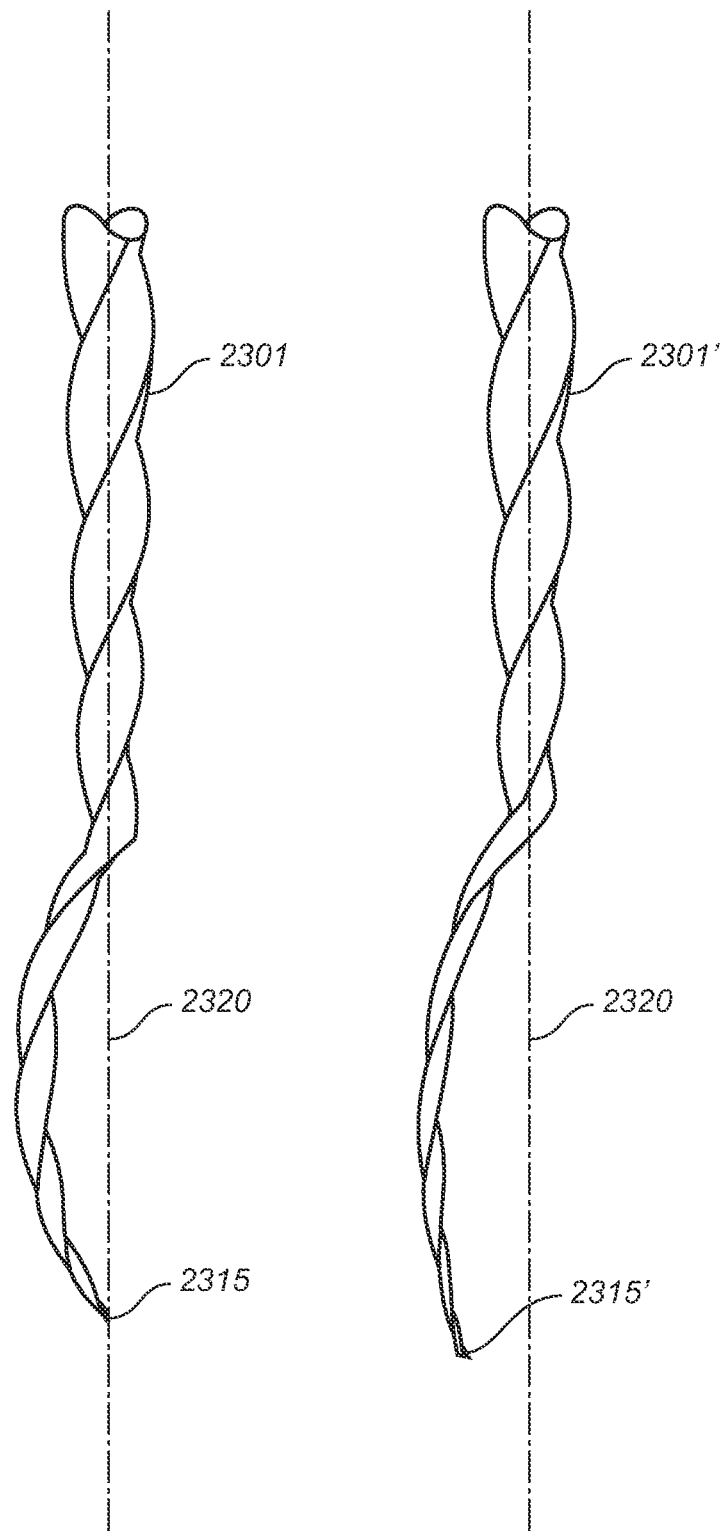
FIG. 30A   FIG. 30B

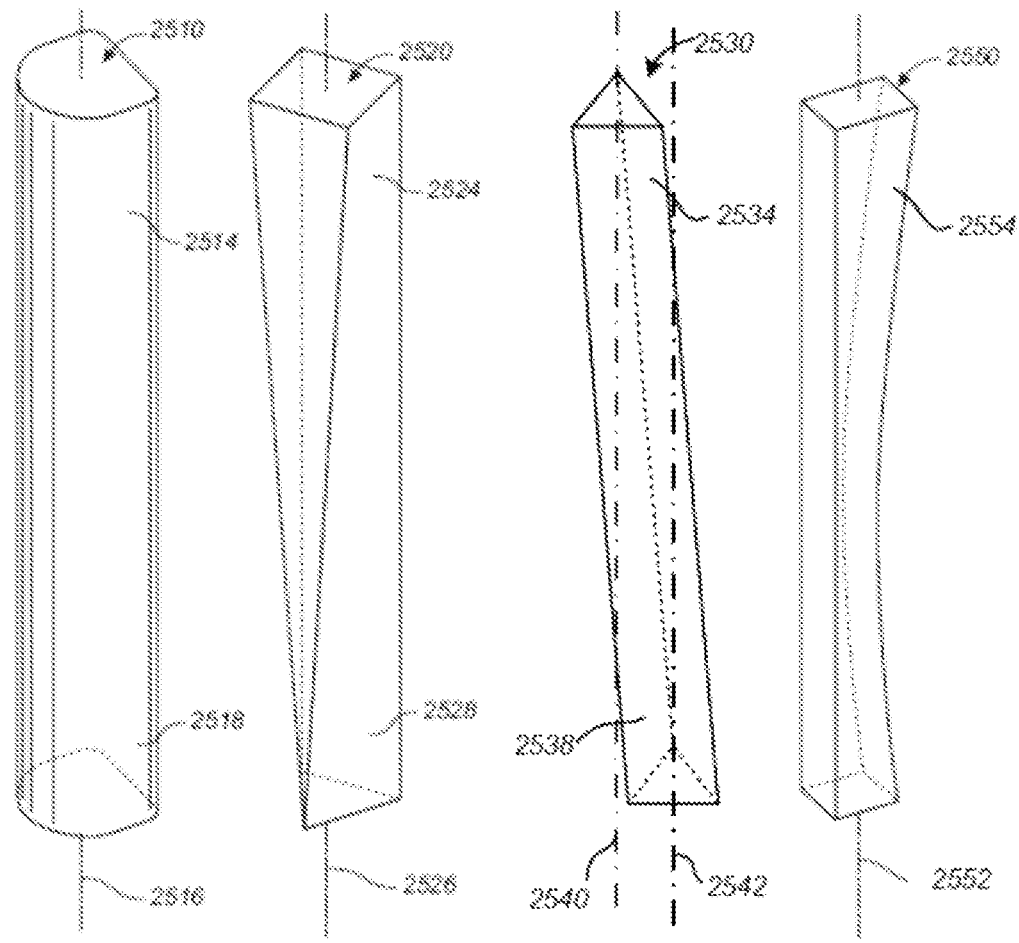
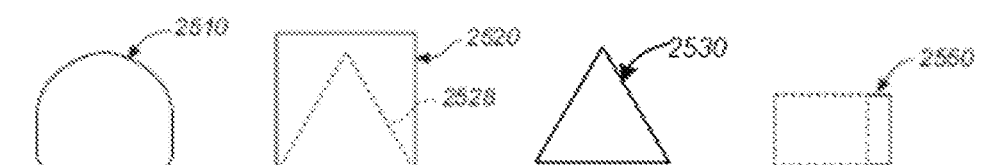
FIG. 32A  FIG. 33A  FIG. 34A  FIG. 35A
FIG. 32B  FIG. 33B  FIG. 34B  FIG. 35B

SWAGGERING ENDODONTIC INSTRUMENTS

CROSS-REFERENCE TO RELATED APPLICATIONS

This application is a continuation of U.S. application Ser. No. 11/402,207, filed Apr. 10, 2006, which claims priority to U.S. Provisional Application Ser. No. 60/669,409, filed Apr. 8, 2005. The disclosure of the prior applications is considered part of and is incorporated by reference in the disclosure of this application.

BACKGROUND

The present invention relates to endodontic instruments.

Endodontic instruments can be used for cleaning and enlarging the endodontic cavity space ("ECS"), also known as the root canal system of a human tooth. FIG. 1A shows an example of an unprepared root canal 102 of a tooth 104. As can be seen, the unprepared root canal 102 is usually a narrow channel that runs through the central portion of the root of the tooth. Cleaning and enlargement of the ECS can be necessitated by the death or necrosis of the dental pulp, which is the tissue that occupies that space in a healthy tooth. This tissue can degenerate for a multitude of reasons, which include tooth decay, deep dental restorations, complete and incomplete dental fractures, traumatic injuries or spontaneous necrosis due to the calcification and ischemia of the tissue, which usually accompanies the ageing process. Similar to a necrotic or gangrenous appendix, the complete removal of this tissue is paramount, if not urgent, because of the subsequent development of infections or dental abscesses, septicemia, and even death.

The root canal system of a human tooth is often narrow, curved and calcified, and can be extremely difficult to negotiate or clean. Indeed, the conventional endodontic or root canal instruments currently available are frequently inadequate in the complete removal of the pulp and the efficient enlargement of the ECS. Furthermore, they are usually predisposed to breakage, causing further destruction to the tooth. Broken instruments are usually difficult, if not impossible to remove, often necessitating the removal of the tooth. Injury to the tooth, which occurs as the result of a frank perforation or alteration of the natural anatomy of the ECS, can also lead to failure of the root canal and tooth loss.

A root canal procedure itself can be better appreciated by referring to FIGS. 1A and 1B. The unprepared root canal 102 of the tooth 104 usually begins as a narrow and relatively parallel channel. The portal of entry or the orifice 106 and the portal of exit or foramen 108 are relatively equal in diameter. To accommodate complete cleaning and filling of the canal and to prevent further infection, the canal must usually be prepared. The endodontic cavity preparation ("ECP") generally includes progressively enlarging the orifice and the body of the canal, while leaving the foramen relatively small. The result is usually a continuous cone shaped preparation, for example, the space 109.

In general, endodontic instruments are used to prepare the endodontic cavity space as described above. Endodontic instruments can include hand instruments and engine driven instruments. The latter can but need not be a rotary instrument. Combinations of both conventional hand and engine driven rotary instruments are usually required to perform an ECP successfully and safely.

FIGS. 2A and 2B show a conventional endodontic instrument 200. The endodontic instrument shown includes a shaft 202 that includes a tip 204 and a shank 206. The endodontic instrument 200 also includes grooves 208 and 210 that spiral around the shaft 202. The grooves are referred to in the instant specification as flutes.

FIG. 2B shows a cross section 212 (i.e., cross section A-A) of the endodontic instrument. The cross section 208 shows cross sections 214 and 216 of flutes 208 and 210, respectively. As can be seen from FIGS. 2A and 2B, the flutes 208 and 210 are generally the spacing on both sides of a helical structure 218 (or helix) that spirals around the shaft 202. The bottom portion of a flute—seen as a line or curve (e.g., curve 220 indicated in bold)—is referred to in the instant specification as a spline (indicated by line in bold). The portion of a spline that comes into contact with a surface being cut during cutting will be referred to in the instant specification as a radial land. Item 222 of FIG. 2B is an example of a radial land.

A flute of an endodontic instrument usually includes a sharpened edge configured for cutting. Edge 224 of FIG. 2A is an example of such a cutting edge. Edge 224 can be seen as a point 226 in FIG. 2B. Generally, an instrument having right handed cutting edges is one that will cut or remove material when rotated clockwise, as viewed from shank to tip. In this specification, a direction of rotation will be specified as viewed from the shank to the tip of the instrument. The cut direction of rotation for a right handed endodontic instrument is clockwise. An instrument having left handed cutting edges is one that will cut or remove material when rotated counter clockwise. The cut direction of rotation, in this case, is counter clockwise.

An endodontic instrument includes a working portion, which is the portion that can cut or remove material. The working portion is typically the portion along the shaft that is between the tip of the instrument and the shank end of the flutes. Portion 228 is the working portion for the endodontic instrument shown in FIG. 2A. The working portion is also referred to in this specification as the cutting portion, and the working length as the cutting or working length.

Hand instruments are typically manufactured from metal wire blanks of varying sizes. The metallurgical properties of these wires, in general, have been engineered to produce a wide range of physical properties. These wires are usually then twisted or cut to produce specific shapes and styles. Examples of hand instruments include K-type, H-type, and R-type hand instruments. FIG. 2C show a barbed broach 230, which is one example of an R type instrument. FIG. 2D shows a cross section 232 (i.e., cross section A-A) of the barbed broach 230. The barbed broach is manufactured from soft iron wire that is tapered and notched to form barbs or rasps along its surface. These instruments are generally used in the gross removal of pulp tissue or debris from the root canal system. Another R-type file is a rat-tail file.

K-type instruments in current usage include reamers and K-files. FIG. 2E shows an example of a K file 234. FIG. 2F shows a cross section 236 (i.e., cross section A-A) of the K file 234. K files are generally available in carbon steel, stainless steel, and more recently, an alloy of nickel-titanium. To fabricate a K type instrument, a round wire of varying diameters is usually grounded into three or four-sided pyramidal blanks and then rotated or twisted into the appropriate shapes. These shapes are specified and controlled by the American National Standards Institute ("ANSI") and the International Standards Organization ("ISO"). The manufacturing processes for reamers and files are similar; except however, files usually have a greater number of flutes per unit length than reamers. Reamers are used in a rotational direction only, whereas files can be used in a rotational or push-pull fashion. Files made from three-sided or triangular blanks have smaller cross sectional areas than files made from four sided blanks. Thus, these instruments are usually more flexible and less likely to fracture. They also can display larger clearance angles and are more efficient during debridement. Triangular files, therefore, are generally considered more desirable for hand instrumentation.

FIG. 2G shows an example of an H-type file 238. FIG. 2H shows a cross section 240 (i.e., cross section A-A) of the H type file 238. H type files are usually manufactured by grinding flutes into tapered round metal blanks to form a series of intersecting cones. H type files can usually cut only in the pull direction (i.e., a pull stroke). Primarily because they have positive rake angles, H type files can be extremely efficient cutting instruments.

Hand instruments are usually manufactured according to guidelines of the ANSI and the ISO, which specified that a working portion of an instrument be 16 mm in length. ANSI and ISO further specified that a first diameter or D1 of the instrument, be 1 mm from the tip or $D_0$. Other ANSI and ISO specifications require that: instruments have a standard taper of 0.02 mm per mm along the working portion 216; the tip maintain a pyramidal shape no greater than 75° in linear cross section; and hand instruments (e.g., the ones shown in FIGS. 2A 2H) be available in 21, 25, and 31 mm lengths.

In addition to the hand instruments described above, there are rotary instruments that are usually motor driven. FIG. 3A shows an example rotary instrument 300 that is referred to as a G type reamer or drill. FIG. 3B shows a cross section 301 (i.e., cross section A-A) of the G type instrument. G-type drills are usually available in carbon or stainless steel. As is typical, the G type drill 300 shown includes a short flame-shaped head 302 attached to a long shank 303. The core or web shown in FIG. 3B shows the cross sections 304, 305, and 306 of three flutes. The flutes, in this instance, have U shaped splines. The instrument 300 includes cutting edges that have negative rake-angles. In general, a rake angle is the angle between the leading edge of a cutting tool and a perpendicular to the surface being cut. Rake angle is further described below. The flame shaped head 302 includes a non cutting surface to prevent perforation. The instrument 300 is usually used as a side cutting instrument only. The instrument 300 is relatively rigid and, therefore, cannot usually be used in a curved space, for example, the ECS.

G-type drills are available in 14, 18 and 25 mm lengths as measured from tip to shank, which is where the drill can be inserted into a standard slow-speed hand piece via a latch grip 307. G type drills are available in varying diameters of 0.30 mm to 1.5 mm and from sizes 1 through 6.

SUMMARY

The present invention provides methods and apparatus for providing swaggering endodontic instruments for preparing an endodontic cavity space.

In one aspect, the invention is directed to an endodontic device having a tapered body having a tip end and a shank end, wherein the tip end has a diameter that is less than a diameter of the shank end and the body has an axis of rotation extending from the tip end to the shank end. The body has at least one working surface extending between the shank end and the tip end; a first cross section perpendicular to the axis of rotation, wherein the first cross section has a first geometry; and a second cross section perpendicular to the axis of rotation, and wherein the second cross section has a second geometry, wherein the first geometry is different from the second geometry; wherein the first cross section and the second cross section intersect the at least one working surface.

Implementations may include one or more of the following features. The first geometry can be symmetrical and the second geometry can be asymmetrical. The first cross section can be closer to the shank end than the tip end. The first cross section can have a different number of working surfaces than the second cross section. At the second cross section, a centroid can be offset from the axis of rotation. The first geometry and the second geometry can include different numbers of working surfaces. The body can be flexible. The body can be formed of nickel-titanium. The body can be sufficiently flexible such that when a tip of the body is bound at a fixed position as the body rotates, a portion of the body that intersects the second cross section bends away from the axis of rotation a substantially equal amount at a first angle of rotation and at a second angle of rotation. The first angle of rotation can be 180° from the second angle of rotation. The second cross section can bend away from the axis of rotation a substantially equally amount at each angle of rotation. A non-swaggering portion of the body can have a centroid that lies substantially on the axis of rotation and intersects the at least one working surface as the tip of the body is bound at a fixed position and the body rotates. The at least one working surface can include a cutting flute. A tip of the body may not have cutting surfaces. At a cross section that intersects the axis of rotation, a center of mass may be offset from the axis of rotation. The working surface can be configured to remove material when the body is rotated within a canal of the material. When the tip of the body is held in place and the body is rotated, at least a portion of the body may form helical waves In another aspect, the invention is directed to an endodontic device, comprising a tapered body having a tip end and a shank end, wherein the tip end has a diameter that is less than a diameter of the shank end and the body has an axis of rotation, wherein along the length of the tapered body, at least one centroid of a cross section that intersects a working surface of the body is on the axis of rotation and at least one centroid is offset from the axis of rotation, the body having at least one cutting surface along the outer diameter that is configured to remove material when the body is rotated within a canal of the material.

Implementations may include one or more of the following features. The body can be canted so that the centroid on the axis of rotation is near the shank end and a tip is furthest from the axis of rotation as compared to other centroids along the length of the body. The body cab be linear. A plurality of centroids that correspond to the cutting surface may be in a line. The body can have a portion including the cutting surface and the portion can be linear. The body can be flexible. The body can be formed of nickel-titanium. The body can be sufficiently flexible such that when a tip of the body is bound at a fixed position as the body rotates, a portion of the body can bend away from the axis of rotation a substantially equal amount at multiple angles of rotation. The body can be curved. The tip can be offset from the axis of rotation. The tip can be on the axis of rotation. The body can have at least one working surface extending between the shank end and the tip end; a first cross section perpendicular to the axis of rotation, wherein the first cross section has a first geometry; a second cross section perpendicular to the axis of rotation, wherein the second cross section has a second geometry, wherein the first geometry is different from the second geometry; and the first cross section and the second cross section intersect the at least one cutting surface. When the tip of the body is held in place and the body is rotated, at least a portion of the body can form helical waves.

In yet another aspect, the invention is directed to an endodontic device, comprising a tapered body having a tip end and a shank end, wherein the body has at least a portion with a center of mass that is offset from an axis of rotation and is sufficiently flexible such that when a tip of the body is bound at a fixed position as the body rotates, the portion bends away from the axis of rotation a substantially equal amount at a first angle of rotation and at a second angle of rotation. The first angle of rotation can be 180° from the second angle of rotation. The portion can bend away from the axis of rotation a substantially equal amount at each angle of rotation.

In another aspect, the invention is directed to endodontic device, comprising a linear body having a tip end and a shank end and a working surface between the tip end and the shank end, wherein a first cross section of the body intersects the working surface toward the shank end and a second cross section of the body intersects the working surface toward the tip end, the first cross section is parallel to the second cross section, both the first cross section and the second cross section are symmetrical and a first axis through a center of the first cross section and perpendicular to the first cross section is different from a second axis through a center of the second cross section and perpendicular to the second cross section.

Implementations may include one or more of the following features. The body can be flexible, e.g., the body can be formed of nickel-titanium. The body can be sufficiently flexible such that when a tip of the body is bound at a fixed position as the body rotates, a portion of the body bends away from the axis of rotation a substantially equal amount at multiple angles of rotation. The multiple angles of rotation can be 180° apart. The body can have the same geometry and dimensions down its length. When the tip of the body is held in place and the body is rotated, at least a portion of the body can form helical waves.

In yet other aspect, the invention is directed to a method of cleaning an endodontic cavity space. A flexible instrument is inserted into the endodontic cavity space, wherein the instrument has a first portion with a center of mass that overlaps with an axis of rotation of the instrument and at a second portion with a center of mass that is offset from the axis of rotation. A tip of the flexible instrument is contacted against an inner surface of the cavity space. The instrument is rotated so that the first portion bends away from the axis of rotation a substantially equal amount at a first angle of rotation and at a second angle of rotation. Rotating the instrument can include causing the instrument for form sinusoidal waves within the cavity space.

In yet another aspect, the invention is directed to a method of cleaning an endodontic cavity space. A flexible instrument is inserted into the endodontic cavity space, wherein the instrument has a tapered body having a tip end and a shank end, the tip end has a diameter that is less than a diameter of the shank end and the body has an axis of rotation extending from the tip end to the shank end, the body having at least one working surface extending between the shank end and the tip end, a first cross section perpendicular to the axis of rotation, wherein the first cross section has a first geometry, and a second cross section perpendicular to the axis of rotation, wherein the second cross section has a second geometry, wherein the first geometry is different from the second geometry, wherein the first cross section and the second cross section intersect the at least one working surface. A tip of the flexible instrument is contacted against an inner surface of the cavity space. The instrument is rotated so that the least one working surface intersecting the second cross section bends away from the axis of rotation a substantially equal amount at a first angle of rotation and at a second angle of rotation.

Devices described herein can provide more efficient endodontic cleaning which is safer for a patient. An instrument that is both flexible and strong resists breaking and injuring the patient. An instrument that is flexible and has a center of mass offset from an axis of rotation may swing out from the axis of rotation as the instrument is rotated at high speeds, such as when the instrument is used with a motorized tool. If the instrument is configured to bend an equal amount at each angle of rotation, the inner diameter of a space can be contacted by the instrument and uniformly cleaned. The instrument can be made to have a smaller diameter than the space that requires cleaning, thereby allowing for a difficult to access area to be accessed. The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2H show examples of endodontic instruments.
FIGS. 3A and 3B show an example of a rotary type endodontic instrument.
FIGS. 8A and 8B show an endodontic instrument having S splines, positive rake angles, and none or reduced radial lands.
FIGS. 9A-9H show an endodontic instrument having rolled edges and tapering.
FIG. 17 shows a stress versus strain diagram.
FIGS. 18A-18B show deflection of a cantilevered beam.
FIGS. 25A-25E show another implementation of an endodontic instrument.
FIGS. 27-30 show schematic representations of other implementations of endodontic instruments.

FIGS. 32A-35B are schematics of blanks used for forming the instruments described herein.

Like reference numbers and designations in the various drawings indicate like elements.

DETAILED DESCRIPTION

Reversed Helix

Conventional endodontic instruments have right-handed cutting edges and right handed helices. A flute that forms a right handed helix spirals around the shaft, in a shank to tip longitudinal direction and, furthermore, in a clockwise direction of rotation (as viewed from shank to tip). This configuration is similar to the treads of a screw. Conventional endodontic instruments having this screw like configuration are prone to binding. Furthermore, the radial lands and negative cutting angles typical of convention endodontic instruments predisposed the instruments to premature fatigue and breakage.

An endodontic instrument in accordance with the invention can include a reversed helix. A reversed helix spirals around the shaft of an instrument, in an shank to tip longitudinal direction and, furthermore, in a direction of rotation opposite to the cut direction of rotation. If, for example, the endodontic instrument has a clockwise cut direction of rotation, its helices would spiral in a counter clockwise direction of rotation (along a longitudinal axis of the shaft in a shank to tip direction and as viewed from shank to tip). In this case, the instrument includes right handed cutting edges. That is, the cutting edge is on the leading edge side of the helices as the instrument is rotated in the cut direction of rotation.

Figure 4:
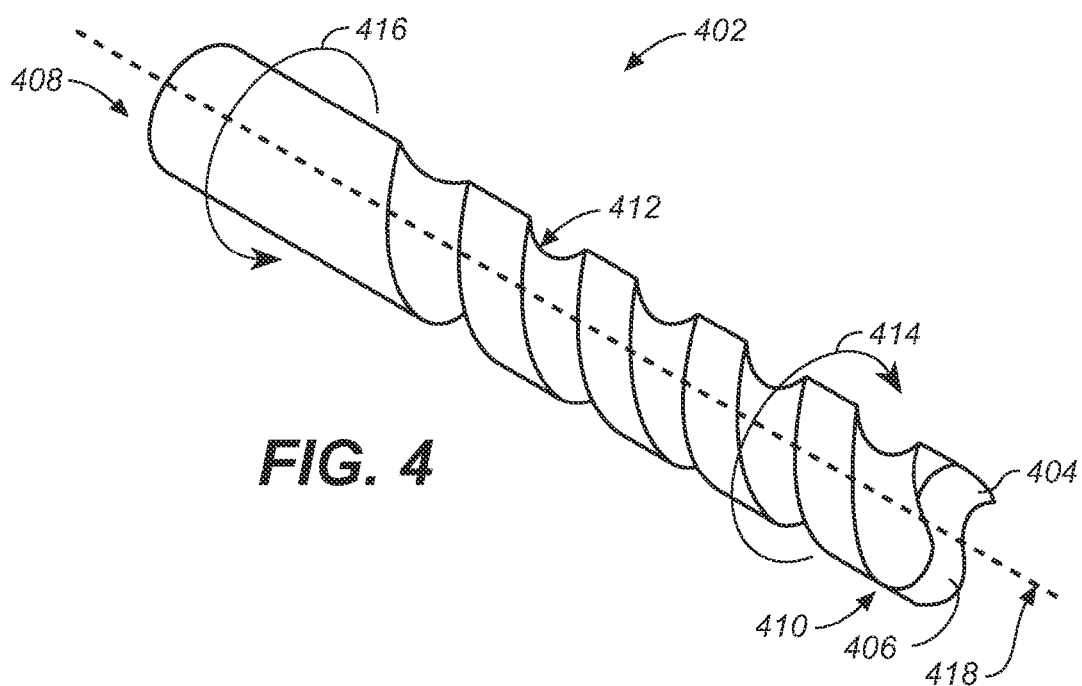
FIG. 4 shows an endodontic instrument having reversed helices.

FIG. 4 shows an example of the described endodontic instrument. The instrument shown includes a shaft 402, helices 404 and 406, shank end (or simply end) 408, tip end (or simply tip) 410. The helix 406, for example, includes cutting edge 412. Thus, the instrument cuts when it is rotated about its longitudinal axis 418 in a counter clockwise direction (as seen from an end to tip perspective), and the cut direction is counter clockwise (as indicated by arrow 414). The direction which helices 404 and 406 spiral around the shaft 402 is clockwise (along the shaft in an end to tip direction and as viewed from an end to tip perspective; as indicated by arrow 416).

Figure 5:
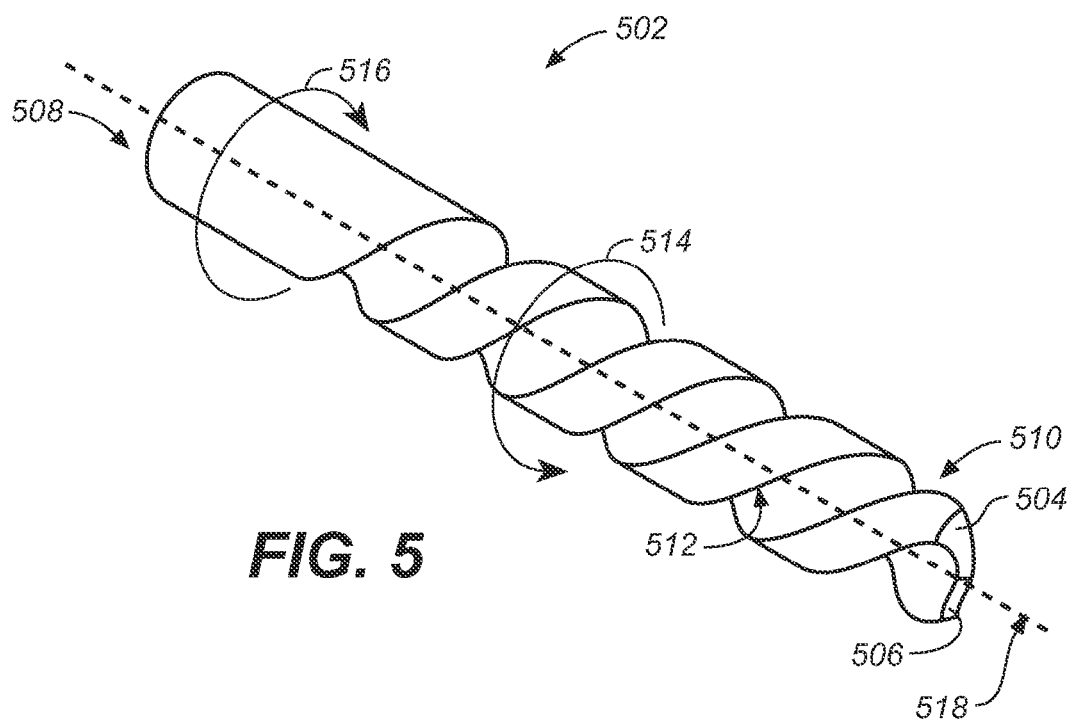
FIG. 5 shows another endodontic instrument having reversed helices.

If the endodontic instrument has a clockwise cut direction of rotation (as seen from an end to tip perspective), then its flutes can spiral in a counter clockwise direction of rotation (along a longitudinal axis of the shaft in an end to tip direction; and as viewed from an end to tip perspective). FIG. 5 shows and example of the described endodontic instrument. The instrument shown includes a shaft 502, helices 504 and 506, shank end (or simply end) 508, tip end (or simply tip) 510. The helix 504, for example, includes cutting edge 512. Thus, the instrument cuts when it is rotated about its longitudinal axis 518 in a clockwise direction (as seen from an end to tip perspective), and the cut direction is clockwise (as indicated by arrow 514). The direction which flutes 504 and 506 spiral around the shaft 502 is counter clockwise (along the shaft in an end to tip direction and as viewed from an end to tip perspective; as indicated by arrow 516).

An endodontic instrument having the reversed helix is generally not prone to binding and can haul debris from its tip to its end, thus removing the debris from the space being prepared. In one implementation, the endodontic instrument can be fabricated from a flexible or super flexible material, such as NiTi or a NiTi alloy. Engine driven instruments, including rotary engine driven instruments, as well as hand instruments can include the described reversed helix configuration.

Figure 6A:
FIGS. 6A and 6B show other endodontic instruments having a reversed helices.
Figure 6B:
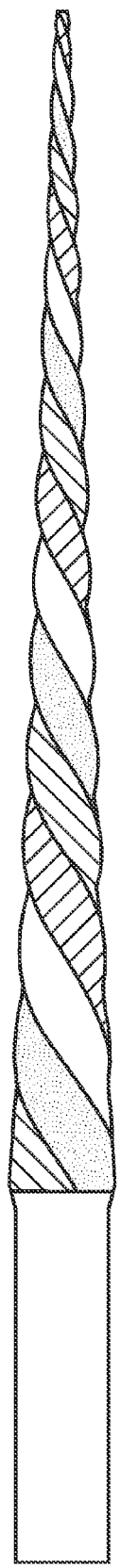

In the above examples, the endodontic instruments shown included only two flutes. Endodontic instruments having any number of flutes and any spline geometry can incorporate the described reversed helix configuration. FIGS. 6A and 6B show implementations of multiple flute endodontic instruments having the reversed helix configuration.

Helices Having Cross Cuts

Figure 7A:
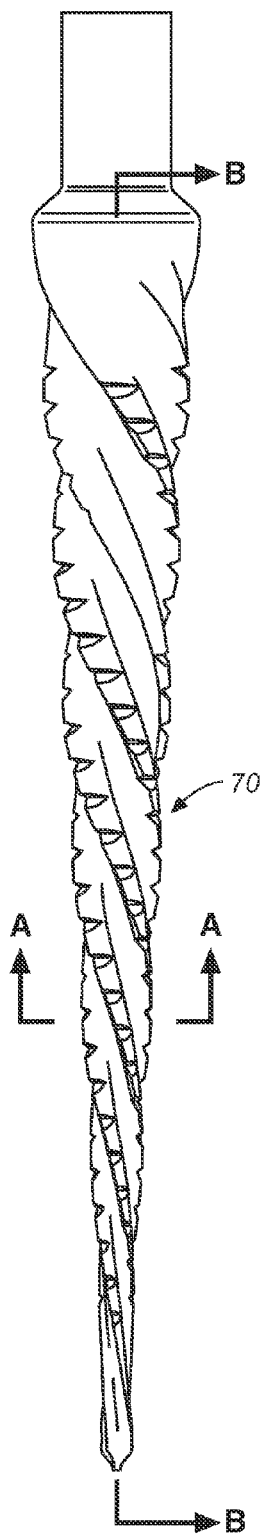
FIGS. 7A-7D show an endodontic instrument having cross cuts on its helices.
Figure 7B:
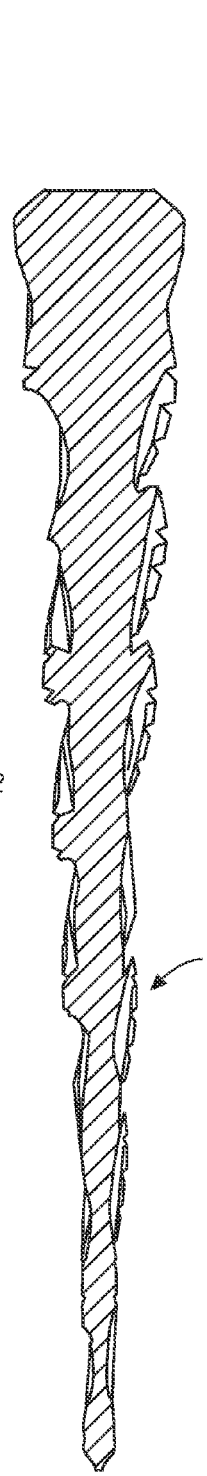
Figure 7C:
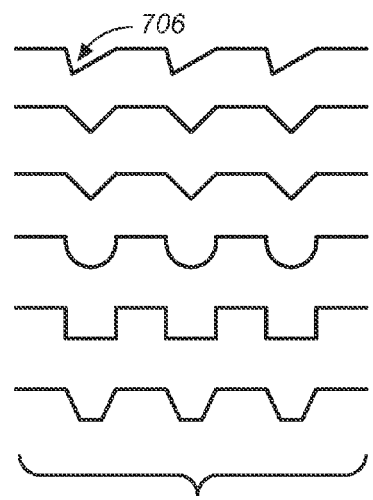
Figure 7D:
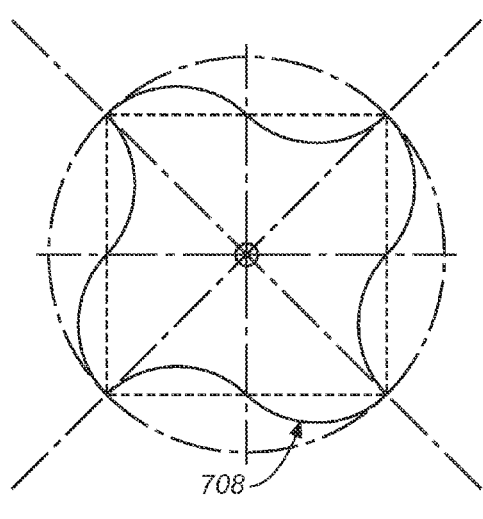

An endodontic instrument in accordance with the invention can include helices that include one or more cross cuts. The cross cuts of a helix can but need not be at right angles to the helix. In general, the cross cuts can have a geometry and depth so as to increase the flexibility of the endodontic instrument and allow the instrument to bend more easily. FIG. 7A shows an instrument 702 that includes helices having cross cuts. FIG. 7B shows a cross section 704 (i.e., cross section B-B) of the instrument 702. FIG. 7C shows the different example geometries which a cross cut can have. The cross cuts can include cutting edges, for example, cutting edge 706, which consequently provide a more efficient cutting device. FIG. 7D shows a cross section 708 (i.e., cross section A-A) of the instrument 702.

Web Designs Having S Shaped Splines, Positive Rake Angles, and None or Reduced Radial Lands FIG. 8A shows an instrument 802, which is one example an endodontic instrument having an S shaped spline, which approximate or approach positive rake angles, and none or reduced radial lands. The instrument 802 includes four helices 804, 806, 808, and 810 and four flutes 812, 814, 816, and 818. FIG. 8B shows a cross section 820 (i.e., cross section A-A) of the instrument 802. The web design shown exhibits a quadrilateral like shape. FIG. 8B shows cross sections 822, 824, 826, and 828 of the flutes. The splines are S shaped, which provides mass that can buttress the cutting edges of the instrument.

The cutting edges (shown as four arcs delimited by points 830, 832, 834, and 836) can have reduced positive rake angles, which makes the cutting edges less prone to breakage than cuttings edge with large cutting angles. In the instant specification, a cutting angle of a cutting edge that is formed by a flute can be defined as the angle between (i) a tangent of the spline of the flute at the cutting edge and (ii) a ray extending radially outward from the center of cross section of the instrument. For example, the cutting edge at point 836 that is formed by flute 822 exhibits a cutting angle $I_1$ defined by tangent 840 and ray 842. Tangent 840 can be mathematically represented as a one-sided derivative, taken at point 836, of a function that represents the spline 844. Alternatively, there are other ways of defining cutting angle. For example, the cutting angle can be defined as the angle $I_2$ between the described tangent 840 and a tangent 846 of a circumference 848 of the instrument at point 836. Under the alternative definition, the cutting angle $I_2$ is said to be neutral or zero when the angle is ninety degrees, positive when greater than ninety degrees, and negative when less than ninety degrees.

An S shaped spline also removes the radial land usually present in conventional endodontic instruments. The crossed hatched area 850 represents a hypothetical radial land. As can be seen, the radial land, if present, would rub against a surface being cut and create unnecessary drag along the working surface of the instrument and render it inefficient and predisposed to breakage.

The described endodontic instrument can be fabricated from a preformed cylindrical metal blanks of nickel titanium. Alternatively, the instrument can be fabricated from others blanks and other materials.

The shank end of the above described instrument can include a latch-type attachment suitable for coupling, usually detachably, to a motor driven chuck. The latch type attachment can also be suitable for coupling to a handle if the instrument is to be used manually. The tip of the instrument can be smooth while maintaining the conicity, taper, and transverse cross sectional shape of the instrument.

The following describes an implementation. The tip of the implementation ends in a pyramidal or parabolic shape and is at least 0.05 mm in diameter and 1-3 mm in length. The cutting length (not including the tip) of the implementation is 8-16 mm in length. In general, the cutting length should be at least 2 mm in length. The cutting edges of the implementation is created by including one to six flutes. Alternatively, the implementation can include additional flutes. The flutes usually begin at a first position near the shank end of the instrument and ends at a second position near the tip end of the instrument. The first position is referred to as a maximum flute diameter (or MxFD) and the second position is referred to as a minimum flute diameter (or MnFD). The flutes are concave and are substantially the same as each other. The flutes have a shape and depth that remains constant along the length of the shaft. Alternatively, the shape and/or depth can vary along the length of the shaft. These flutes are spaced along the circumference of the cutting surface. The spacing can be of uniform intervals or irregular intervals. That is, the helix formation or spirals that progress from the shank end to the tip of the instrument can be spaced at regular intervals or increasingly narrower intervals. In the latter case, a greater number of spirals can be included per unit length along the longitudinal axis of the implementation. Each flute forms a neutral or slightly positive rake angle. The flutes spiral around the shaft of the instrument, completing 360° of rotation for a minimum of 1 mm, and a maximum of 6 mm of axial length of the cutting surface.

Variable Working Surfaces with Flute Modifications and/or Attenuated Cutting Edges The working surfaces or leading edges of conventional endodontic instruments have been manufactured with active or sharp cutting edges along the entire length of the working surface. This configuration can predispose the instrument to great amounts of torque leading to premature fatigue and breakage. One can mitigate the problem by varying the taper and the length of the working surface. As the instrument increased in diameter, the length of the working surface, or the number of cutting flutes (i.e., the number of flutes that form cutting edges) per unit length along the longitudinal axis of the instrument, can be reduced. Although, this configuration does mitigate the amount of torque that the instrument engenders as the size of the instrument increases, eliminating flutes also eliminates the ability of the instrument to continue to haul debris coronally. As a result, the instrument can become easily clogged creating unnecessary drag on the instrument.

Figure 9E:
Figure 9F:
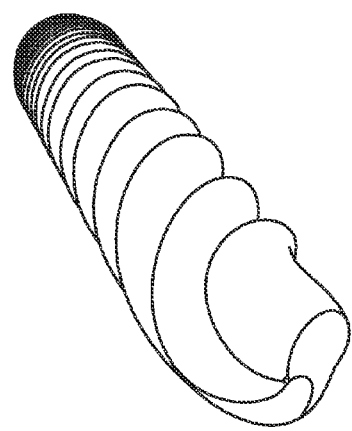
Figure 9G:
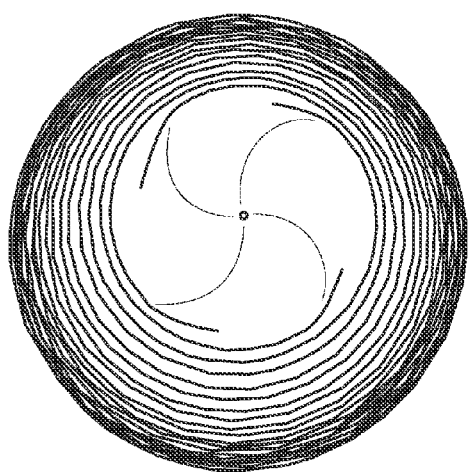
Figure 9H:
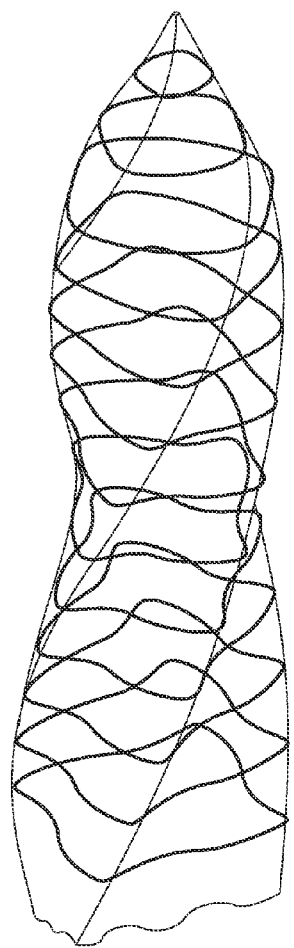

An endodontic instrument in accordance with the invention retains the flutes along the entire length of the working surface to maintain hauling action. The leading edge or the working surface, however, is modified such that only a portion of the working surface cuts. This modification is brought about by blunting or rolling the edge of flutes both at the tip and shank ends of the instrument, leaving the central portion of the cutting surface active. Rolling edges will prevent the instrument from over-enlarging or tearing the foramen of the ECS distally and mitigate drag and pre-mature fatigue proximally. FIGS. 9A 9D show an example instrument that includes a reduced working portion. FIG. 9A shows the instrument 902. FIG. 9B shows the working portion 904 of the instrument 902. FIG. 9C shows a non cutting tip portion 906 of the instrument 902. FIG. 9D shows a non cutting shank end portion 908 of the instrument 902. FIGS. 9E 9H show an implementation in which the instrument 902 tapers from shank to tip.

Endodontic instruments can be provided in sets. A set usually includes instruments of different diameters. In preparing an ECS, an endodontist usually begins the preparation process using the instrument having the smallest diameter. As the ECS is enlarged, the endodontist usually switches to instruments of progressively larger diameters. The rolled edges feature described above can vary from one instrument to another in a set of instruments, with the active surface diminishing in length progressively as the diameter of the instrument increased. This feature would allow the instrument to continue to haul debris coronally, but mitigate the torque that the instrument is subject to when cutting.

Critical Path Set of Endodontic Instruments

Figure 1A:
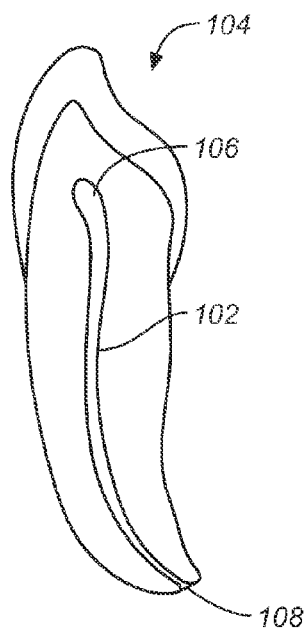
FIGS. 1A and 1B illustrate a root canal procedure.
Figure 1B:
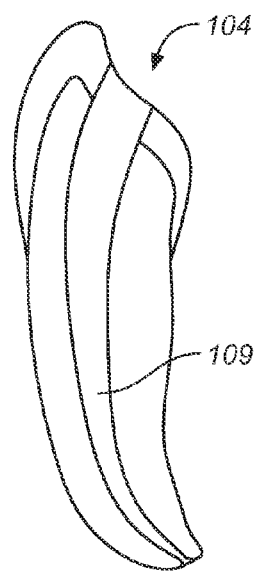
Figure 2A:
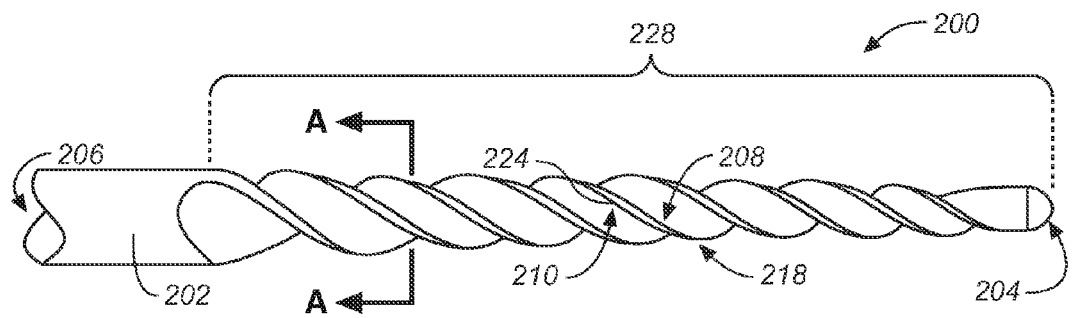
Figure 2B:
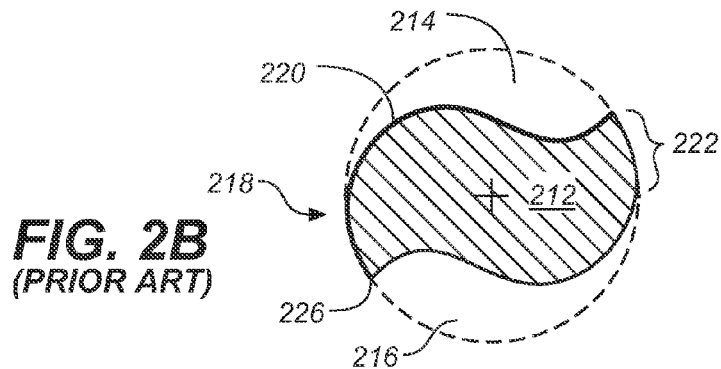
Figure 10A:
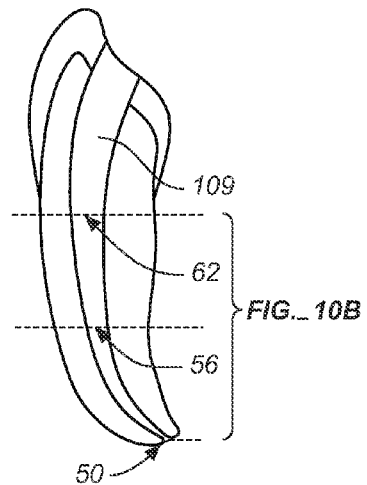
FIGS. 10A-10C illustrate the notion of the critical set of endodontic instruments.

A set of endodontic instruments, the instruments of which can have the same length but different diameters, can be provided for use in seriatim to enlarge progressively the ECS 102 of a tooth (FIG. 1A) and create the continuous cone shaped space 109 (previously shown in FIG. 1B and also shown in FIG. 10A). In particular, the instrument with the smallest diameter is first used to enlarge the ECS 102 to a certain extent. Then, the instrument with the next largest diameter is used to further enlarge the ECS. This process continues until the instrument having the largest diameter is used to complete the creation of the space 109. Progressively enlarging the ECS 102 as described above can usually subject the tooth and the endodontic instruments to stress that is significantly less than the stress that would be exerted if only one instrument were used to created the space 109.

The stress level to which an endodontic instrument is subject can be related to the amount of material the instrument removes. In view of the forgoing, the number of endodontic instruments provided in the set as well as their sizing can be determined so that each instrument of the set is subject to a similar or the same level of stress during its use to remove its apportioned amount of dental material. The determination can be based on a critical set model that will be explain in the following paragraphs.

Figure 10B:
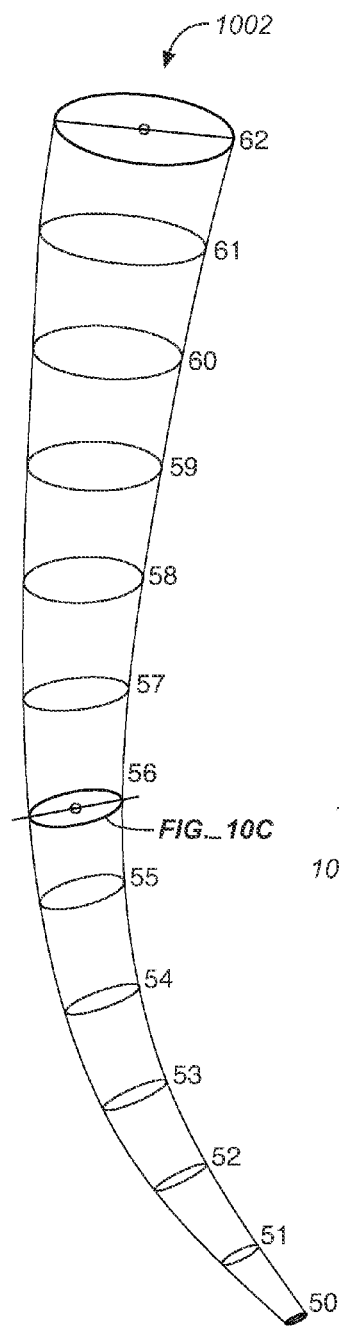

The indicated portion of the space 109 (FIG. 10A), which generally starts at the point in the ECS (referred to below as the curve start point) where a straight line preparation is no longer practical or possible and ends at the foramen of the ECS, can be modeled as the geometric object 1002 shown in FIG. 10B. The object 1002 represents the curved portion of an ideally prepared ECS.

The object 1002 can be incremented along its length, which is typically 12 millimeters, into 12 one millimeter sections. As can be seen, the transverse cross sections that so increment the space 109 are circles that are denoted as 50, 51, ..., 62, where the cross section 50 is at the tip and cross section 62 is at the butt of the space 109.

Note that the shaft (not shown) of each endodontic instrument of the set can be similarly incremented by transverse cross sections denoted as $D_1, D_2, \ldots, D_{12}$, each of which can correspond to a respective cross section of the space 109. $D_6$, for example, corresponds to cross section 56.

The cross section 56 represents the portion of the ECS that has the greatest curvature, usually referred to as the fulcrum. The fulcrum usually occurs at or near the midpoint between the foramen and the above described curve point of the ECS and, furthermore, is generally the point where endodontic instruments are most vulnerable to failure, including, for example, catastrophic breakage.

The set of endodontic instruments can be configured to reduce the probability of failure at or near the $D_6$ cross sections of their shafts. In particular, the set can be configured so that the total amount of dental material to be removed at and around cross section 56 is evenly distributed among the instruments of the set. A set of instruments so configured will be referred to as the critical path set.

Figure 10C:
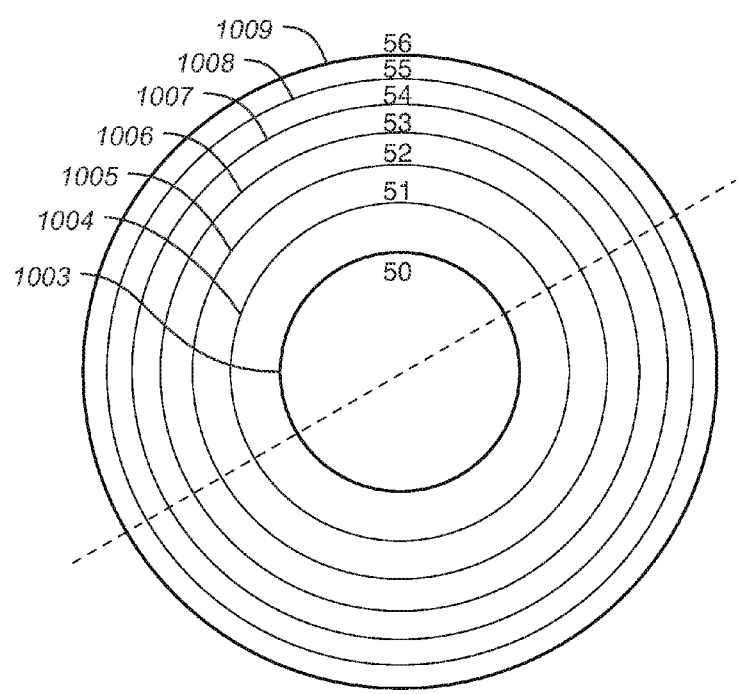

FIG. 10C shows the cross section 56, which includes seven circles, i.e., circles 1003 1009. The circles can define six annuli of equal area. The circles 1003 1009 have, respectively, diameters $d_0$-$d_6$ and radii $r_0$-$r_6$. Note that circle 1003 and 1009 correspond, respectively, to the perimeters of cross section 50 and cross section 56. Each annulus can be defined by its outer and inner circle and, furthermore, can represent the amount of dental material that an instrument is used to remove. The instruments can be sized so that their cross sections at $D_6$ correspond to the circles 1004-1009. That is, the nth instrument is to have a $D_6$ cross section diameter of $d_n$. The first instrument, for example, is to have a $D_6$ cross section diameter of $d_1$.

As can be seen from FIG. 10C, an annulus has an outer circle and inner circle. The area of an annulus can be calculated by taking the difference between the area of the outer circle and the area of the inner circle. Given that ECS is to be enlarged sequentially from 0.20 to 0.70 mm at $D_6$ (and 0.20 to 1.2 mm at $D_{12}$), the area of the annulus defined by circles 1003 and 1009, which as discussed can represent the total amount of material to be removed at or around $D_6$, can be calculated as $$A_{outer\ circle} - A_{inner\ circle} = \pi(0.35)^2 - \pi(0.1)^2$$

$$A \text{ of annulus at } D_6 = \pi(0.1225) - \pi(0.01)$$

$$A \text{ of annulus at } D_6 = \pi(0.1125)$$

For a set of six instruments, the amount of material allotted to each instrument to remove can be represented by diving the above calculated total area by six. Each instrument would then have an increase in cross sectional area at $D_6$ by one-sixth the area calculated above (i.e., the area of the annulus defined by circles 1003 and 1009 at $D_6$), which is calculated as:

$$(A \text{ of annulus at } D6)/6 = [\pi(.1125)]/6$$

$$= \pi 0.01875$$

In general, a formula to determine the D6 radius of an nth instrument can be defined as $$\pi r_n^2 = \pi(r_{n-1})^2 + \pi 0.01875$$

$$r_n^2 = (r_{n-1})^2 + 0.01875$$

$$r_n = [(r_{n-1})^2 + 0.01875]^{1/2} \quad [1]$$

where n represents the sequential position of the instrument in the sequence of instruments in the set, the sequence being based on size. The first instrument in the set, for example, is usually the smallest sized instrument and is the one of the set that is first used to prepare the ECS. Thus, n is an integer that is at least 1. Additionally, $r_n$ is the radius of the $D_6$ cross section of the nth instrument, except for $r_0$, which is the radius of the circle 1003 (i.e., the diameter of the unprepared ECS at D6) shown in FIG. 10C. Alternatively, the formula can be defined as $$\pi r_n^2 = \pi(r_0)^2 + n(\pi 0.01875)$$

$$r_n^2 = (r_0)^2 + n(0.01875)$$

$$r_n = [(r_0)^2 + n(0.01875)]^{1/2} \quad [2]$$

Furthermore, the radius of the $D_6$ cross section of smallest instrument of the set, i.e., instrument No. 1, which corresponds to the radius of the ECS cross section resulting after the first instrument is used to prepare the ECS is $$r_1^2 = r_0^2 + 0.01875$$

$$r_1^2 = (0.1)^2 + 0.01875$$

$$r_1^2 = 0.010 + 0.01875$$

$$r_1^2 = 0.0388$$

$$r_1 = 0.1696$$

Thus, the diameter of the $D_6$ cross section of the first instrument is $$d_1 = 0.339 \text{ mm}$$

Using either formula [1] or formula [2], the values for $d_2$, $d_3$, $d_4$, $d_5$, and $d_6$ at $D_6$ can be derived. Table 1 shows the derived cross-sectional diameters, $d_1$, $d_2$, $d_3$, $d_4$, $d_5$, and $d_6$, that occur at $D_0$, $D_6$, and $D_{12}$. The superscript percentages, e.g., those listed in row D6, each represents the percentage increase in cross-sectional area from the previous diameter or instrument. The average of these changes from $d_1$-$d_6$ at $D_6$ is 24%. The average of the changes from $d_1$-$d_5$ at $D_6$ is 29%.

TABLE 1

|     | $d_0$ | $d_1$ | $d_2$ | $d_3$ | $d_4$ | $d_5$ | $d_6$ |
| --- | --- | --- | --- | --- | --- | --- | --- |
| D0  | 0.20 | 0.20 | 0.20 | 0.20 | 0.20 | 0.20 | 0.20 |
| D6  | 0.20 | $0.339^{70\%}$ | $0.436^{28\%}$ | $0.515^{15\%}$ | $0.583^{13\%}$ | $0.644^{10\%}$ | $0.7000^{8\%}$ |
| D12 | 0.20 | 0.522 | 0.712 | 0.86 | 0.986 | 1.098 | 1.2 |

Table 2 show the cross section diameters of a set of instruments that is similar to the critical set. The average increase in diameter is 29%, which, notably, is achieved by logarithmic progression and not linear progression of conventional set, as is the case in conventional sets of instruments.

TABLE 2

|    | 15/05 | 20/06 | 24/07 | 27/08 | 29/09 | 30/10 |
|----|-------|-------|-------|-------|-------|-------|
| D1 | 15 | 20 | 24 | 27 | 29 | 30 |
| D2 | 20 | 26 | 31 | 35 | 38 | 40 |
| D3 | 25 | 32 | 38 | 43 | 47 | 50 |
| D4 | 30 | 38 | 45 | 51 | 56 | 60 |
| D5 | 35 | 44 | 52 | 59 | 65 | 70 |
| D6 | $40^{100\%}$ | $50^{25\%}$ | $59^{18\%}$ | $67^{13\%}$ | $74^{10\%}$ | $80^{8\%}$ |
| D6 Critical Set | $.339^{70\%}$ | $.436^{28\%}$ | $.515^{15\%}$ | $.583^{13\%}$ | $.644^{10\%}$ | $.7000^{8\%}$ |
| D7 | 45 | 56 | 66 | 75 | 81 | 90 |
| D8 | 50 | 62 | 73 | 83 | 90 | 100 |
| D9 | 55 | 68 | 80 | 91 | 99 | 110 |
| D10 | 60 | 74 | 87 | 99 | 108 | 120 |
| D11 | 65 | 80 | 94 | 107 | 117 | 130 |
| D12 | 70 | 86 | 101 | 115 | 126 | 140 |

Table 3 shows the cross section diameters of another set of instruments that is similar to the critical set. The percent change in the D6 cross section diameter of this set is also 29%. Note however, that there is a substantial increase in the diameter of the instruments from d5 to d6, which can still be considered safe, because the rigidity of this instrument prevents any meaningful flexure eliminating fatigue and breakage.

TABLE 3

|    | 15/04 | 20/05 | 24/06 | 27/07 | 30/08 | 35/10 |
|----|-------|-------|-------|-------|-------|-------|
| D1 | 15 | 20 | 24 | 27 | 30 | 35 |
| D2 | 19 | 25 | 30 | 34 | 38 | 45 |
| D3 | 23 | 30 | 36 | 41 | 46 | 55 |
| D4 | 27 | 35 | 42 | 48 | 54 | 65 |
| D5 | 31 | 40 | 48 | 55 | 62 | 75 |
| D6 | $35^{75\%}$ | $45^{28\%}$ | $54^{20\%}$ | $62^{15\%}$ | $70^{13\%}$ | $85^{21\%}$ |
| D6 Critical Set | $.339^{70\%}$ | $.436^{28\%}$ | $.515^{15\%}$ | $.583^{13\%}$ | $.644^{10\%}$ | $.7000^{8\%}$ |

Table 4 shows the cross section diameters of yet another set of instruments that is similar to the critical set. These instruments corresponds very closely to a critical set at D6. The average increase in the D6 cross section diameter from the first to the fifth instrument is 29%, which is identical to the critical set. The instrument with the smallest diameter, the 15/04 can also be discounted or set aside from a critical set, because it is extremely flexible and intrinsically safe.

Optionally, where a set includes one or more instruments that have cross sectional diameters that vary along the shaft, as is the case for the instruments represented in the tables included in this specification, one can roll the cuttings edges of portions of an instrument that has the same diameter as another instrument of the set. Doing so can reduce the resistance to which the instrument is subject and make the instrument even less predisposed to failure. In the tables, shaded cells indicate that the portions listed in the cells can have rolled edges.

TABLE 4

|    | 15/04 | 20/05 | 23/06 | 25/07 | 27/08 | 30/10 |
|----|-------|-------|-------|-------|-------|-------|
| D1 | 15 | 20 | 23 | 25 | 27 | 30 |
| D2 | 19 | 25 | 29 |  | 35 | 40 |
| D3 | 23 | 30 | 35 | 39 | 43 | 50 |
| D4 | 27 | 35 | 41 | 46 | 51 | 60 |
| D5 | 31 | 40 | 47 | 53 | 59 | 70 |
| D6 | $35^{75\%}$ | $45^{29\%}$ | $53^{18\%}$ | $60^{13\%}$ | $67^{12\%}$ | $80^{19\%}$ |
| D6 Critical | $.339^{70\%}$ | $.436^{28\%}$ | $.515^{15\%}$ | $.583^{13\%}$ | $.644^{10\%}$ | $.7000^{8\%}$ |
| D7 | 39 | 50 | 59 | 67 | 75 | 90 |
| D8 | 43 | 55 | 66 | 74 | 83 | 100 |
| D9 | 47 | 60 | 72 | 81 | 91 | 110 |
| D10 | 51 | 65 | 78 | 88 | 99 | 120 |
| D11 | 55 | 70 | 84 | 95 | 107 | 130 |
| D12 | 59 | 75 | 90 | 102 | 115 | 140 |

Table 5 shows the cross section diameters of yet another set of instruments that is similar to the critical set. These instruments deviate slightly from the critical set; however, it mimics tips sizes and tapers that are familiar to most practitioners.

TABLE 5

|  | 15/04 | 20/05 | 25/06 | 30/07 | 35/08 | 40/10 |
|---|---|---|---|---|---|---|
| D1 | 15 | 20 | 25 | 34 | 36 | 40 |
| D2 | 19 | 25 | 31 | 41 | 44 | 50 |
| D3 | 23 | 30 | 37 | 48 | 52 | 60 |
| D4 | 27 | 35 | 43 | 55 | 60 | 70 |
| D5 | 31 | 40 | 49 | 62 | 68 | 80 |
| D6 | $35^{75\%}$ | $45^{28\%}$ | $55^{22\%}$ | $69^{25\%}$ | $76^{11\%}$ | $90^{18\%}$ |
| D6 Critical Set | $.339^{70\%}$ | $.436^{28\%}$ | $.515^{15\%}$ | $.583^{13\%}$ | $.644^{10\%}$ | $.7000^{8\%}$ |

These calculations and the instrument sets that have been proposed are again, functions of the formula for the area of a circle. Similar calculations can be also be made using formulas for circumference of a circle or the surface area of a frustum. Further, calculations can also be made using the average of the surface areas of all the intersecting diameters of the critical path, their circumferences, the surface areas of the frustums or portions or combinations thereof.

One alternative, for example, can be implemented such that the above described equal distribution of dental material to be removed can be calculated not only for the $D_6$ cross section, but for any combination of $D_1$-$D_6$ cross sections, or even for any cross section or every cross sections along the axis of the shaft.

The above described differences in $D_6$ cross section areas of instruments, for example, the difference in the $D_6$ cross section areas of the first and second instruments and the difference in the $D_6$ cross section areas of the second and third instruments, need not be exactly equal. The differences in areas can be substantially equal, for example, one difference being no more than twice the other difference.

The cross sections used in the above described model need not be $D_6$ cross sections but can be cross sections substantially the same as the $D_6$ cross section. Cross sections within 5 millimeters of the $D_6$ cross section, for example, can be used in the model.

Figures 11A, 11B:
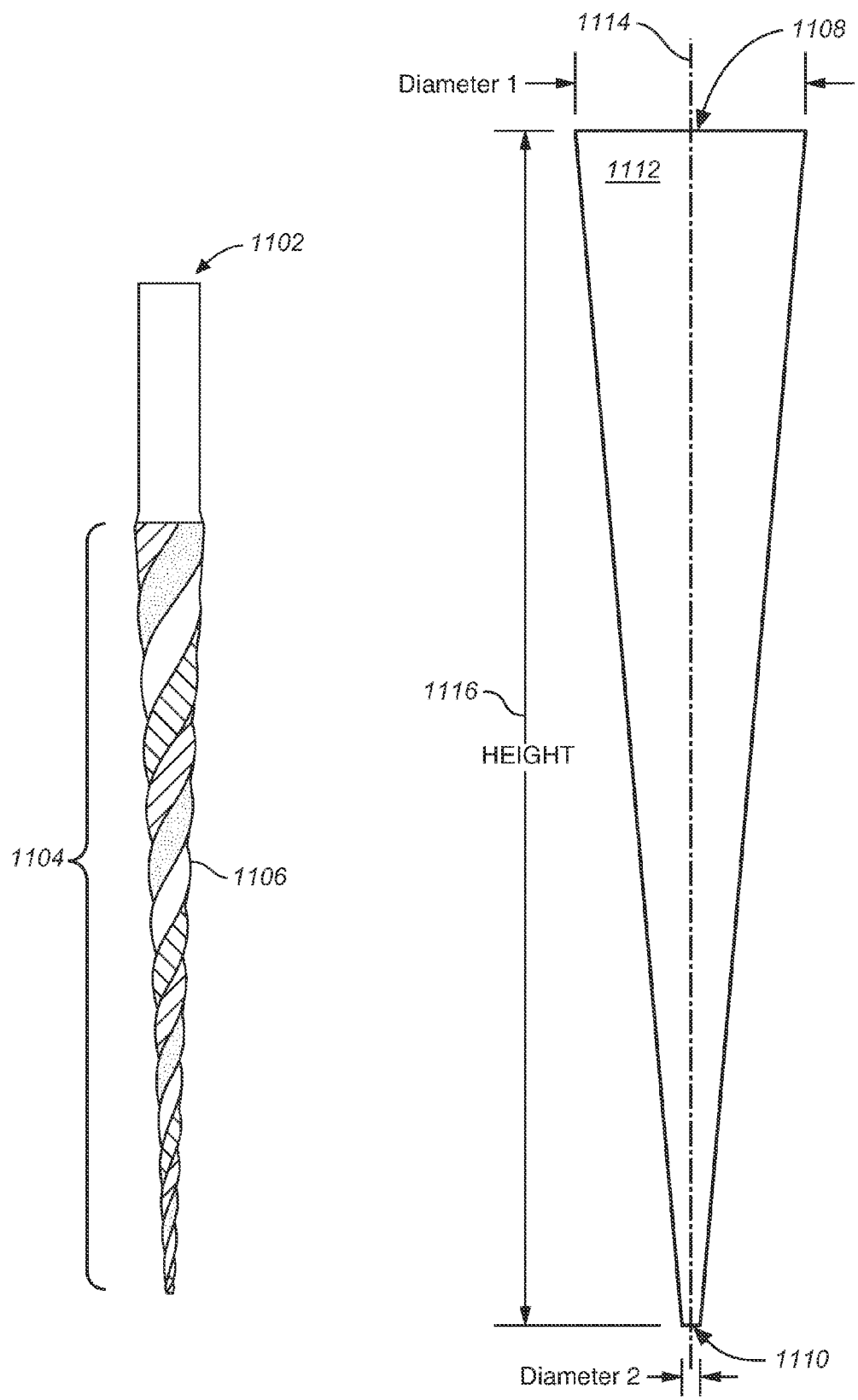
FIGS. 11A-11D illustrate the contact area of an endodontic instrument.

As an another alternative, a critical set can be defined based on a calculation of the effective contact area of each endodontic instrument in a set of endodontic instruments. The effective contact area is the exposed surface area of a cone like shape, which, for an endodontic instrument, is defined as shown in FIGS. 11A and 11B. The example endodontic instrument 1102 shown includes a working portion 1104, which as discussed above, is the portion of the instrument that includes cutting edges, e.g., cutting edge 1106. The working portion includes cross sections, each defining a circle into which the corresponding cross section can be inscribed. The circle having the greatest diameter is usually defined by the largest cross section, which usually occurs at or near the proximal end of the working portion (i.e., the end that is closest to the shank and farthest away from the tip of the endodontic instrument). The circle having the smallest diameter is usually defined by the smallest cross section, which usually occurs at or near the distal end of the working portion (i.e., the end that is closest to the tip). In most cases, the described largest and smallest circles are the base 1108 and the top 1110, respectively, of a cone like shape 1112. The base 1108 has a first diameter and the top 1110 has a second diameter that is usually smaller than the first diameter. The distance along the longitudinal axis 1114 of the endodontic instrument defines the height 1116 of the cone like shape 1112. This cone like shape 1112 has an exposed surface area called a frustum, which excludes the surface area of the base 1108 and the top 1110. The exposed surface area can be mathematically defined, for example, by integrating the circles described along the height of the cone like shape.

Figure 11C:
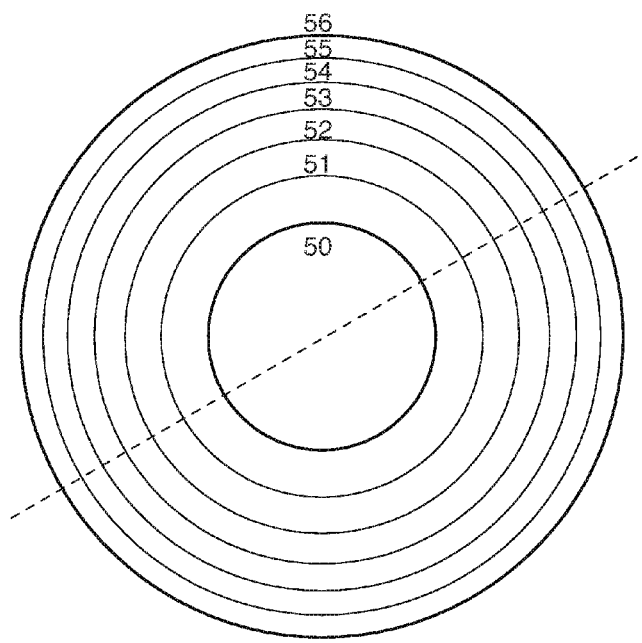
Figure 11D:
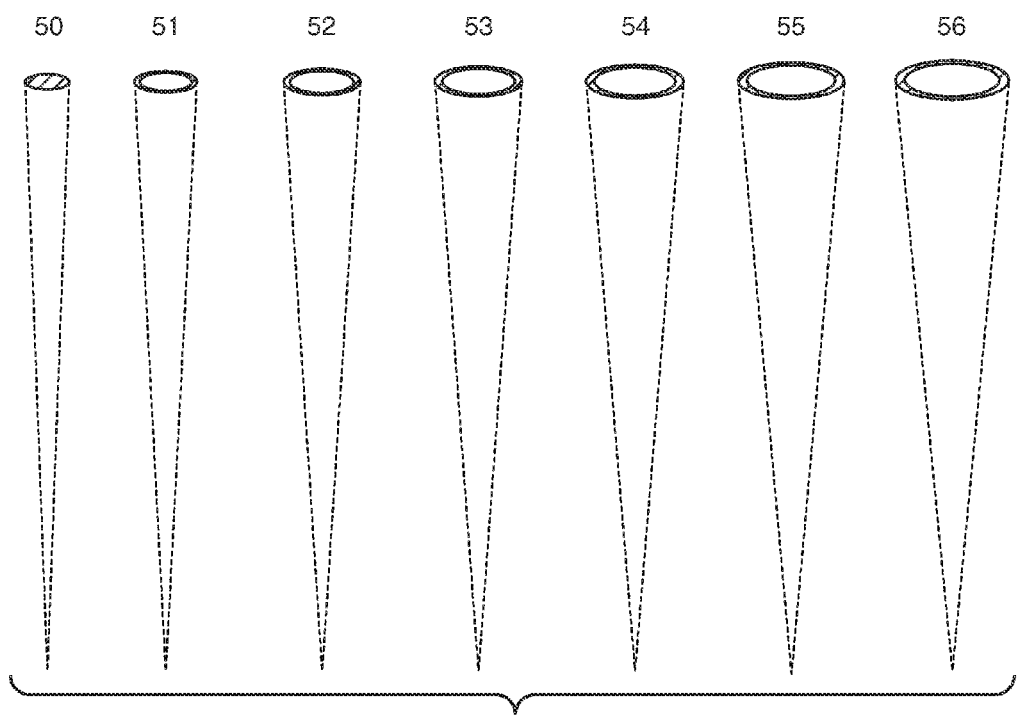

When a critical set is based on the described effective contact area (i.e., the described surface area of the cone like shape), the endodontic instrument in a critical set of endodontic instruments can be sized such that the increase of the effective contact area from one endodontic to the next greater sized endodontic instrument is substantially the same. FIGS. 11C and 11D show six example cone like shapes of an example critical set of endodontic instruments. The change in surface area between any adjacent shapes is substantially constant. In cases where an endodontic instrument includes a working portion that runs to the tip of the instrument, the cone like shape is a cone.

Alternatively, a critical set can be defined differently from the ways described above. The criterion that should be satisfied is that each endodontic instrument in a set be subject to substantially the same level of torsional stress. Distributing the torsional stress as described reduces breakage.

Figure 12:
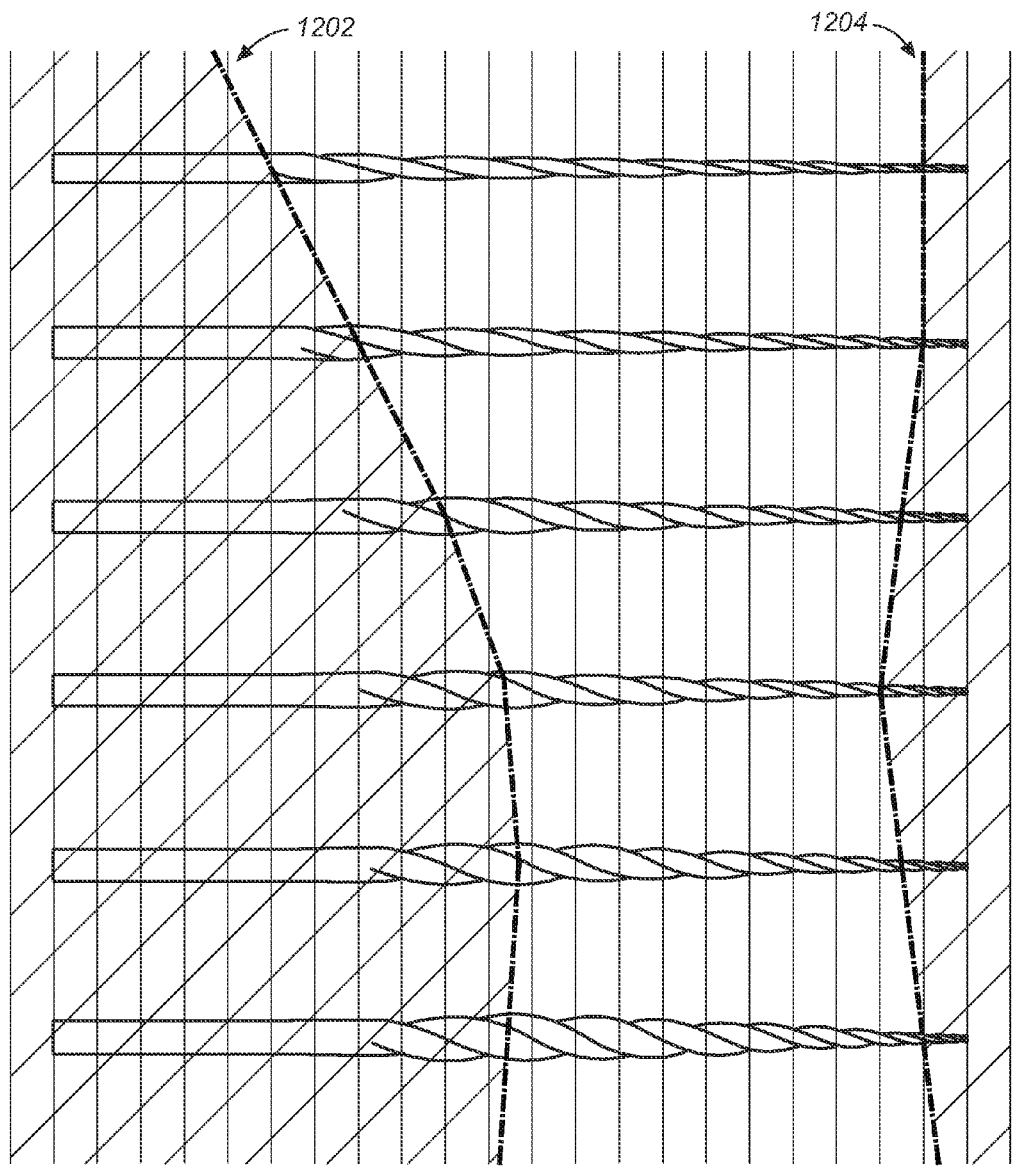
FIG. 12 illustrates the working portion of a critical path set of endodontic instruments.

Distribution of the torsional stress can be fined tuned by changing the working portion of an instrument, as was described above. Reducing the working portion of an instrument, for example, can reduce the level of torsional stress to which the instrument is subject during its use. FIG. 12 shows an implementation of a set of endodontic instruments where the working portion varies from instrument to instrument so that the instruments are subject to substantially the same level of stress during their use. (The dashed lines 1202 and 1204 delimit the working portions.)

A critical set can include more or less than six instruments. The number of instrument depends on the amount of dental material to be removed, with more instruments being needed to removed more dental material. The number of instruments, however, should not be so numerous as to impeded the ECS preparation by requiring the practitioner to frequently switch instruments.

Critical Path Set that Includes a Combination of Reversed Helix Instruments and Non Reversed Helix Instruments As discussed above, using a reversed helix instrument can reduce the risk of the instrument binding with the tooth being worked. Such an instrument can thus be extremely useful during the initial removal of dentin (a preliminary enlargement phase of ECP), when the risk of binding can be great. However, during later stages of ECP, the hauling capacity of the reversed helix instrument can be reduced as dentin chips accumulate in the flutes of the instrument. The accumulation can prevent the reversed helix instrument from cutting into the tooth being work to the instrument's full working length. Moreover, the reversed helix instrument can includes flutes that have steep helix angles (and consequently large pitch) and/or deep flutes. When it includes these features, the reverser helix instrument can leave an irregular surface area on the walls of a canal that require additional planning.

In one implementation, a set of critical path instruments, for example, the set listed in Table 3 above, includes a combination of instruments that have reversed helices and instruments that do not have reversed helices. The first, third, and fifth instruments (i.e., sizes 15/4, 24/06, and 30/08) of the set each has reversed helices. The second, fourth, and sixth instruments (i.e., sizes 20/05, 27/07, and 35/10) of the set each does not have reversed helices. One would thus use, in an alternating fashion, a reversed helix instrument and a non reversed helix instrument during a preparation stage from D1 to D6. In a sense, the reverse helix instrument can be used as a rough reamer and the non reversed helix instrument subsequent to the reversed helix instrument in the set would be used as a finishing reamer.

Because the described accumulation does not occur with instruments without reversed helices, they can be used during the later stages of ECP to provided the needed hauling. Furthermore, the non reversed helix instruments of a set can include features typical of a finishing reamer, for example, having any combination of (i) 3 or 4 leading edges, (ii) lower helix angles and shorter flute pitch, (iii) shallower flutes, (iv) less (parabolic) relief or lower relief angles behind the leading edges, (v) a neutral or negative rake angle. Instruments of a set having reversed helix and non-reversed helix instruments, can have reduced or no radial lands, which can predispose the instrument to drag, premature wear, and/or breakage.

As discussed above, the portion of the root canal space from D1 to D6, especially D6, is the critical or unsafe zone of the root canal space. This is area that is the narrowest, and the most curved and is associated with the greatest number of instruments failures or fractures. In some implementations, tip sizes and tapers of instruments in a set, from D1 to D6, can be fabricated so that the instruments without reversed helices each has a slightly smaller tip size and a slightly larger taper than does the preceding reversed helix instrument. Such tip sizes and taper allows the non reversed helix instruments of a set to readdress the apical portion of the root canal space prepared by the preceding reversed helix instrument and capture any debris that might have remained, mitigating the opportunity of apical obstructions or blockage. From D7 to D12, the safe zone of the root canal system, tapers of instruments in a set can be fabricated so that the diameter of each instrument of the set progressively increases.

Table 6 shows an implementation of the above described tip size and taper configuration. Note that eight instruments have been included, four reversed helix instruments of the critical path design with left handed helix and right handed cut (L/R) and four non reversed helix instruments with right handed cut and right handed helix (R/R). Note also that the last two columns represent two different sequences with R/R. These instruments have significantly large diameters as breakage is usually not an issue.

TABLE 6

|  | 16/04 (L/R) | 15/05 R/R | 18/06 L/R | 17/07 R/R | 20/08 L/R | 19/09 R/R | 22/10 L/R | 21/12 R/R | Alternate 24/10 R/R |
|---|---|---|---|---|---|---|---|---|---|
| D1 | 16 | 15 | 18 | 17 | 20 | 19 | 22 | 21 | 24 |
| D2 | 20 | 20 | 24 | 24 | 28 | 28 | 32 | 33 | 34 |
| D3 | 24 | 24 | 30 | 31 | 36 | 37 | 42 | 45 | 44 |
| D4 | 28 | 29 | 36 | 38 | 44 | 47 | 52 | 57 | 54 |
| D5 | 32 | 34 | 42 | 45 | 52 | 56 | 62 | 69 | 64 |
| D6 | 36 | 39 | 48 | 52 | 60 | 65 | 72 | 81 | 74 |
| D6C/S | $.339^{70\%}$* |  |  | $.515^{15\%}$ |  |  |  | $.7000^{8\%}$ |  |
| D7 | 40 | 44 | 54 | 59 | 68 | 74 | 82 | 93 | 84 |
| D8 | 44 | 49 | 60 | 66 | 76 | 83 | 92 | 105 | 94 |
| D9 | 48 | 54 | 66 | 73 | 84 | 92 | 102 | 117 | 104 |
| D10 | 52 | 59 | 72 | 80 | 92 | 101 | 112 | 129 | 124 |
| D11 | 56 | 64 | 78 | 87 | 100 | 110 | 122 | 141 | 134 |
| D12 | 60 | 69 | 84 | 94 | 108 | 119 | 132 | 143 | 144 |

Optionally, the non-reversed helix instruments of a set can include all of the features of an ideal finishing reamer, for example, (i) multiple leading edges with neutral or negative rake angles (without radial lands), (ii) lower (or higher) helix angles and shorter (or longer) flute pitch, and (iii) shallow flutes. Such non reversed helix instruments will generally remain safe when used in conjunction with the reverse helix instruments of the set. As discussed above, there may be some justification for using a non reversed helix instrument that is of significantly larger diameter than the reverse helix instrument immediately preceding in the set. Such use can be limited depending on the severity of the curvature of the canal being prepared.

Optionally, the reversed helix instruments of the set can have flutes that spiral insignificantly and are substantially straight. As with the reversed helix configuration, the straight helix design also does not bind.

Swagger

As applied to an endodontic file or reamer, phenomenon of "swagger" is viewed as a transverse mechanical wave, which can be modified, and is comparable to the transverse wave that can be produced along a stretched rope or string. If one ties the loose end of a long rope to a stationary point, stretches the rope out horizontally, and then gives the end being held a back-and-forth transverse motion, i.e., provide an excitation force, $F_e$, the result is a wave pulse that travels along the length of the rope. Observation shows that the pulse travels with a definite speed, maintaining its shape as it travels, and that the individual segments making up the rope move back and forth in a direction perpendicular to the rope's equilibrium position. In physics, this principle can be expressed mathematically by the formula $y=f(x, t)$. Here, the equilibrium position is selected along the x-axis (corresponding to the stretched rope), and the transverse displacement of any point away from this position is y (i.e., the maximum displacement of the rope, or amplitude). Thus, y is a function of both x (the undisplaced position of the point) and time t. This is called the wave function.

At any time t, if one takes a picture of the instantaneous shape of the rope, we observe that y varies sinusoidally with x.

This same system can function in three dimensions whereby an excitation force is applied along both the y- and the z-axes. Here, at any time t, if one takes a picture of the instantaneous shape of the rope, we find that y and z vary sinusoidally with x. Again, using the stretched rope as an example, the rope is observed to produce a spiral or helical wave. Interestingly, if one applies a lateral force $F_l$ somewhere along the x-axis as an excitation force, $F_e$, is applied the same phenomenon is observed; whereas, the portion of the rope distal to the lateral force will also spiral.

In preparing an endodontic cavity space, ECS, along the critical path, CP, with a flexible rotary instrument, a similar system can be configured. The instrument is bound in a somewhat fixed position at one end, by the elbow or greater curvature of the canal, and at the other end by the head of the hand-piece as it is rotating. Observation of an endodontic instrument with a square, or doubly symmetric cross-section rotating in the ECS, appears to have little, if any, deviation from the axis of rotation. An instrument with a singly symmetric (trapezoidal or triangular) cross section, acts like a rope with an excitation force or forces applied along the y and z-axes, or one with an excitation force along the y-axis and a lateral force applied somewhere along its length. The lateral force, or moment, in this instance, is the resultant that is produced by relocating the center of mass of the instrument away from the x-axis.

Most of the mathematics for helical wave theory focuses on hydrodynamics, acoustics and electromagnetic fields. Fortunately, Newtonian physics provides a plethora of laws and principles, which can be applied to this phenomenon.

Figure 13:
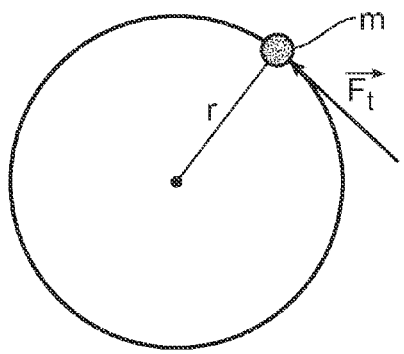
FIG. 13 shows a path of a mass moving in a circle.

If one considers the relationship between torque $\lambda$ and angular acceleration $\alpha$ of a point mass m, one can better understand the physical nature of swagger. Referring to FIG. 13, a mass m moving in a circle of radius r acted on by a tangential force $F_t$.

Using Newton's second law to relate $F_t$ to the tangential acceleration $\alpha_t = r\alpha$ where $\alpha$ is the angular acceleration $$F_t = m\alpha_t = mr\alpha.$$

and the fact that the torque about the center of rotation due to $F_t$ is $\lambda = F_t \cdot r$, one arrives at $$\lambda = mr^2\alpha.$$

For a rotating rigid body made up of a collection of masses $m_1, m_2 \ldots m_i$ the total torque about the axis of rotation is $$\lambda = \Sigma \lambda_i = \Sigma(m_i r_i^2)\alpha.$$

The second equation may consider the angular acceleration of all the points in a rigid body as the same, so it can be taken outside the summation. Thus, if a constant torque $\lambda_i$, as is applied in a torque controlled dental hand-piece, were applied to a mass $m_i$, the acceleration of $m_i$ would increase or decrease exponentially as the radius r of $m_i$ changed.

Torque, like the waves along a stretched rope, must be defined about a particular set of axes. Further considering the moment of inertia, I, of a rigid body with mass $m_i$ gives a measure of the amount of resistance the body has to changing its state of rotational motion. Mathematically, the moment of inertia is $$I = \Sigma m_i r_i$$

The expression for torque is $$\lambda = I\alpha.$$

This is the rotational analogue of Newton's second law. Applying this principal to the center of mass or the centroid C of the rigid body yields $$F_{total} = m\alpha_{cm}$$

where, $\alpha_{cm}$ is the acceleration of the center of mass.

The moment of inertia, like torque must be defined about a particular set of axes. It is different for different choices of axes. The choice of axes is arbitrary, and may be selected in such a way which best suits the particular application, and its respective geometry.

Extended objects can be considered as a very large collection of much smaller masses glued together to which the definition of moment of inertia given above can be applied.

Like torque, the moment of inertia depends on how the mass is distributed about the axis. For a given total mass, the moment of inertia is greater if more mass is farther from the axis than if the same mass is distributed closer to the axis.

If one considers what occurs when a number of masses $m_1, m_2, \ldots, m_i$ are distributed along a line, the measure of the tendency of a mass $m_i$ to rotate about a point at distance x away is called the moment of the body about the point. This moment is measured by the quantity mx, and takes into account that the tendency is larger when either the mass or the distance to the center of rotation is larger.

With more than i=2 masses $(m_1, m_2, \ldots, m_i)$ placed at positions $x_1, x_2, \ldots, x_i$ respectively along a coordinate line, the moment M of the system of masses is just the sum of the individual moments $m_1 x_1 + m_2 x_2 + \ldots + m_n i$. When M=0, the system will not rotate about the point at the origin, and therefore is in equilibrium.

Thus, when the center of mass of the system corresponds to the axis or rotation, the system is in equilibrium and the instrument turns evenly around the axis. When the center of mass or the centroid or the system is at a distance from the center of rotation, similar to an endodontic instrument of singly symmetric cross section, the system is out of equilibrium and will tend to swagger.

Another interpretation of moment of inertia is the capacity of the cross section of a system to resist bending. In a two dimensional space, this may be considered in reference to the x- and y-axes. The Second Moment of the Area can be described in the simplest terms as $$I_x = \Sigma A y^2$$

For a thin slice or cross section of a system with uniform thickness and density, also called a lamina, the location of the centroid along the y-axis could be expressed as y=the square root of $I_x/A$.

An ideal endodontic instrument of singly symmetric cross section would have a center of mass or centroid with geometric coordinates, which allows the instrument to cut the inner and outer walls along the critical path of the ECS evenly. This centroid would have an angular acceleration $\alpha_{cm}$ larger than the $\alpha_{ar}$ or angular acceleration at the geometric axis or rotation with torque $\lambda_x$ provided by the dental hand piece. Returning to the formula for torque $$\lambda = mr^2 \alpha$$

With constant torque $\lambda$, the angular acceleration $\alpha_{cm}$ increases with respect to $\alpha_{ar}$, as $r_{cm}$ deviates from the axis of rotation. Point mass systems are mathematical systems, which can better describe this effect in two and three dimensions.

A system of point masses $m_1, m_2, \ldots m_i$ located in two dimensional space have a moment with respect to any line L in the plane; it is defined to be the sum $M_L = m_1 d_1 + m_2 d_2 + \ldots + m_n d_i$, where the $d_i$ are the (directed) distances from the masses $m_i$ to the line L. In particular, if the masses are located at the points with coordinates $(x_1, y_1), (x_2, y_2), \ldots, (x_n, y_n)$, then the moment of the system about the y-axis is $M_y = \Sigma m_i x_i$ while the moment about the x-axis is $M_x = \Sigma m_i y_i$.

As a result, the formulas $X=M_y/m$, $Y=M_x/m$ give the coordinates of a point (X, Y) about which the system is in equilibrium in both the x- and y-directions. This point is the center of mass of the two-dimensional system and the distribution of masses will balance on the plane at this point.

Now if instead of a discrete system of masses, consider a planar lamina which extends across a region R in the plane, so that at each point (x, y) in R there is a variable mass density $\rho(x, y)$, measured in units of mass per unit area, then the total mass of the lamina is given by the double integral $$m = \iint_R \rho(x,y) dA$$

The moment $M_y$ of the lamina with respect to the y-axis is then $\iint_R x\rho(x,y)dA$ and similarly $M_x = \iint_R y\rho(x,y)dA$. Furthermore, the same formulas used above allow one to find the center of mass (X, Y) of the lamina.

If the lamina has uniform density, that is, if $\rho(x, y) = \rho$ is constant, then the computation of the center of mass simplifies to $$(X, Y) = \left( \iint_R x\rho(x, y)dA \bigg/ \iint_R \rho(x, y)dA, \iint_R y\rho(x, y)dA \bigg/ \iint_R \rho(x, y)dA \right)$$

$$= \left( \iint_R x dA \bigg/ \iint_R dA, \iint_R y dA \bigg/ \iint_R dA \right)$$

Thus, the center of mass depends in this case only on the shape of the lamina and not its density. For this reason, we often refer to the center of mass of a lamina of constant mass density as the centroid of the region R that defines its shape.

In 3D-space, one can measure moments of solids about planes. For instance, $M_{xy} = \iiint_S z\rho(x,y,z)dV$ is the moment of the solid S about the xy-plane, and the center of mass (X, Y, Z) of S satisfies the equations $$X = M_{yz}/m, \; Y = M_{xz}/m, \; Z = M_{xy}/m,$$

$M_{xy} = \iiint_S \rho(x,y,z)dV$ being the total mass of S.

In the same way that mx measures the moment of a point mass m a distance x from a point, line, or plane in 1-, 2-, or 3-space, the second moment or moment of inertia $mx^2$ measures the resistance of the body to rotation about the point, line, or plane. In the continuous case, this leads to the formulas $$I_x = \iint_R x^2 \rho(x,y)dA, \; I_y = \iint_R y^2 \rho(x,y)dA$$

for the moments of inertia for a lamina in 2-space about the coordinate axes. Because $$I_x + I_y = \iint_R x^2 \rho(x,y)dA + \iint_R y^2 \rho(x,y)dA = \iint_R r^2 \rho(x,y)dA$$

$I_0 = I_x + I_y$ is the moment of inertia of the lamina about the origin. This applies to the mechanics of thin plates that spin about a point in the same plane in which they lie. Moments of inertia are naturally extended into 3D-space.

Figure 14:
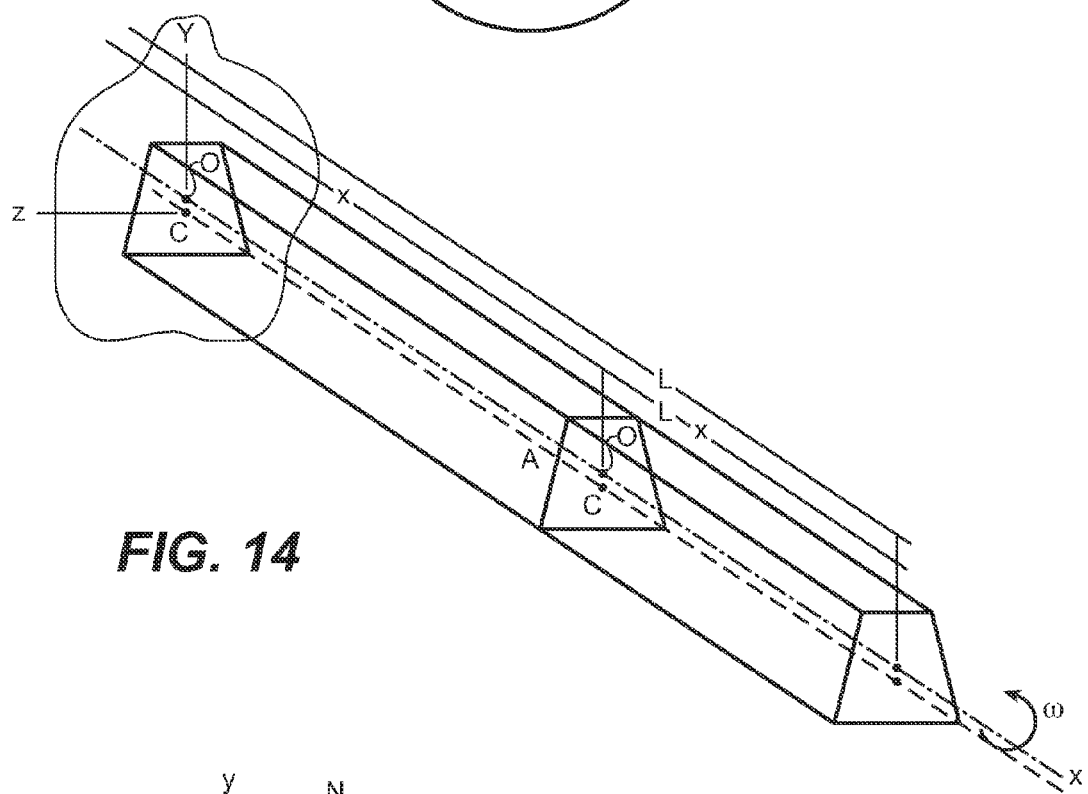
FIG. 14 shows a schematic of a portion of an instrument have a trapezoidal cross section.

In the field of mechanical engineering called dynamics of rigid bodies, it is useful to draw free body and kinetic diagrams of a cross section of the body. Considering the prismatic (i.e., constant cross sectional area along its length) rotating instrument with a singly symmetric trapezoidal cross section as shown in FIGS. 14 and 15. In this case the convention for choice of axis is to orient the axis of rotation of the instrument along the x-axis.

Figures 15A, 15B:
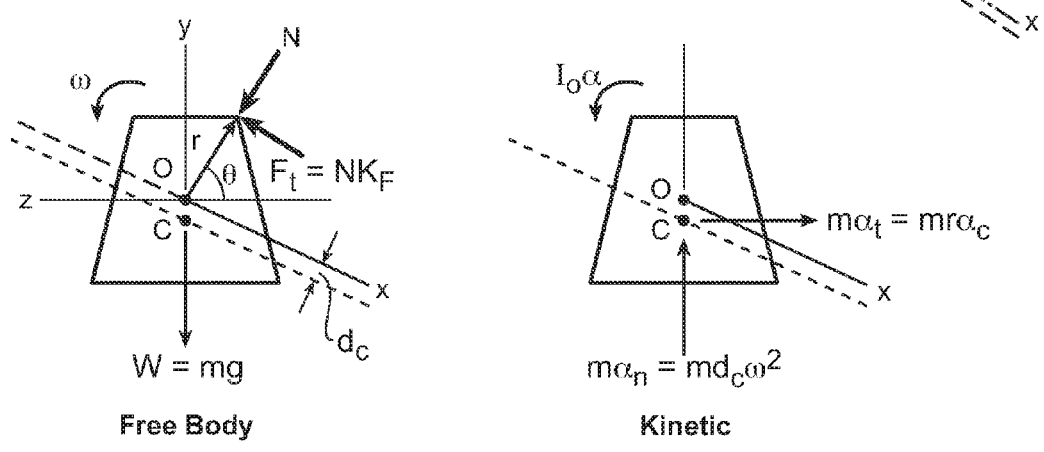
FIGS. 15A-15B show the cross sections of the instrument in FIG. 14.

Referring to FIG. 14, an exemplary shaft with a trapezoidal cross section has a centroidal axis that extends through C, which is parallel to the axis of rotation O, or the x-axis. Thus, the free body and kinetic diagrams are as shown in FIGS. 15A and 15B, respectively.

$$\Sigma M_o = F_f r_f - W d_c = N k_f r_f - m g d_c = I_o \alpha$$

$$\Sigma F_n = m a_n = m d_c \omega^2$$

$$\Sigma F_t = m a_t = m r a_c$$

Where
$\omega$=angular speed of rotation
N=Normal force exerted on the instrument by the root material
$k_f$=coefficient of friction of the material.
$F_f$=Force of friction=$Nk_f$
C=centroid of cross section, or center of mass.
O=center of rotation of longitudinal axis, or geometric center.
$d_c$=distance from center of rotation to the centroid
$\alpha$=angular acceleration of the cross section.
$a_r$=relative acceleration of the mass center of the instrument.
$a_c$=centripetal acceleration of the mass center of the instrument
g=acceleration due to gravity=32.2 ft/s$^2$
W=weight of the cross section=mg
$r_f$=distance from axis of rotation to application point of $F_f$.
Hence the moment equation and the vector form of the generalized Newton's second law of motion can be written:

$$\Sigma F = m a_r$$

$$\Sigma M_o = I \alpha$$

When observing the rotational dynamics of a rigid body in a laboratory setting, engineers can utilize the complete set of dynamic equations discussed above to predict the motion of the body. The engineers must have at their disposal at least as many dynamic equations as unknowns in order to solve for the desired resultants pertaining to the particular body in motion. Following this line of thought the engineer may apply known geometric relationships of a particular dynamic system to derive additional equations, which could be useful in solving for the desired results.

Thus radius of gyration $k_g$ of a mass about an axis for which the moment of inertia is I is defined by the equation $$k_g = (I/m)^{1/2}$$

Thus $k_g$ is a measure of the distribution of mass of a given body about the axis in question and its definition is analogous to the definition of the radius of gyration for area moments of inertia. If all the mass could be concentrated at a distance $k_g$ from the axis the correct moment of inertia would be $k_g^2 m$. The moment of inertia of a body about a particular axis is frequently indicated by specifying the mass of the body and the radius of gyration of the body about an axis. The moment of inertia is then calculated using the equation $$I = k_g^2 m$$

Furthermore, if the moment of inertia of a body is known about a centroidal axis it may be determined about any parallel axis. To prove this point consider the two parallel axis shown in FIG. 14, through C and the x-axis (axis of rotation). The radial distance from the two axes to any element of mass dm are $r_o$ and $r_i$ from FIGS. 15A, 15B, the separation of the axis is $d_c$. Thus, if one applies a moment equation directly about the axis of rotation $x_o$ $$\Sigma M = I_o \alpha$$

From the kinetic diagram one can obtain $\Sigma M_o$ very easily by evaluating the moment of the resultant about O, which becomes $$\Sigma M_o = I_o a + mar$$

This relationship is often referred to as the transfer of axis.

Figure 16A:
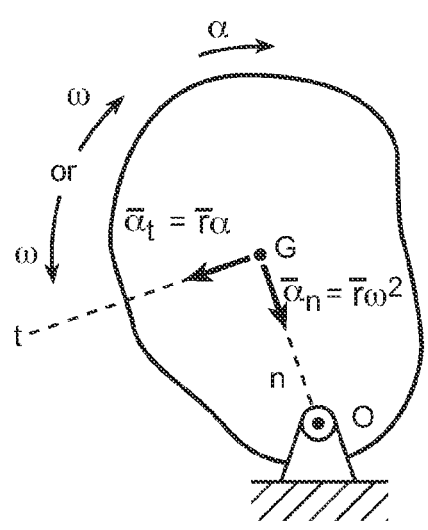
FIGS. 16A-16D show bodies with centers of mass different from their centers of rotation.
Figure 16B:
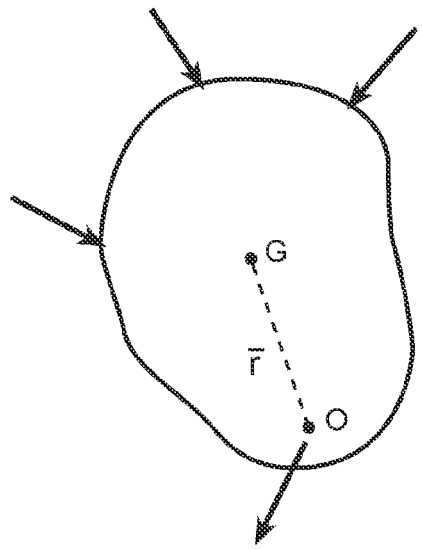
Figure 16C:
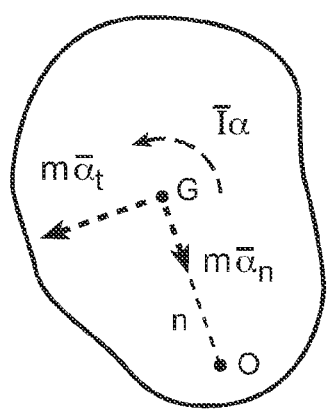

The acceleration components of the mass center for circular motion are more easily expressed in normal-tangential coordinates $$a_n = r\omega^2 \text{ and } a_t = ra_r,$$

which are the two scalar components of the force equation $\Sigma F = ma_r$, as shown in FIGS. 16A, 16B, 16C. In applying the moment equation about the mass center C it is essential to account for the moment of the force about the rotational axis O. Therefore by applying the transfer of axis relation for mass moments of inertia $I_o = I_r + mr_r^2$ gives us $$\tau M_o = (I_o - mr_r^2)a + mr_r^2 a = I_o a.$$

Figure 16D:
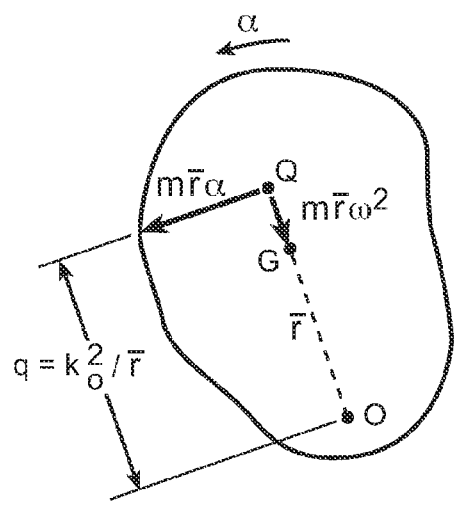

Thus one can combine the resultant force $ma_r$ and resultant couple $I_r a$ by moving the tangential component $ma_r$ to a parallel position through point Q, as shown in FIG. 16D. Point Q is located by $$mr_r aq = I_r a + mr_r a(r_r)$$

and by using the transfer of axis theorem and $I_o = k_o^2 m$ gives $q = k_o^2/z$. Point Q is called the center of percussion and has the unique property that the resultant of all forces applied to the body must pass through it. It follows that the sum of moments of all forces about the center of percussion is always zero.

$$\Sigma M_Q = 0$$

This principal can have practical use when analyzing the case of the endodontic instrument because it gives the engineer one more equations to utilize when solving for unknowns after measuring certain characteristics of its motion in the laboratory.

The swagger of an endodontic instrument can be approximated by making certain assumptions and by applying the stress and strain formulas for the bending of beams derived in the field of mechanical engineering called mechanics of materials. The most general case of a system of forces is one in which the forces are neither concurrent nor parallel. Such a system can always be replaced by a single resultant force acting at an arbitrary point and a resultant couple, or bending moment. It follows that by resolving the forces acting on the instrument at any instant by utilizing the dynamic equations described earlier, the resultant lateral force P and resultant couple M acting on the centroid of an arbitrary cross section can be obtained.

In this case, assume that the lateral loads act on a plane of symmetry. Since the y-axis is the plane of symmetry for an instrument with the singly symmetric trapezoidal cross section shown in FIG. 14, it is a principal axis. If the material is linearly elastic, then the neutral axis passes through the centroid C. Thus the y and z-axis are centroidal principal axes of the cross section. Under these conditions the normal bending stresses acting on the cross section vary linearly with the distance from the neutral axis and are calculated from the flexure formula, $\sigma = My/I$, whereby σ=stress=P/A P=Lateral load acting upon the cross section A=area of the cross section To better understand this principal, consider the trapezoidal body shown in FIG. 14. If in a laboratory setting a still photograph is taken of an instrument having this symmetry at any instant, a finite deflection in the segment can be observed. If one considers that one end is relatively fixed by the dental hand-piece, then geometric characteristics of the deflection can be measured. In this case the instrument will flex in a similar fashion, as would a cantilever beam subjected to a lateral load acting transversely to the longitudinal axis.

Here it should be noted that the majority of literature published about the subject of mechanics of materials was written for structural systems, but the same theory applies for the stress analysis of any object.

The load P acting a distance L from the fixed end will create internal actions or stress resultants in the form of shear forces and bending moments. Furthermore, after loading, the axis is bent into a curve that is known as the deflection curve of the beam.

For reference purposes, is constructed a system of coordinate axes with its origin at the support. The positive x-axis is directed along the longitudinal axis (i.e., across the page from left to right) and the y-axis is positive downward. The z-axis is directed inward (that is, away from the reader and into the page) so that the axes form a right-handed coordinate system.

The mechanical properties of materials used in most dental tools such as a flexible rotary instrument are determined by laboratory tests performed on small specimens of the material. After performing a tension or compression test of the material at various magnitudes of the load, a diagram of stress vs. strain can be prepared. Such a diagram is shown in FIG. 17.

Most structural materials have an initial region in the stress strain diagram in which the material behaves both elastically and linearly. The region is important in engineering because many machines are designed to function at low levels of stress in order to avoid permanent deformation from yielding. Linear elasticity is a property of many solid materials such as alloys of metal as is the case with nickel titanium from which many flexible endodontic instruments are constructed.

The linear relationship between stress and strain can be expressed by the equation $$\sigma = E\epsilon$$

in which $\epsilon$ is the strain and E is a constant of proportionality known as the modulus of elasticity. The modulus of elasticity is the slope of the stress strain diagram in the linearly elastic region and its value depends on the material being used. This relationship is known as Hooke's Law, named for the famous English scientist Robert Hooke (1635-1703). Hooke measured the stretching of long wires supporting weights and observed that the elongations were linearly proportional to the respective loads applied by each weight.

To obtain the general equations of the deflection curve for a prismatic beam (i.e. constant cross-sectional area along the length of the beam), consider the cantilever beam shown in FIG. 18A. One can place the origin of coordinates at the fixed end. Thus, the x-axis of the beam is directed positive to the right and the y-axis is directed positive downward. Here, assume that the xy plane is the plane of symmetry and the all loads act in this plane. It follows that the xy plane is the plane of bending. The deflection of the beam at any point $m_1$ at distance $x_1$ from the origin is the translation, or displacement of that point in the y-direction, measured form the x-axis to the deflection curve. When v is expressed as a function of x we have the equation of the curve.

The angle of rotation of the axis of the beam at any point $m_1$ is the angle between the x-axis and the tangent to the deflection curve. The angle is positive when clockwise, provided the x and y axes have the directions selected.

Now consider a second point $m_2$ at distance ds further along the deflection curve at distance x+dx from the origin. The deflection at this point is v+dv, where dv is the increment in deflection as we move from points $m_1$ to $m_2$. Also, the angle of rotation at $m_2$ is $\theta+d\theta$, where $d\theta$ is the increment in angle of rotation. At points $m_1$ and $m_2$, we can construct lines normal to the tangents to the deflection curve. The intersection of these normals locates the center of rotation $\rho$. From FIG. 18A we see that $\rho d\theta = dx$. Hence, the curvature k (equal to the reciprocal of the radius of curvature) is given by the following equation $k=1/\rho=d\theta/ds$ The sign convention selected for curvature is that the angle $\theta$ increases as we move along the beam in the positive x direction.

The slope of the deflection curve is the first derivative dv/dx, as we know from calculus. From the above equation we see that the slope is equal to the tangent of the angle of rotation $\theta$, because dx is infinitesimally small, then $dv/dx=\tan\theta$ or $v=\arctan(dv/dx)$ These relationships are based upon geometric considerations; thus they apply to a beam of any material.

Most beams undergo only small rotations, or torsion when they are loaded, hence their deflection curves are very flat with extremely small curvatures. Under these conditions, the angle $\theta$ is a very small quantity, thus we can make some approximations that simplify our work. This relationship holds true for the flexible rotary instrument because while the deflection curve is helical due to the rotation of the center of mass around the center of rotation, endodontic instruments are constructed with a material of such rigidity, as compared to the root material, that there is no binding within the root cavity. Hence the torsion about the axis of rotation, or the x-axis, is very small.

As can be seen from FIG. 18B $ds=dx/\cos\theta$ and since $\cos\theta \cong 1$, when $\theta$ is small, we obtain $ds \cong dx$ Therefore, the curvature becomes $k=1/\rho=d\theta/dx$ Thus for small torsional forces in the beam, the angle of rotation and the slope are equal. By taking the derivative of $\theta$ with respect to x, we get $k=1/\rho=d\theta/dx=d^2v/dx^2$ This formula relates the curvature k to the deflection v of the beam, and is valid for a beam of any material. If the material is linearly elastic, and follows Hooke's law, the curvature is $k=1/\rho=-M/EI$ in which M is the bending moment, and EI is the flexural rigidity of the beam. It follows that $d\theta/dx=d^2v/dx^2=-M/EI$ which is the differential equation of the deflection curve of a beam. This equation can be integrated in each particular case to find the angle of rotation $\theta$ or the deflection v.

For example, by differentiating the above equation with respect to x and then substituting the equations $q=-dV/dx$ and $V=dM/dx$ we obtain $d^3v/dx^3=-V/EI$ $d^4v/dx^4=q/EI$ where V is the shear force and q is the intensity of the distributed load. From this relationship and using prime notation, we can express the differential equations given above in the following forms $EIv''=-M$, $EIv'''=-V$ and $EIv''''=q$ From the derivations of these equations one can see that they are valid only when the material follows Hooke's law, and when the slopes of the deflection curve are very small. Also it should be noted the equations were derived considering the deflections due to pure bending and disregarding the shear deformations. These limitations are satisfactory for most practical purposes. It is known from calculus that the deflections can be obtained by integrating the shear force and load equations, as well as by integrating the equation for bending-moment, with the choice depending on the personal preference of the designer. Note also that the deflection of the rotary endodontic instrument would be comparable to the amplitude of the helical wave, which forms the deflection curve. This statement is important because it suggests a direct means to design rotary instruments with varying magnitudes of amplitude, thereby allowing us to "tailor" the instrument to fit a particular width of root cavity.

The differential equations of the deflection curve of the beam described above are linear equations, that is, all terms containing the deflection v and its derivatives are raised to the first power. As for a beam, they can be applied to the dental instrument in much the same manner. Therefore, solutions of the equations for various loading conditions may be superimposed. Thus, the deflections caused by several different loads acting simultaneously on the instrument can be found by superimposing the deflections caused the loads acting separately. This method for finding deflection is known as the principal of superposition.

For instance, if $v_1$ represents the deflection due to a couple and resultant moment $M_1$ and $v_2$ represents the deflection caused by a frictional force $F_f$, then the total deflection caused by $M_1$ and $F_f$ is $v_1+v_2$.

The methods described above for calculating deflections of a prismatic instrument can also be used to find deflections of a non-prismatic instrument. For a tapered instrument of variable symmetric or singly symmetric cross section, the bending theory described previously for a prismatic instrument gives satisfactory results provided the angle of taper is small.

The use of the differential equation for finding deflection is practical only if the number of equations to be solved is limited to one or two, and only if the integrations are easily performed. In the case of the tapered instrument, however, it may be difficult (or even impossible) to solve the differential equation mathematically. The reason is that the expression for the moment of inertial I as a function of length x is often complicated and produces a differential equation with a variable coefficient instead of constant coefficients. For the tapered instrument, therefore, the moment of inertia is variable along its length and the deflections cannot be found by exact mathematical analysis.

A close approximation, however, can be obtained which would predict the deflection of the instrument caused by implied forces upon it by using the principal of superposition, and by considering a "model" of the actual instrument made up of prismatic sections, with each consecutive section having smaller prismatic cross-sectional area. The total deflection of the actual tapered instrument, then, could be approximated by superimposing the deflections of each individual section of the model, whereby the cross sectional area of each prismatic section of the model mimics the cross sectional areas of the actual instrument at various locations along its length.

Figure 19:
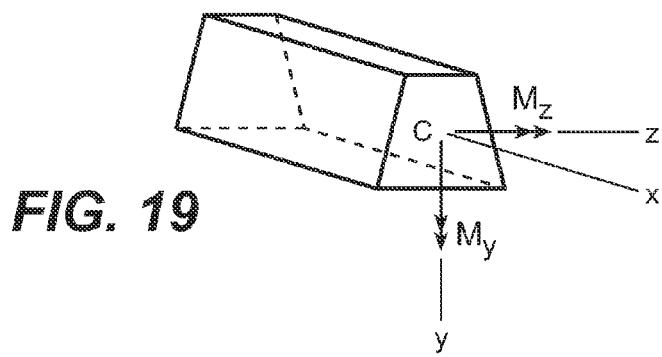
FIG. 19 shows a portion of an instrument.
Figure 20A:
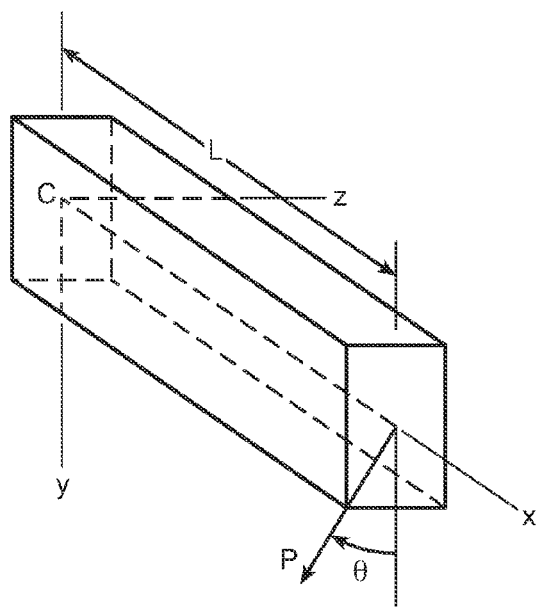
FIG. 20A-20D show a beam with various axes illustrated.
Figure 20B:
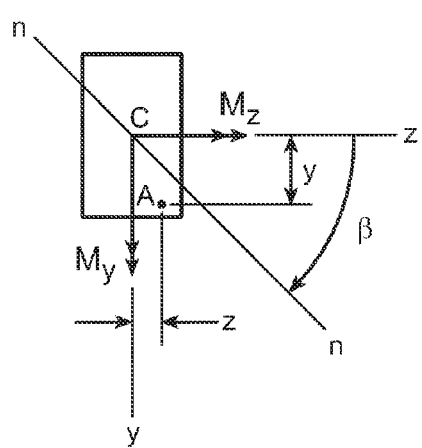
Figure 20C:
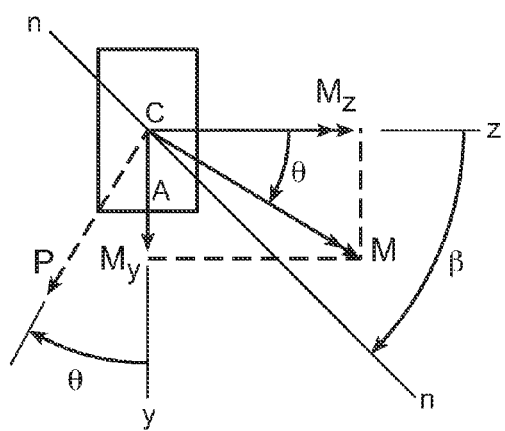
Figure 20D:
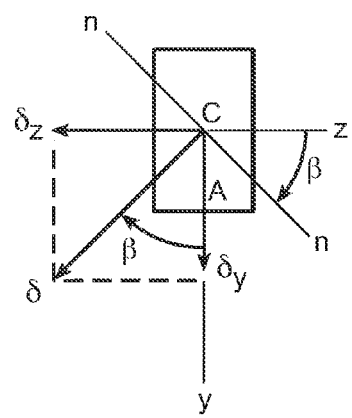

Returning to the discussion of normal bending stresses and flexure, the rotating endodontic instrument described earlier could experience bending about both principal axes of the cross section. Hence we need to establish a consistent sign convention for such moments. A segment of the instrument subjected to bending moments $M_x$ and $M_y$ acting on an arbitrarily selected cross section is shown in FIG. 19.

These moments are represented vectorially by double headed arrows and are taken as positive in the positive direction of the y and z-axis. When using the vectorial representation the right hand rule gives the sense of the moment (that is the direction of rotation of the moment). Note that the bending moments $M_y$ and $M_z$ act on the positive x face of the lamina. If the bending moments act on the negative x face of the lamina then their vectors are in the negative direction of the y and x-axis.

The simplest case of asymmetric bending arises when a doubly symmetric beam is subjected to loads acting in directions that are skew to the axes of symmetry. If the cross section of a beam is asymmetric, the analysis for bending becomes more complicated. Here, the case of a beam in bending is described for ease of exposition of procedures that can be applied to the case of the rotating endodontic instrument.

Assume that a beam having the cross section shown below is subjected to a bending moment M. Consider two perpendicular axes y and z in the plane of the cross section. The task is to determine what conditions must be met in order for these axes to be the neutral axes for bending under the action of the moment M, as shown in FIGS. 20A, 20B, 20C, 20D.

It is reasonable to assume that the beam is bent in such a manner so that the z-axis is the neutral axis. Then the xy plane is the plane of bending, and the beam deflects in that plane. The curvature of the bent beam is positive or negative according to the mathematical sign convention chosen. Thus, the normal stress acting on an element of area dA at distance y from the neutral axis is $$\sigma = -k_y E y$$

the minus sign is needed because positive curvature means that the part of the beam below the neutral axis is in compression. The force on the element of area is $\sigma_x dA$, and the resultant force is the integral of the elemental force taken over the entire cross-sectional area. Since we are considering pure bending, the resultant force must be zero, thus, $$\int \sigma_x dA = -k_y E \int y dA = 0$$

This equation shows that the neutral axis (the z-axis) must pass through the centroid C of the cross section. As an alternative, we could have assumed that the y-axis was the neutral axis, in which case the xz axis is the plane of bending.

Now consider the moment resultant of the stress $\sigma_x$ and assume that bending takes place about the z-axis as the neutral axis, in which case the stress $\sigma_x$ is obtained from the above equation. Then the bending stresses about the y and z-axes are $$M_z = -\int \sigma_x y dA = -k_z E \int y^2 dA = -k_z E I_z$$

$$M_y = -\int \sigma_x z dA = -k_z E \int yz dA = -k_z E I_{yz}$$

in which $I_{yz}$ is the product of inertia of the cross-sectional area with respect to the y and z-axes. From these equations, certain conclusions can be drawn. If the z-axis is selected in an arbitrary direction through the centroid, it will be the neutral axis only if there are moments $M_y$ and $M_z$ acting about both the y and z axes and only if the moments are in the ratio established by the equation above. However, if the z-axis is a principal axis, then $I_{yz}=0$ and the only moment acting is $M_z$. In that event, we have bending in the xy plane with the moment $M_z$ acting in that same plane. In other words, bending takes place in the same manner as for a symmetric beam. Similar conclusions can be made under the assumption that the y-axis is the neutral axis.

Thus, the following important conclusion can be drawn. When an asymmetric beam is in pure bending, the plane of the bending moment is perpendicular to the neutral axis only if the y and z-axes are principal centroidal axes of the cross section. Then, if a bending moment acts in one of the principal planes, this plane will be the plane of bending (perpendicular to the plane of bending) and the usual bending theory is valid. The preceding conclusion suggests a direct method for analyzing an asymmetric beam subjected to any bending moment M. One can begin by locating the principal centroidal axes y and z. Then the applied couple M is resolved into components $M_y$ and $M_z$, assumed to be positive in the directions shown in FIGS. 20A, 20B, 20C, 20D. These components are $M_y =$ $$M \sin \theta \text{ and } M_z = M \cos \theta$$

where $\theta$ is the angle between the vector M and the z-axis. Each of these components acts in a principal plane and produces pure bending in that same plane. Thus, the usual stress and deflection formulas for pure bending apply. The stresses and deflections obtained from $M_y$ and $M_z$ acting separately may be superimposed to obtain the corresponding quantities due to the original bending moment M. For instance, the resultant bending stress at any point A in the cross section is $$\sigma_x = M_y z / I_y - M_z y / I_z$$

or;

$$\sigma_x = (M \sin \theta) z / I_y - (M \sin \theta) y / I_z$$

in which y and z are the coordinates of point A. The equation of the neutral axis nn is obtained by setting $\sigma_x$ equal to zero $$\sin \theta (z/I_y) - \sin \theta (y/I_z) = 0$$

The angle $\beta$ between this line and the z-axis is obtained as follows $$\tan \beta = y/z = I_y/I_z \tan \beta$$

This equation shows that in general the angles $\theta$ and $\beta$ are not equal, hence the neutral axis is not perpendicular to the plane in which the applied couple M acts.

The deflection produced by the bending couples $M_y$ and $M_z$ can be obtained from the usual deflection formulas. These deflections take place in the principal planes and can be superimposed to obtain resultant deflections, which lie in the plane that is normal to the neutral axis nn.

The preceding discussions present an arsenal of analytical tools which could be utilized to predict the dynamic performance of a rotating endodontic instrument irregardless of its cross sectional geometry. These same principals can be used to predict the swagger, or bending and resultant deflections, which occur when the center of mass of the instrument is offset away from the axis of rotation. By applying these procedures, the designer could tailor the instrument to cut in typically hard to reach areas of the canal. Such an example of a procedure is as follows.

1. Conceptualize an instrument with a cross sectional geometry that has an offset center of mass. The geometry in consideration should be singly symmetric.

2. Draw free body and kinetic diagrams of the cross section, or lamina, taking into consideration the moment and frictional forces, which apply to the particular geometry.

3. Resolve the forces acting upon the lamina into a single resultant force and resultant couple.

4. Determine the stress and bending moments of the section which result from the forces applied.

5. Develop a prismatic "model" of the instrument, which mimics the geometrical dimensions of the actual tapered instrument.

6. Calculate the deflection curve for each section of the model acted upon by the implied forces.

7. Write the differential equations, which apply to the particular deflection curve in consideration.

8. Integrate the deferential equation along the length of each section to calculate its deflection. Note that this can be done for the shear and force equations, as well as for the bending moment equations, depending upon the personal preference of the designer.

9. Superimpose the deflections for each section, to obtain a close approximation of the deflection of the actual instrument.

10. Repeat the procedure for various cross sections until the desired deflection is obtained (e.g. to deflect within the confines of a particular width of root cavity).

Equilateral Swagger

Instruments fabricated from flexible materials that are sufficiently asymmetrical (when viewed in transverse cross-section) can swagger, particularly at their tip ends. Some of these instruments include flutes that are variable in depth and/or spaced apart unevenly (i.e., for a given transverse cross section, the angles between the flutes are not the same). Such instruments maintain the same transverse cross sectional geometry along the axis of rotation, and the spacing between the flutes, thus, does not change along the axis of rotation (although the flutes are uneven). The flutes, in such a case, are described in the instant specification as being parallel.

Although an instrument configured as described above can swagger, the swagger is typically uneven about the axis of rotation. That is, the extent to which the instrument swings away from the axis of rotation is different for different angles of rotation. In essence, the swing of the instrument is not symmetrical about the axis of rotation.

A flexible endodontic instrument can be designed to swagger so that its swing is symmetrical or approximately symmetrical about the axis of rotation. That is, the swagger is equilateral or approximately equilateral. The swagger can be at least the same distance from the axis of rotation at two angular locations that are 180° apart. In some implementations, equilateral swagger is a result of a superflexible body having a least portion with a center of mass located away from the body's axis of rotation being bound at a tip end while rotating. That is, when the instrument is within an ECS and caused to rotate, the instrument forms helical waves within the canal. The number of waves can vary based on the configuration of the instrument, forming 0.5, 1, 2, 3, 4, 5, 6, 7, 8, 9, 10 or more sinusoidal waves within the canal.

When an instrument capable of swagger is rotated within the ECS, the portions of the instrument that swagger contact one wall of the ECS at a time. Conversely, in conventional rotary instruments, the instrument is used in such a way that all walls of the ECS are cleaned simultaneously. While instruments described herein are described as being capable of equilaterally swaggering, it should be understood that the instruments are meant to attempt to equilaterally swagger. Thus, the instruments may have portions that approximate equilateral swagger and may not achieve perfect equilateral swagger under any or all conditions.

Equilaterial swagger can be caused by a number of different instrument configurations. In some implementations, the instrument, when viewed in transverse cross-section, begins at the shank end as cross-sectionally symmetrical and gradually becomes asymmetrical as it progresses toward the tip end. The asymmetrical portion will swagger during use. Because a NiTi instrument is flexible and is able to change phase from martensite to austenite when under pressure, the symmetrical portion of the instrument may also begin to swagger. Instruments formed of other materials can also induce swagger in non-asymmetrical portions during rotation. In other implementations, the instrument, when viewed in transverse cross-section, begins at the shank end as cross-sectionally symmetrical, but becomes asymmetrical and takes on a new geometry as it moves toward the tip end. For example, the instrument may have a square cross-section at the shank end and a triangular cross-section at the tip end. The change in symmetry or geometry occurs in an area overlapping a cutting surface.

In other implementations, the instrument has a "canted" axis of rotation or centroid. That is, the axis of rotation is not parallel to a line along which centroids of the instrument lie. The axis of rotation and the line along which the centroids lie can intersect and be at an angle to one another. The canted instrument can be linear, or can be curved.

Moreover, some of the configurations described below allow the instrument to have equilateral swagger at a portion for cutting a curved portion of the ECS, including the fulcrum (the point of greatest curvature). The instrument can evenly cut the inner and outer wall of the ECS at the fulcrum. In general, an instrument can be configured to have equilateral swagger at any point along the working portion of its shaft. Such a feature is advantageous as the curvature of the canal can and typically does deviate in a mesial-distal or sagital plane and in the bucco-lingual or coronal plane. In addition, the curvature of the canal is quite variable, usually increasing slowly and then more rapidly as one approaches the apical portion of the preparation. These changes in curvature are rarely linear.

Implementations

FIGS. 21A-21E illustrate one implementation of an endodontic instrument described herein. The endodontic instrument 110 includes three sides, is triangular in transverse cross-section, and can be utilized to remove tissue and/or dentin from an ECS. The instrument 110 includes a shank 1111 and a working portion 1112, which is tapered in a shank to tip direction. The tip 1113 includes an active or cutting surface, which is confluent with the working surface 1112 (for example, like the tip shown in FIGS. 22A-22D). Alternatively, the leading tip 1113 (of the instrument shown in FIGS. 21A-21E) can include a non-active or non-cutting surface, which is also confluent with the working surface 1112 (for example, like the tip shown in FIG. 9C). The MxFD 1117 is located near the shank end of the cutting surface and MnFD 1116 is located near the tip 1113. The shank 1111 above the working portion 1112 is essentially cylindrical and exhibits a slightly smaller diameter than the cutting surface at the MxFD. The instrument 110 includes rolled edge portion 114, which is confluent with the working portion 1112. This rolled edge modification is illustrated in FIGS. 9A-9D. A fitting 1115, which is suitable for an engine driven motor with a hand-piece and chuck, or a handle utilized for manual instrumentation, is attached to the shank 1111.

As shown in FIGS. 21A-21E, three continuous helical flutes 1120A, 1120B and 1120C are substantially concave grooves which follow the circumference of the working surface 1112 spiraling toward the leading tip 1113 forming concentric circles. These flutes may be equidistant from each other or become increasingly tighter or more numerous as they approach the tip. The total number of flutes from MxFD to the MnFD should be no fewer than 16 but not greater than 24. Helical flutes 1120A, 1120B and 1120 C each originate at the MxFD at separate locations that are equally spaced apart around the circumference of the shank 1111 or more specifically at 120° of separation. Each helical structure (i.e., the mass between the flutes) is continuous along the length of the cutting surface 1112 to the leading tip 1113.

Figures 21A, 21B, 21C:
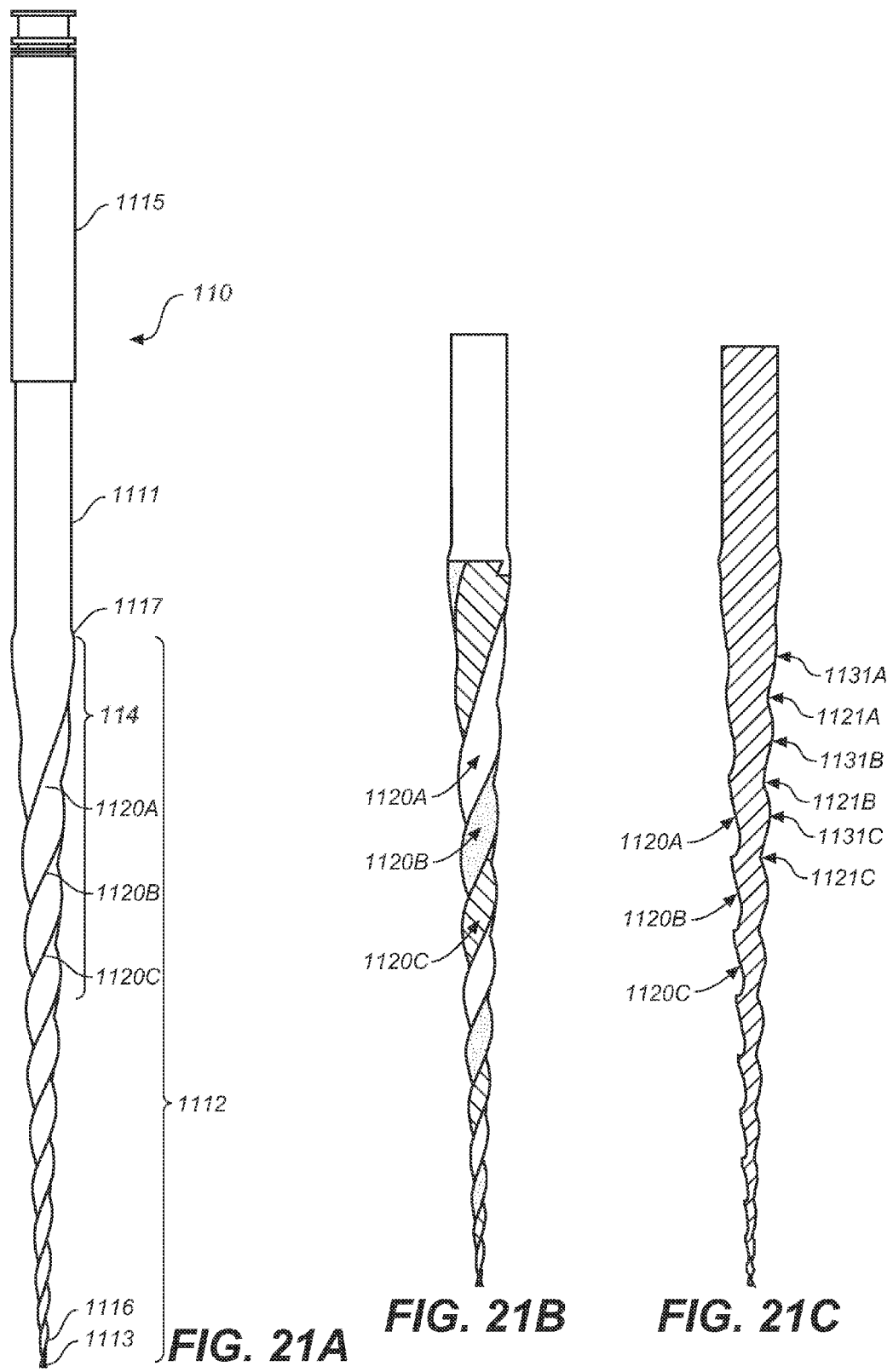
FIGS. 21A-21E show one implementation of an endodontic instrument.
Figure 21D:
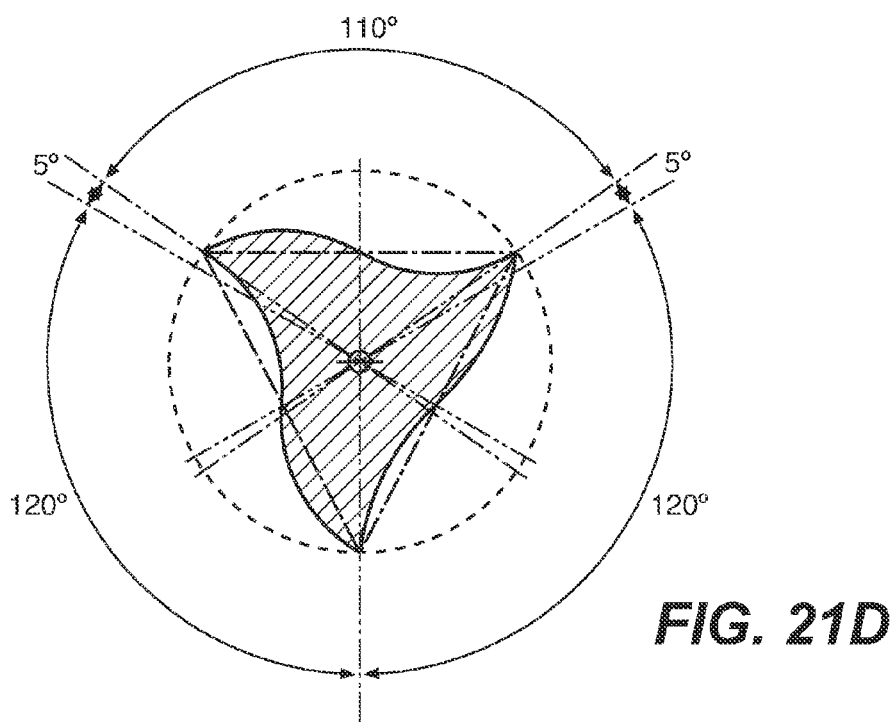
Figure 21E:
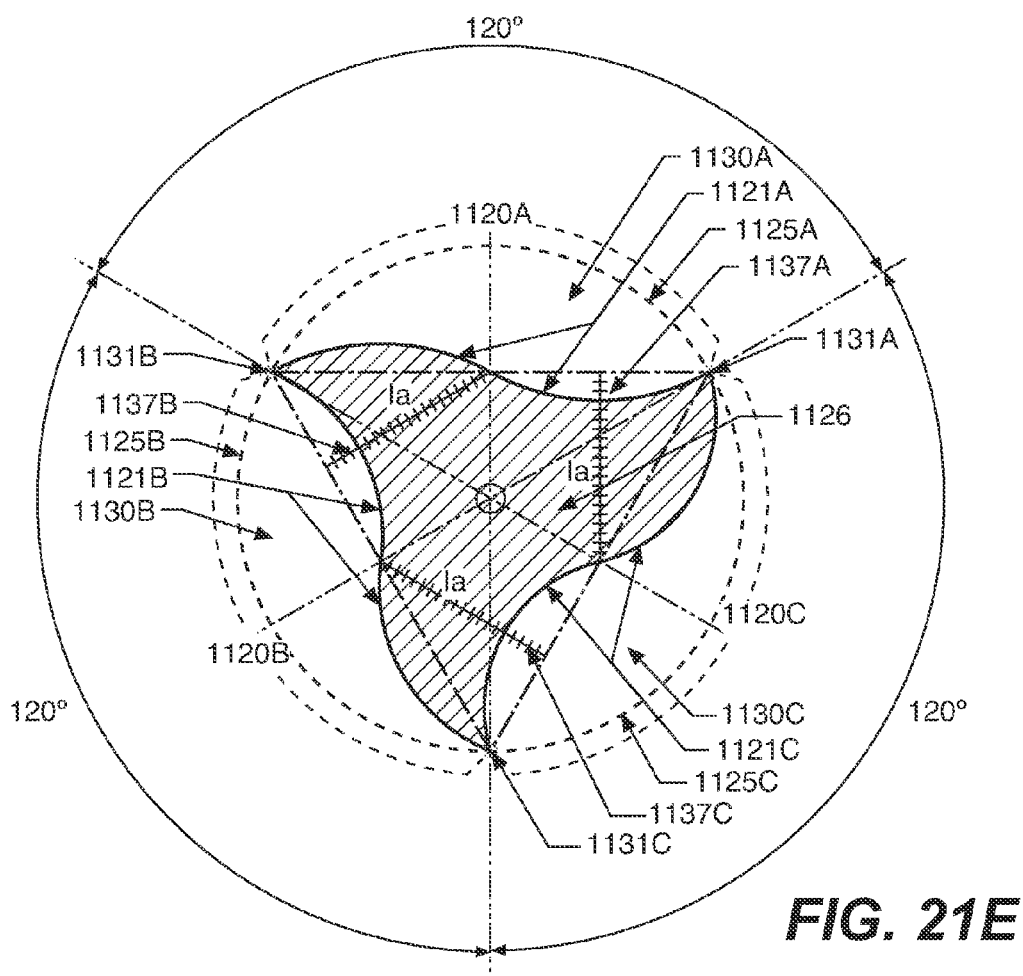
Figure 22A:
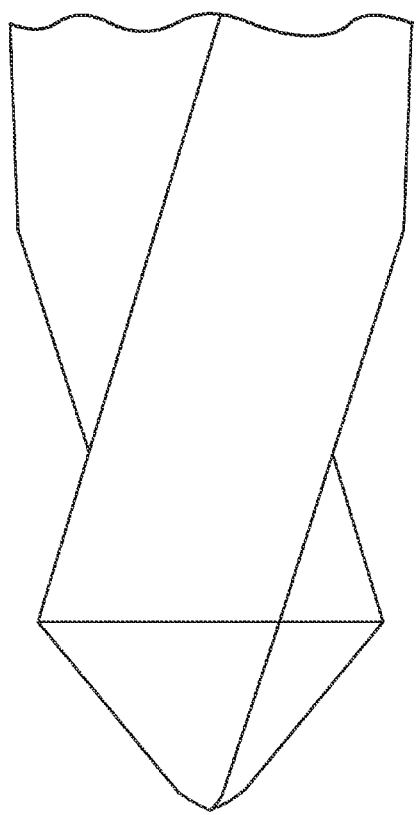
FIGS. 22A-22D show an endodontic instrument that includes a cutting tip.
Figure 22D:
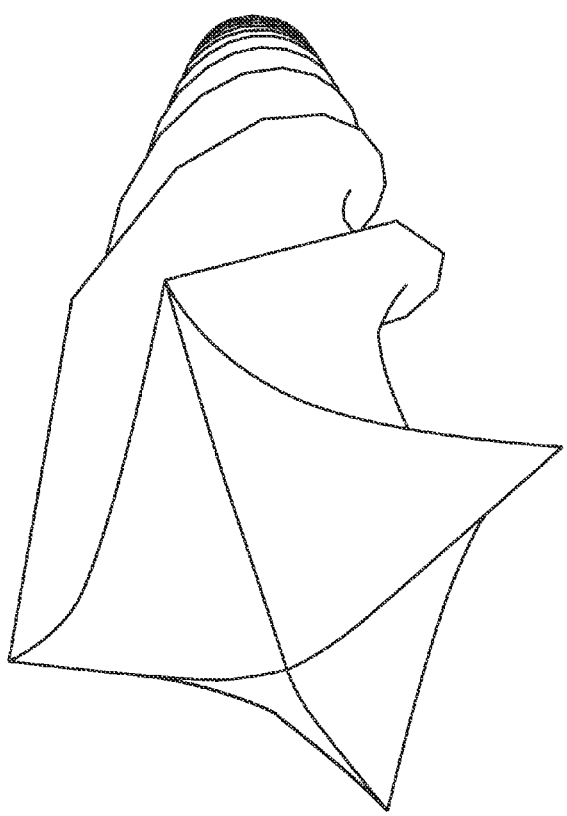
Figure 22B:
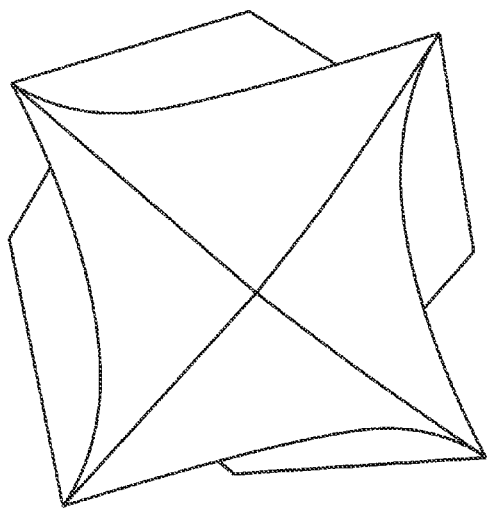
Figure 22C:
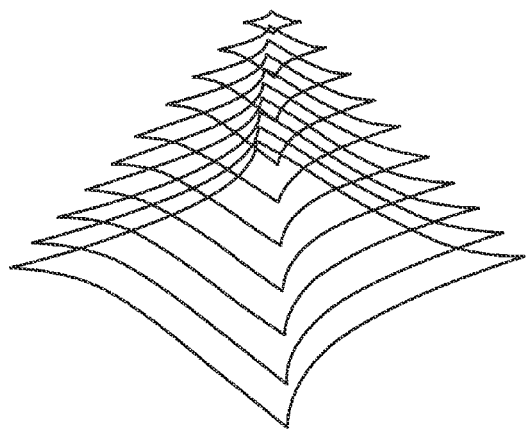

With reference to FIG. 21E, it can be seen that flutes 1120A, 1120B and 1120C have S shaped splines 1121A, 1121B and 1121C. The flutes 1120A, 1120B and 1120C form helical cutting edges 1125A, 1125B and 1125C at the periphery of the shank 1111. A transverse cross-section is shown of the cutting portion 1112. The helical flutes 1120A, 1120B and 1120C cooperate to form a web or core 1126, which is essentially triangular. Areas of radial clearance or cutouts created by the flutes 1121A, 1121B and 1121C outline the web or core. These areas of clearance are designated by numerals 1130A, 1130B and 1130C. In transverse cross-section of the shank 1111, splines 1121A, 1121B, and 1121C of cutting flutes 1120A, 1120B, and 1120C form teardrop shaped clearance areas of variable depth. The cutting surfaces 1125A, 1125B, and 1125C, or the perimeter of the shank, and the splines of the inner walls 1121A, 1121B, and 1121C circumscribe clearance areas 1130A, 1130B, and 1130C.

With further reference to FIG. 21E, it can be seen that walls 1121A, 1121B, and 1121C intersect the periphery of the shank 1111 at points 1131A, 1131B, and 1131C. These intersections are equal distances apart or at 120° of separation forming a neutral cutting angle (90° angle to the tangent of the perimeter of shank 1111) or slightly positive rake angle (greater than 90° to the tangent of the perimeter of the shank 1111). Lines drawn connecting point 1131A, 1131B, and 1131C form an equilateral triangle. As shown in FIG. 21D, points 1131A, 1131B, and 1131C intersect the periphery of the shank 1111 alternately at 110°, 125°, and 125° of separation. Lines drawn connecting the point 1131A, 1131B, and 1131C form an isosceles triangle. The outline of the triangle that is formed connecting point 1131A, 1131B, and 1131C can vary. The outline may also be a scalene triangle with unequal sides. The difference in the number of degrees of separation between the longest spline and the short spline is not less than 60° and not greater than 150°.

The splines 1121A, 1121B, and 1121C are S-shaped and are individually symmetrical. The bisector of each spline divides the spline equally into convex and a concave segments which form the S-shaped curve. The lines that bisect each spline can be drawn to the center of the core 1126 and are equal in length. Further, an alternate bisector a can be drawn from the center of each spline through the greatest concavity the adjacent spline and perpendicular to the lines, which form the equilateral triangle. The bisectors for each spline 1121A, 1121B, and 1121C are equal.

The greatest depth of each spline can be defined by a segment of a. These depths can vary and, furthermore, be calculated as a percentage of the length of a. The greatest depths of splines 1121A, 1121C, and 1121B, indicated with demarcated line segments 1137A, 1137B, and 1137C, are 15%, 20%, and 25% of the length of a, respectively. The greatest convexities of splines 1121A, 1121B, and 1121C are mirror images of the greatest concavities of the same splines. The depth and height of each spline can vary; however, the cross sectional diameter of the core portion 1126 should generally not be narrower than approximately half or fifty percent of the cross sectional diameter of the shank of the instrument.

FIGS. 23A-23D illustrate another implementation, which is four sided or rectilinear in transverse cross-section and can be utilized to remove tissue and/or dentin from an ECS. The implementation shown includes a shank similar to the one described in FIGS. 21A-21E and a working portion 1212, which is tapered in a shank to tip direction. The tip 1213 can include a cutting surface, which is confluent the working surface 1212 (for example, like the tip shown in FIGS. 22A-22D). Alternatively, the leading tip 1213 (of the instrument shown in FIGS. 23A-23D) can include a non-cutting surface, which is confluent with the working surface 1212 (for example, like the tip shown in FIG. 9C). The MxFD 1217 is located near the shank end of the cutting surface and MnFD 1216 is located near the tip end of the cutting surface. The shank 1211 above the cutting surface 1212 is essentially cylindrical exhibiting a slightly smaller diameter than the cutting surface at the MxFD (also similar to the instrument described in FIGS. 21A-21E). The instrument can include a modified or rolled edge portion 1214, which can to be confluent with the cutting surface 1212. This rolled edge feature is illustrated in FIGS. 9A-9D. A fitting, which is suitable for an engine driven motor with a hand-piece and chuck or a handle utilized for manual instrumentation, is attached to the shank at its most proximal end (also similar to the fitting described in FIGS. 21A-21E).

With further reference to FIGS. 23A-23D, four continuous helical flutes 1220A, 1220B, 1220C, and 1220D are substantially concave grooves which follow the circumference of the working surface 1212 spiraling toward the leading tip 1213 forming concentric circles, which may be equidistant from each other or becoming increasingly tighter or more numerous as they approach the tip 1213. The total number of flutes from MxFD to the MnFD should be no fewer than 16 but not greater than 24. Helical flutes 1220A, 1220B, 1220C, and 1220D each originate at the MxFD at separate locations that are equally spaced apart around the circumference of the shank 1211 or more specifically at 90° of separation. Each flute is continuous along the length of the cutting surface 1212 to the leading tip 1213.

Figure 23A:
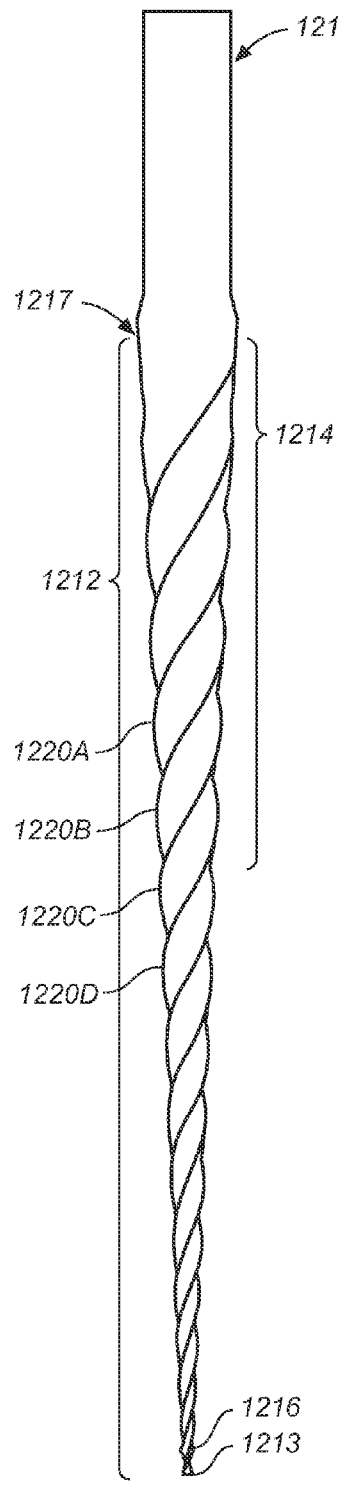
FIGS. 23A-23D show another implementation of an endodontic instrument.
Figure 23B:
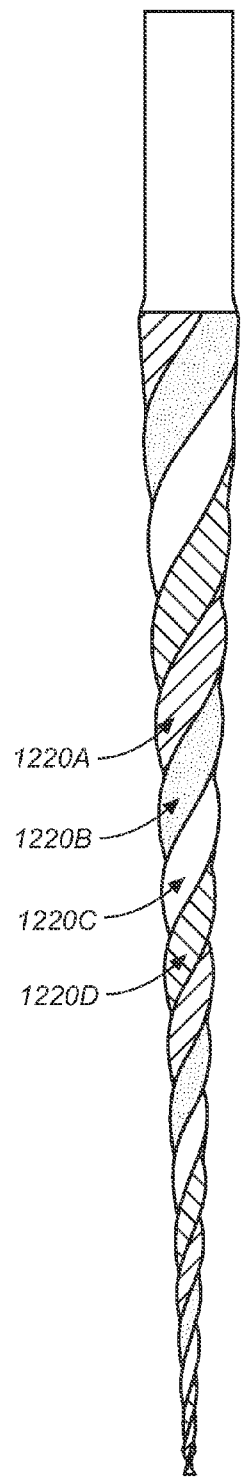
Figure 23C:
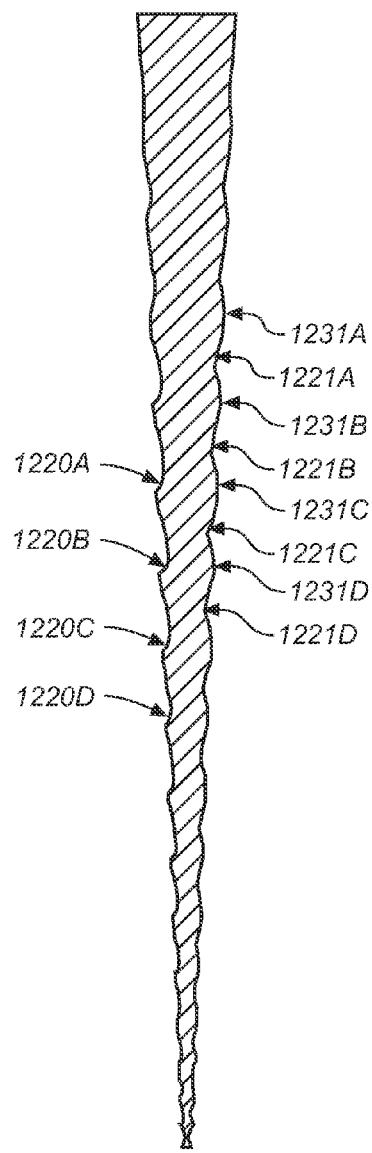
Figure 23D:
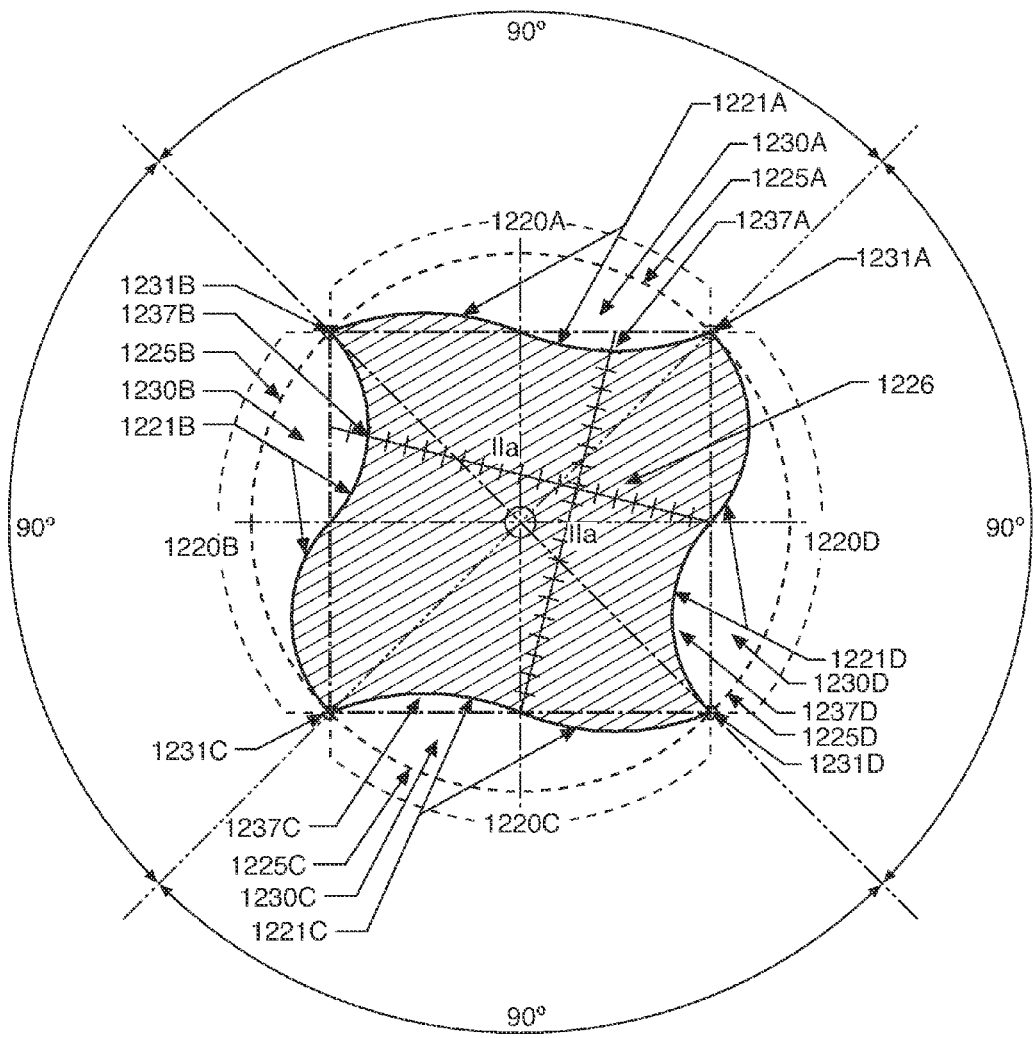

With reference to FIG. 23D, it can be seen that flutes 1220A, 1220B, 1220C, and 1220D have an S-shaped splines 1221A, 1221B, 1221C, and 1221D. The flutes 1220A, 1220B, 1220C, and 1220D form helical cutting edges 1225A, 1225B, 1225C, and 1225D at the periphery of the shank 1211. With reference to FIG. 23D, a transverse cross-section is shown of the cutting portion 1212. The helical flutes 1220A, 1220B, 1220C, and 1220D cooperate to form a web or core 1226, which is generally square shaped. The web or core is outlined by areas of radial clearance or cut outs created by splines 1221A, 1221B, 1221C, and 1221D. These areas of clearance are designated by numerals 1230A, 1230B, 1230C and 1230D. In transverse cross section of the shank, splines 1221A, 1221B, 1221C, and 1221D of cutting flutes 1220A, 1220B, 1220C, and 1220D form teardrop clearance areas of variable depth. Clearance areas 1230A, 1230B, 1230C, and 1230D are circumscribed by cutting edges 1225A, 1225B, 1225C, and 1225D, or the perimeter of the shank, and the splines of the inner walls 1221A, 1221B, 1221C, and 1221D.

With further reference to FIG. 23D, it can be seen that splines 1221A, 1221B, 1221C, and 1221D intersect the periphery of the shank 1211 at point 1231A, 1231B, 1231C, and 1231D, respectively. These intersections are equal distances apart or at 90° of separation, forming a neutral angles (90° angle to the tangent of the perimeter of shank 1211) or slightly positive rake angles (greater than 90° to the tangent of the perimeter of the shank 1211). Lines drawn connecting point 1231A, 1231B, 1231C, and 1231D form a square.

The splines 1221A, 1221B, 1221C, and 1221D are S-shaped and are individually symmetrical. The bisector of each spline divides the spline equally into convex and a concave segments which form the S-shaped curve. The lines that bisect each spline can be drawn to the center of the core 1226 and are equal in length. Further, an alternate bisector a can be drawn from the center of each spline through the greatest concavity the opposite spline and is also equal in length.

The greatest depth of each spline can be defined by a segment of a. These depths can vary and, furthermore, be calculated as a percentage of the length of a. The greatest depths of splines 1221A and 1221C, indicated with demarcated line segments 1237A and 1237C, are 5% of the length of a. The greatest depth of splines 1221B and 1221D, indicated with line segments 1237B and 1237D, are 25% of a. The greatest convexities of splines 1221A, 1221B, 1221C, and 1221D are mirror images of the greatest concavities of the same splines. The depth and height of each spline can vary; however, the cross sectional diameter of the core portion 1226 should generally not be narrower than approximately half or fifty percent of the cross sectional diameter of the shank of the instrument.

FIGS. 24A-24E illustrate another implementation, which is four sided or rectagonal in transverse cross-section and can be utilized to remove tissue and/or dentin from an ECS. The instrument includes a shank 311 similar to the one described above with respect to FIGS. 21A-21E and a working portion 312, which is tapered in a shank to tip direction. The tip 313 can include a cutting surface, which is confluent the working surface 312 (for example, like the tip shown in FIGS. 22A-22D). Alternatively, the tip 313 can display a non-cutting surface, which is confluent with the working portion 312 (for example, like the tip shown in FIG. 9C). The instrument includes an MxFD 317 and an MnFD 316. The shank 311 above the above the working portion 312 is essentially cylindrical exhibiting a slightly smaller diameter than the cutting surface at the MxFD. The shank here is similar to the one described in FIGS. 21A-21E. The instrument includes a modified or rolled edge portion 314, which is confluent with the cutting surface 312. This rolled edge feature is illustrated in FIGS. 9A-9D. A fitting, which is suitable for an engine driven motor with a hand-piece and chuck or a handle utilized for manual instrumentation, is attached to the shank at its most proximal end also similar to the fitting described in FIGS. 21A-21E.

As shown in FIGS. 24A-24E, four continuous flutes 320A, 320B, 320C and 320D are substantially concave grooves, which follow the circumference of the working surface 312 spiraling toward the leading tip 313 forming concentric circles, which may be equidistant or become increasingly tighter or more numerous as they approach the tip. The total number of flutes from MxFD to the MnFD should be no fewer than 16 but not greater than 24. Flutes 320A, 320B, 320C, and 320D each originate at the MxFD at various locations spaced around the circumference of the shank, more specifically at 80°, 100°, 80°, and 100° of separation, respectively. Each flute is continuous along the length of the cutting surface 312 to the leading tip 313.

Figure 24A:
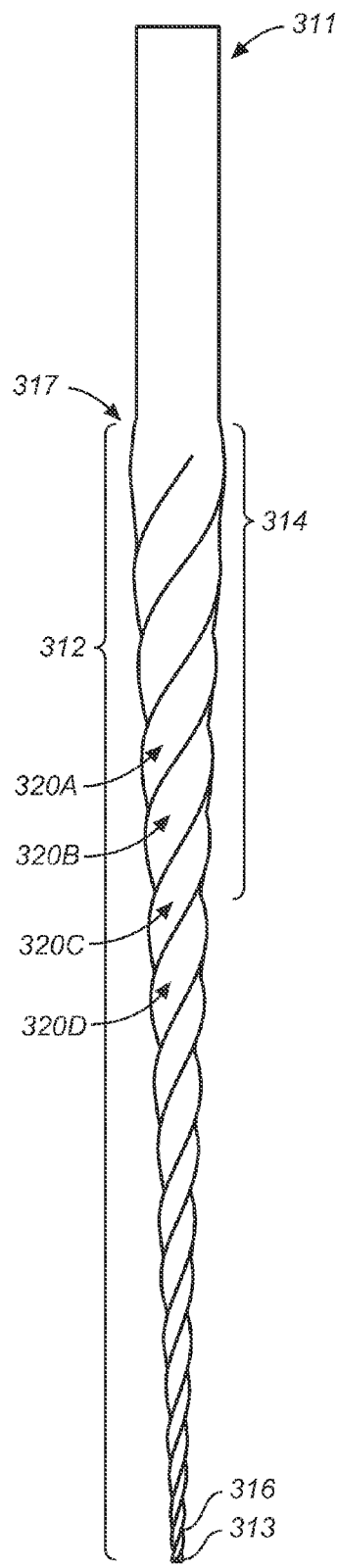
FIGS. 24A-24E show another implementation of an endodontic instrument.
Figure 24B:
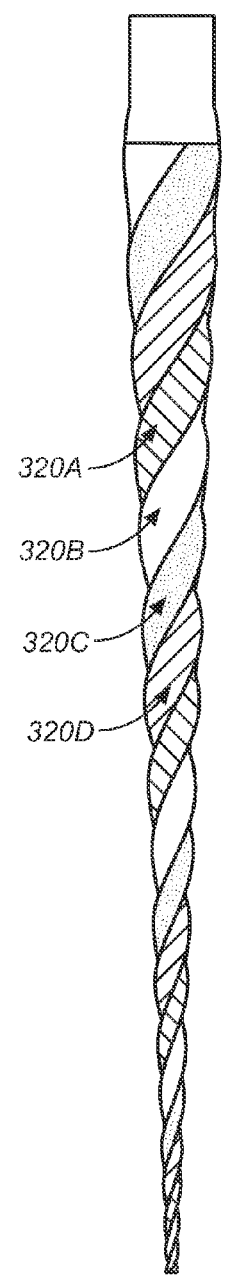
Figure 24C:
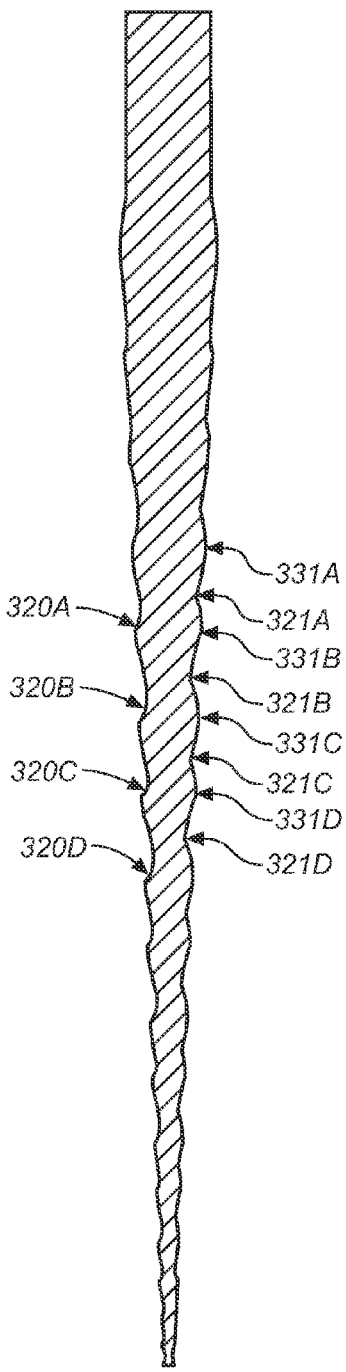
Figure 24D:
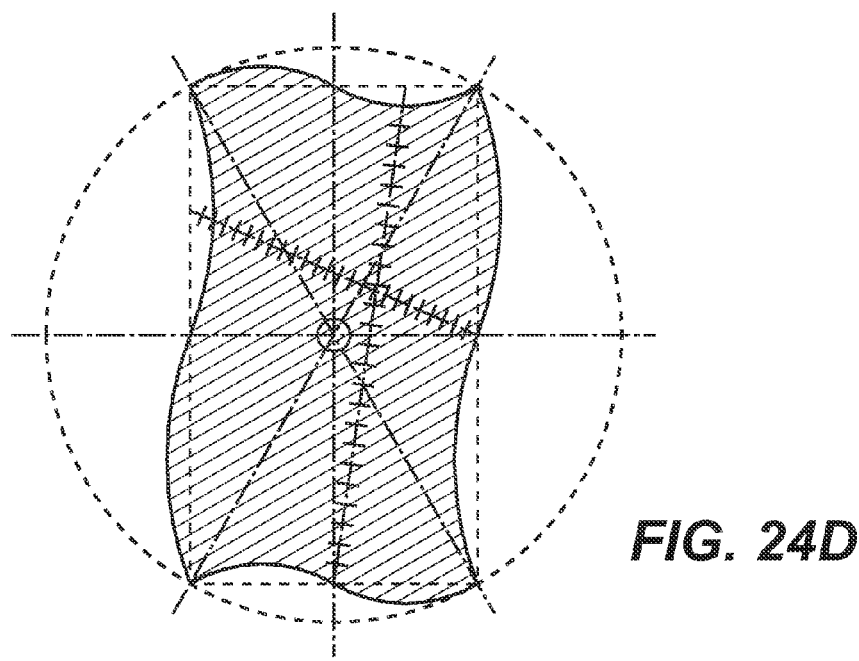
Figure 24E:
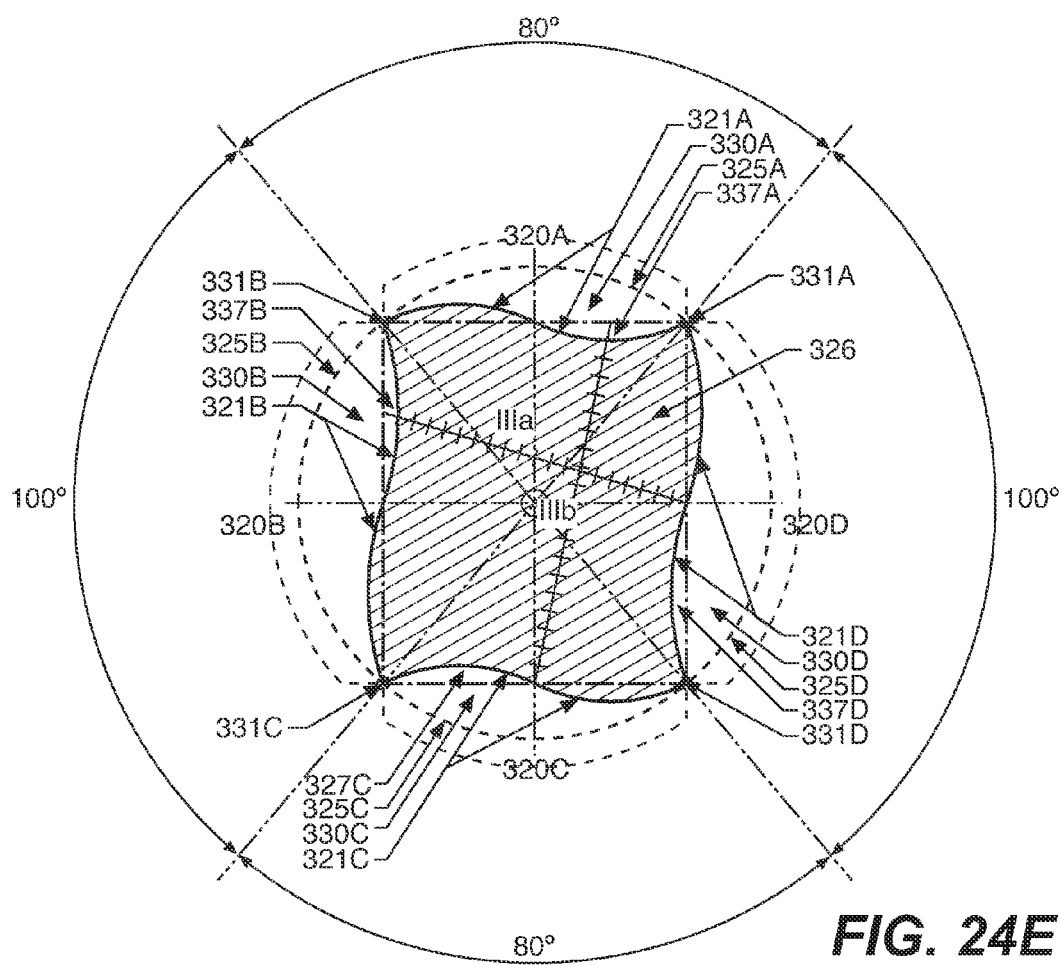

With reference to FIG. 24E, it can be seen that flutes 320A, 320B, 320C, and 320D have an S-shaped splines 321A, 321B, 321C, and 321D. The flutes 320A, 320B, 320C, and 320D form helical cutting edges 325A, 325B, 325C, and 325D at the periphery of the shank 311. As shown in FIG. 24E, a transverse cross-section is shown of the cutting portion 312.

The flutes 320A, 320B, 320C, and 320D cooperate to form a web or core 326, which is essentially rectagonally shaped. The web or core is outlined by areas of radial clearance or cut outs created by the splines 321A, 321B, 321C, and 321D. These areas of clearance are designated by numerals 330A, 330B, 330C, and 330D. In transverse cross section of the shank, the splines 321A, 321B, 321C, and 321D of flutes 320A, 320B, 320C, and 320D form teardrop clearance areas of variable depth. Clearance areas 330A, 330B, 330C, and 330D are circumscribed by cutting edges 325A, 325B, 325C, and 325D, or the perimeter of the shank, and the splines 321A, 321B, 321C, and 321D.

As shown in FIG. 24E, it can be seen that splines 321A, 321B, 321C, and 321D intersects the periphery of the shank 311 at points 331A, 331B, 331C, and 331D, respectively. These intersections are at 80°, 100°, 80°, and 100° of separation, respectively, forming neutral or slightly positive rake angles. Lines drawn connecting point 331A, 331B, 331C, and 331D form a rectangle. The difference in degrees between the longest spline and the shortest spline is 20°. Alternatively, as shown in FIG. 24D, points 331A, 331B, 331C, and 331D can intersect the periphery of the shank at 90°, 95°, 80° and 95° of separation, respectively. Lines drawn connecting the point 331A, 331B, 331C, and 331D also form a rectangle. The outline of the trapezoid that is formed connecting point 331A, 331B, 331C, and 331D can vary. The difference in the number of degrees of separation between the longest spline and the short spline should not be less than 5° and not greater than 70°.

The splines 321A, 321B, 321C, and 321D are S-shaped and are individually symmetrical. The bisector of each spline divides the spline equally into convex and a concave segments which form the S-shaped curve. Alternate bisectors a and b can be drawn from the center of each spline through the greatest concavity the opposite spline.

The greatest depth of each spline can be defined segments of a and b. These depths can vary and, furthermore, be calculated as a percentage of the length of a and b. The greatest depths of splines 321A and 321C, indicated with demarcated line segments 337A and 337C, are 5% of the length of a. The greatest depth 321B and 321D, indicated with demarcated line segments 337B and 337D, are 5% of b. The greatest convexities of splines 321A, 321B, 321C, and 321D are mirror images of the greatest concavities of the same splines. The depth and height of each spline can vary; however, the cross sectional diameter of the core portion 326 should generally not be narrower than half or fifty percent of the cross sectional diameter of the shank of the instrument.

FIGS. 25A-25E illustrate another implementation, which is four sided and trapezoidal in transverse cross-section and can be utilized to remove tissue and/or dentin from an ECS. The instrument includes a shank 411 similar to the one described above with respect to FIGS. 21A-21E and a working portion 412, which is tapered in a shank to tip direction. The tip 413 can include a cutting surface, which is confluent the working surface 412 (for example, like the tip shown in FIGS. 22A-22D). Alternatively, the tip 413 can display a non cutting surface, which is confluent with the working portion 412 (for example, like the tip shown in FIG. 9C). The instrument includes an MxFD 417 and an MnFD 416. The shank 411 above the above the working portion 412 is essentially cylindrical exhibiting a slightly smaller diameter than the cutting surface at the MxFD. The shank here is similar to the one described in FIGS. 21A-21E. The instrument includes a modified or rolled edge portion 414, which is confluent with the cutting surface 412. This rolled edge feature is illustrated in FIGS. 9A-9D. A fitting, which is suitable for an engine driven motor with a hand-piece and chuck or a handle utilized for manual instrumentation, is attached to the shank at its most proximal end also similar to the fitting described in FIGS. 21A-21E.

As shown in FIGS. 25A-25E, four continuous flutes 420A, 420B, 420C and 420D are substantially concave grooves, which follow the circumference of the working surface 412 spiraling toward the leading tip 413 forming concentric circles, which may be equidistant or become increasingly tighter or more numerous as they approach the tip. The total number of flutes from MxFD to the MnFD should be no fewer than 16 but not greater than 24. Flutes 420A, 420B, 40C, and 420D each originate at the MxFD at various locations spaced around the circumference of the shank, more specifically at 90°, 100°, 70°, and 100° of separation, respectively. Each flute is continuous along the length of the cutting surface 412 to the leading tip 413.

Figure 25D:
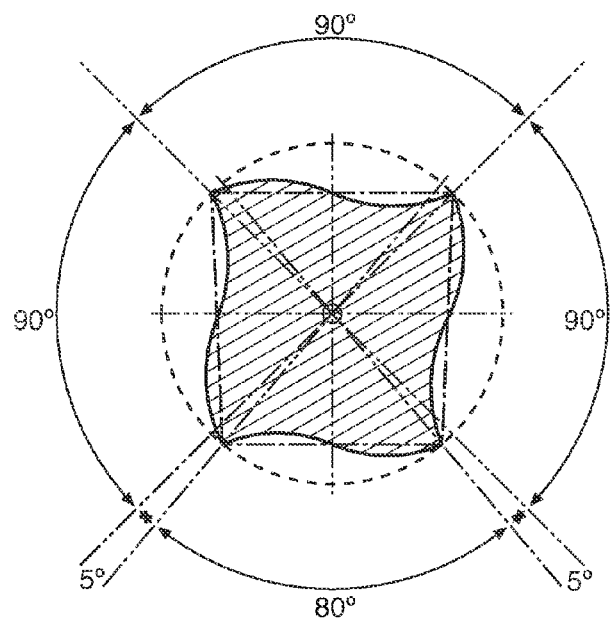
Figure 25E:
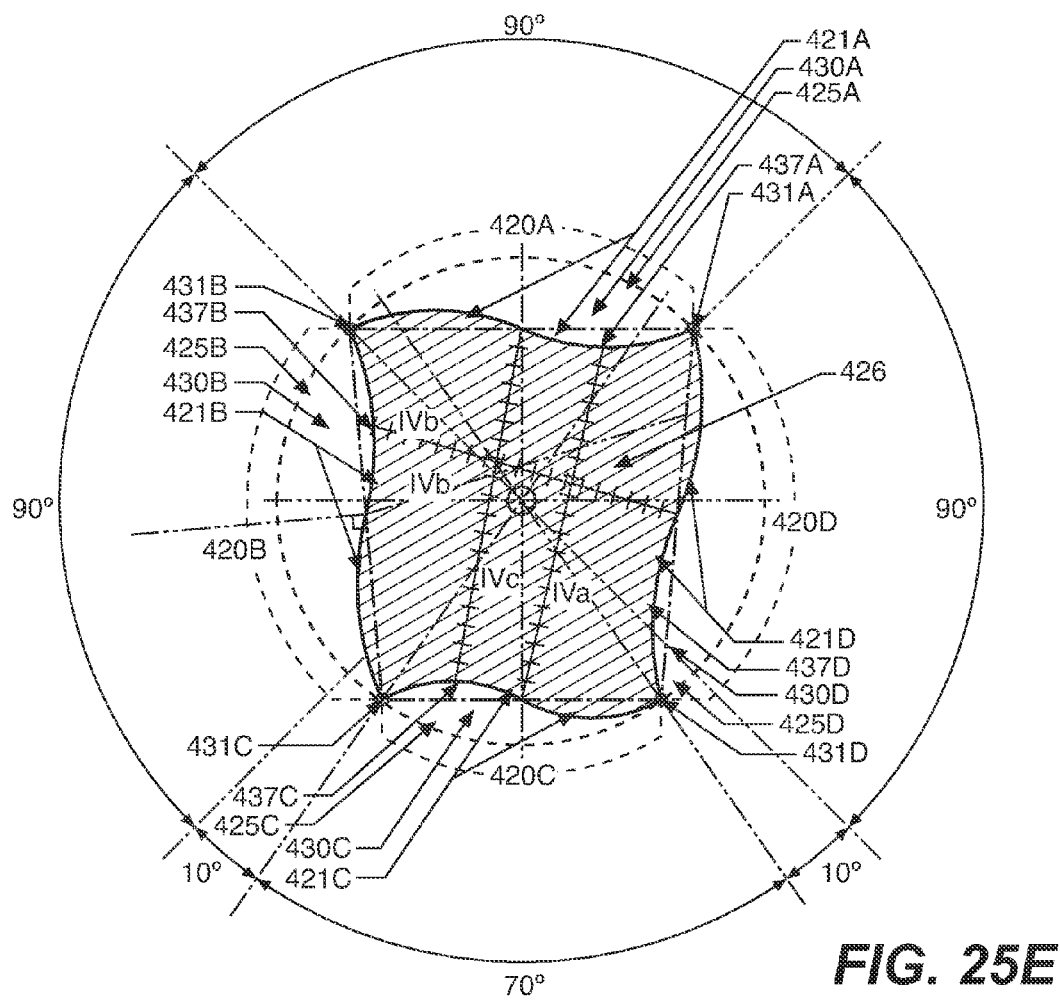

With reference to FIG. 25E, it can be seen that flutes 420A, 420B, 420C, and 420D have an S-shaped splines 421A, 421B, 421C, and 421D. The flutes 420A, 420B, 420C, and 420D form helical cutting edges 425A, 425B, 425C, and 425D at the periphery of the shank 411. As shown in FIG. 25E, a transverse cross-section is shown of the cutting portion 412. The flutes 420A, 420B, 420C, and 420D cooperate to form a web or core 426, which is essentially rectagonally shaped. The web or core is outlined by areas of radial clearance or cut outs created by the splines 421A, 421B, 421C, and 421D. These areas of clearance are designated by numerals 430A, 430B, 430C, and 430D. In transverse cross section of the shank, the splines 421A, 421B, 421C, and 421D of flutes 420A, 420B, 420C, and 420D form teardrop clearance areas of variable depth. Clearance areas 430A, 430B, 430C, and 430D are circumscribed by cutting edges 425A, 425B, 425C, and 425D, or the perimeter of the shank, and the splines 421A, 421B, 421C, and 421D.

As shown in FIG. 25E, it can be seen that splines 421A, 421B, 421C, and 421D intersect the periphery of the shank 411 at points 431A, 431B, 431C, and 431D, respectively. These intersections are at 90°, 100°, 70°, and 100° of separation, respectively, forming neutral or slightly positive rake angles. Lines drawn connecting points 331A, 331B, 331C, and 331D form a trapezoid. The difference in degrees between the longest spline and the shortest spline is 30°. Alternatively, as shown in FIG. 24E, points 331A, 331B, 331C, and 331D can intersect the periphery of the shank 311 at 80°, 100°, 80°, and 100° of separation, respectively. Lines drawn connecting the points 431A, 431B, 431C, and 431D also form a trapezoid. The outline of the trapezoid that is formed connecting points 431A, 431B, 431C, and 431D can vary. The difference in the number of degrees of separation between the longest spline and the short spline should not be less than 5° and not greater than 70°.

The splines 421A, 421B, 421C, and 421D are S-shaped and are individually symmetrical. The bisector of each spline divides the spline equally into convex and a concave segments which form the S-shaped curve. Alternate bisectors a, b, and c can be drawn from the center of each spline through the greatest concavity the opposite spline.

The greatest depth of each spline can be defined as segments of lines IVa, IVb, and IVc. These depths can vary and, furthermore, be calculated as a percentage of the length of lines IVa, IVb, and IVc. The greatest depth depths of spline 421A, indicated with demarcated line segments 437A, is 5% of the length of IVa. The greatest depths of splines 421B, 421C, and 421D can be similarly indicated by demarcated line segments 437B, 437C, and 437D (437D is not shown but is the same length as 437B). The greatest convexities of splines 421A, 421B, 421C, and 421D are mirror images of the greatest concavities of the same splines. The depth and height of each spline can vary; however, the cross sectional diameter of the core portion 426 should generally not be narrower than half or fifty percent of the cross sectional diameter of the shank of the instrument.

Figure 26:
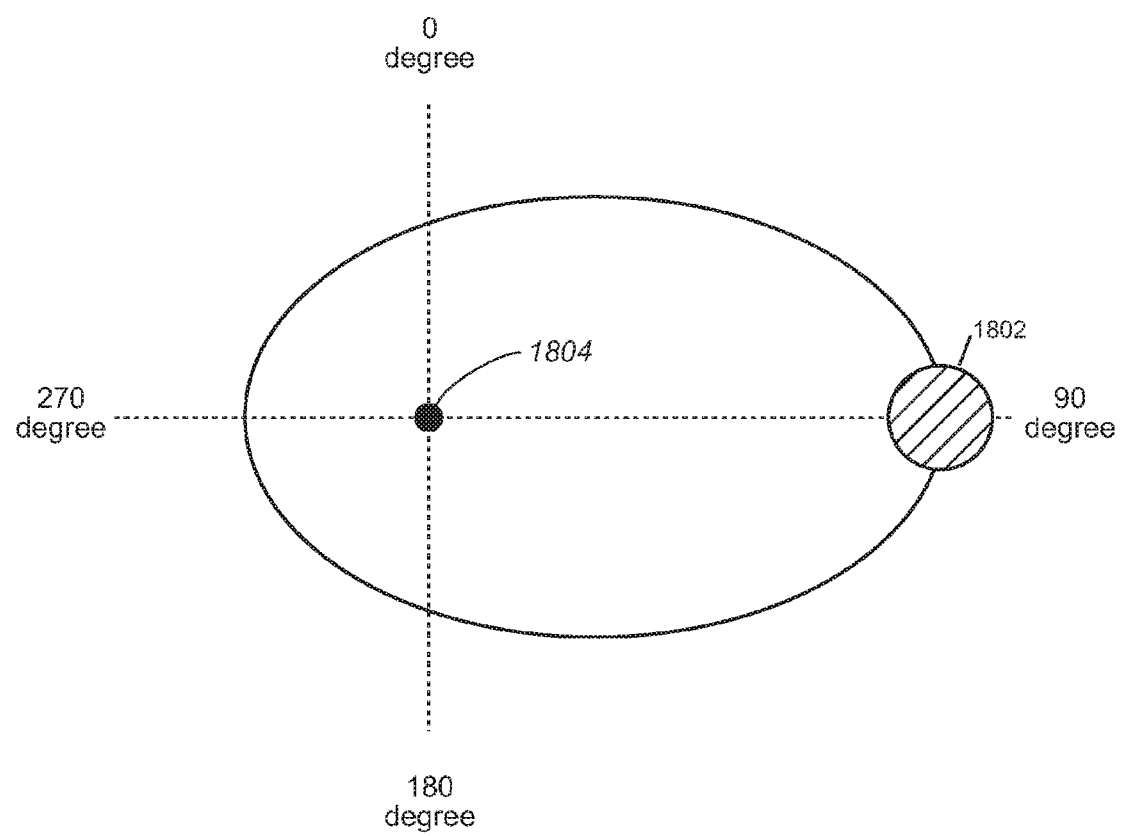
FIG. 26 illustrates swagger.

FIG. 26 provides a diagram of the part of an instrument 1802 that swings away from the axis of rotation different distances, depending on the angle of rotation, and thus swaggers in an un-equilateral manner. The extent to which the instrument 1802 swings away from the axis of rotation 1804 at a first angle of rotation, 90 degrees, is much greater than the extent to which the instrument 1802 swings away from the axis of rotation 1804 at a second angle of rotation, 270 degrees. In essence, the swing of the instrument is not symmetrical about the axis of rotation.

Referring to FIG. 27, a schematic of an instrument 2001 is shown that is capable of equilateral swagger. In one implementation, the profile of the instrument when viewed in transverse cross-section begins in its most proximal segment (near the shank end) as a completely symmetrical cross section. Gradually, the cross section becomes asymmetrical as it progresses distally (toward the tip end). A longitudinal view from the proximal end 2016 to the distal end 2036 would exhibit the symmetry change. At the proximal end 2016, a cross section of the instrument 2001 has points 2018 that are equidistant from a center of the instrument 2001 and overlap with an equilateral triangle 2020 that fits within a circle 2022 that would be formed by the points 2018 as the instrument 2001 rotates. At the distal end 2036, the cross section of the instrument 2001 has points 2032 that overlap with an isosceles triangle 2030 that fits within a circle 2038 formed by the points 2032 as the instrument 2001 rotates. The described change from a symmetrical to an asymmetrical cross-section can be gradual or progressive, but a rapid or progressive change is viewed to be more efficient. A gradual change can be a change that is similar over each segment, such as when the change between $D_2$ and $D_3$ is equal to the amount of change from $D_3$ to $D_4$ and from $D_4$ to $D_5$. A more progressive change may be that the amount of change changes geometrically or exponentially from the segment between $D_4$ and $D_5$ and the segment between $D_3$ and $D_4$. The change from symmetrical to asymmetrical can mean that the some of the flutes become closer together while others move further apart, one or more lands may extend further from the instrument than other of the lands, or geometry can change, such as when a triangular cross section with sides having the same length becomes a triangular cross section where at least one side is longer than another, or when a square cross section becomes trapezoidal.

Figures 28, 28A, 28B:
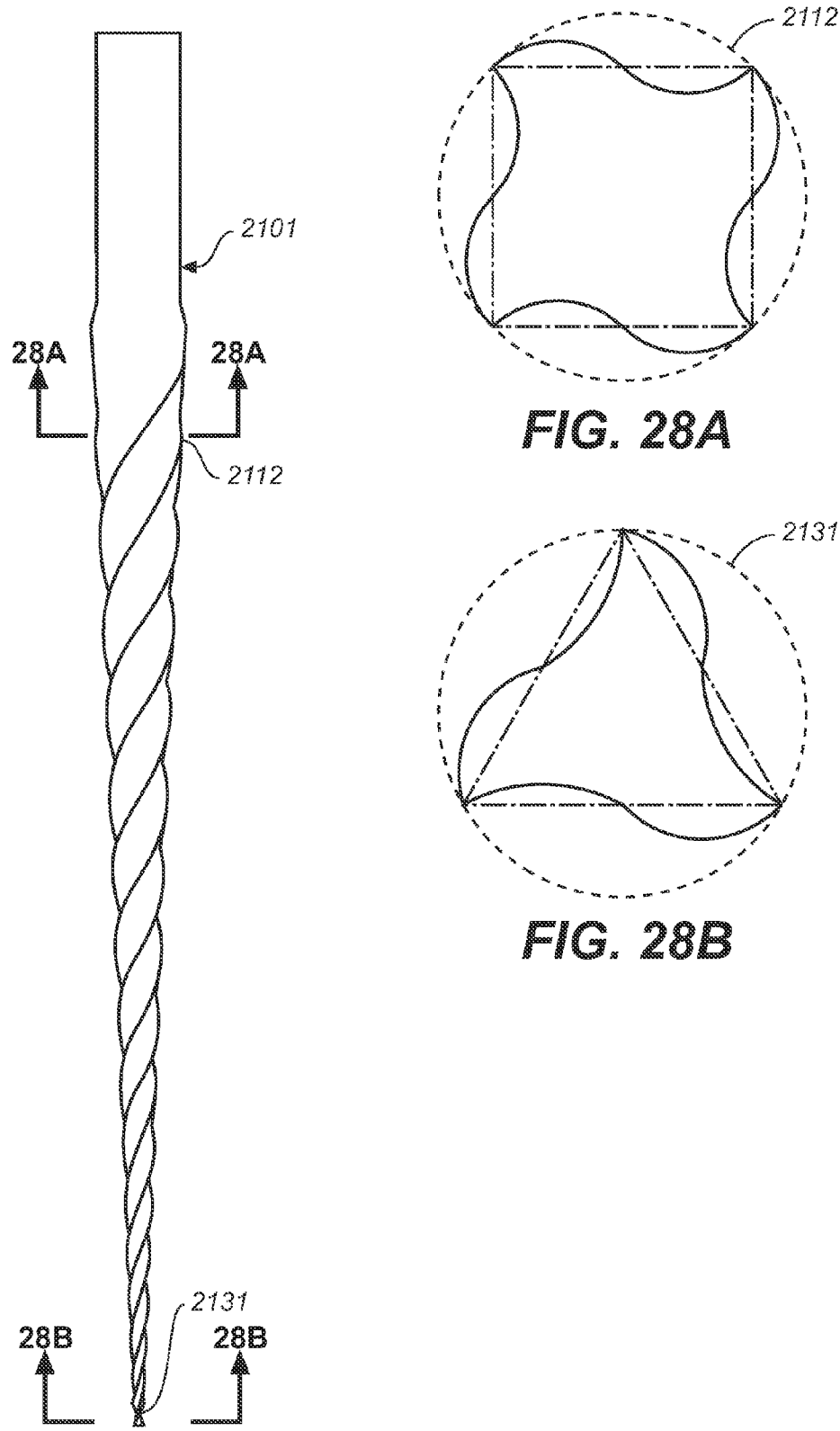

Yet another instrument that is capable of equilateral swagger can change both its symmetry and geometry along the length. The profile of the instrument when viewed in transverse cross-section begins in its most proximal segment as symmetrical, but takes on asymmetry and new geometry simultaneously. Referring to FIGS. 28, 28A and 28B, in one implementation, the cross section of the instrument 2101 begins, for example, as four-sided or rectangular and is symmetrical at a shank end 2112 and becomes three sided and asymmetric at a tip end 2131. Other examples are also possible, such as a three-sided polygon changing into a four, five or six-sided polygon, a four-sided polygon changing to a five or six-sided polygon, a five-sided polygon changing to a three, four, or six-sided polygon or a six-sided polygon changing to a three, four or five-sided polygon. The term polygon approximates the shape and is not meant to indicate that the sides necessarily are linear.

Figures 29C, 29D:
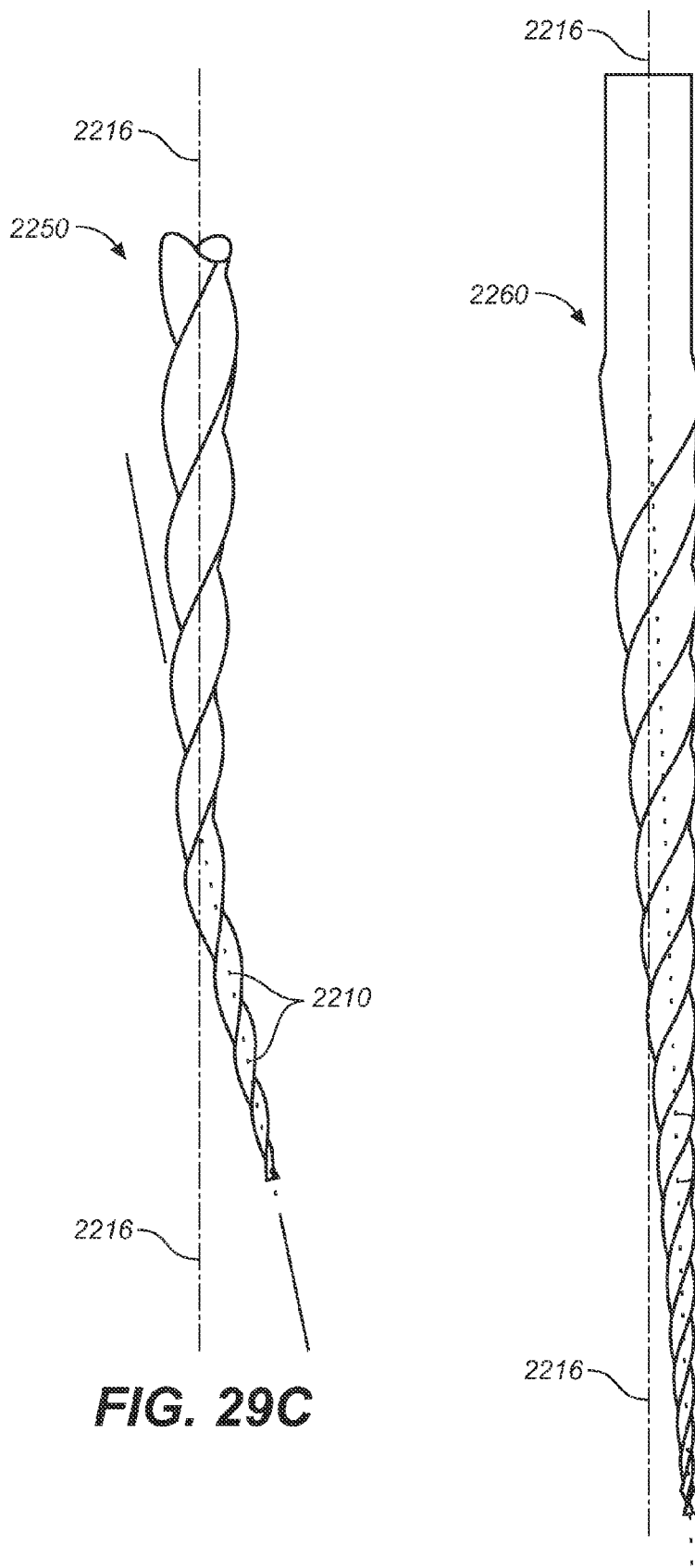

Referring to FIGS. 29, 29A, 29B, 29C, and 29D, a schematic of an instrument 2201 features a profile that has a canted longitudinal axis. That is, the centroids 2210 of the multiple cross sections of the canted portion 2242 of the instrument 2201 do not lie on the axis of rotation 2216. The instrument 2201 here can include a portion 2222 that has at least one cross-section (for example, near the shank end) that has a centroid 2210 that is on the axis of rotation 2216 and another portion 2242 that has at least one cross section (for example, near the tip end) that has a centroid that is off the axis of rotation 2216. The geometry can change or stay the same down the length of the instrument. The canted instrument can have a linear section, where at least the portion of the instrument having the working surfaces is linear, see instrument 2250 as shown in FIG. 29C, or the entire instrument can be linear, see instrument 2260 as shown in FIG. 29D.

Referring to FIGS. 30A and 30B, in some implementations, a portion of the canted instrument 2301, 2301' is curved. An instrument with a variable centroid, can have a gradual or progressive curve in the profile itself. That is, the centroids of the cross sections define a curve. The tip 2315, 2315' of the instrument 2301, 2301' can lie on or off of the axis of rotation 2320, respectively.

Any combination of the above described design features can be employed to create a hybrid design, which can be an enhancement of the basic designed or employed for a special case that may require customized instruments. For example, the working surfaces described in FIGS. 21-25 can be used with the instruments described in FIGS. 27-30B.

The changes in cross section geometry is not limited to those described above. The instrument can have, for example, a change in cross section geometry such that the cross sections of the instrument portion for cutting at the curved portion of the ECS are asymmetrical while the cross sections of the tip and end portions are symmetrical. Moreover, the change need not be gradual and can be accelerated, for example, at the instrument portion for cutting at the curved portion of the ECS.

Figure 31A:
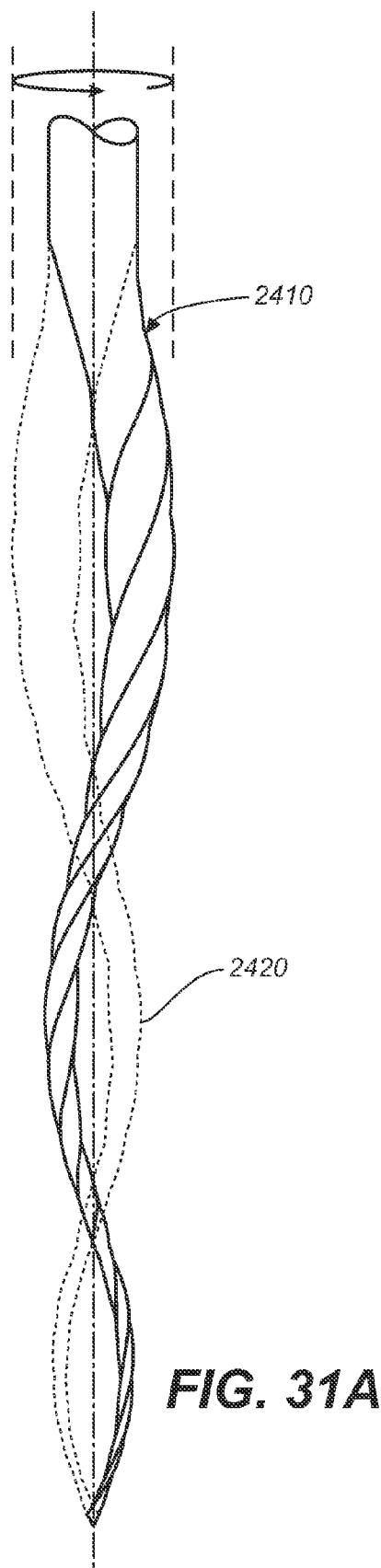
FIGS. 31A-31B are a schematics of an swaggering instrument during rotation.
Figure 31B:
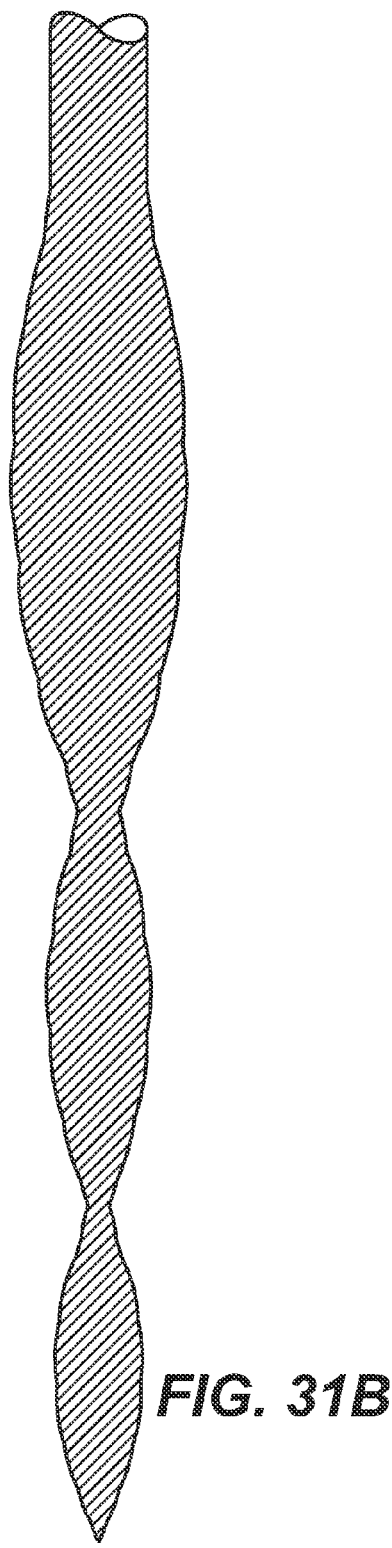

Referring to FIGS. 31A, 31B, as described herein, portions of the endodontic instrument capable of equilateral swagger will bend away from the axis of rotation when being used, such as with a motorized drill. In some implementations, the swaggering instrument 2410 will create a mechanical wave 2420, or multiples of a half of a mechanical wave. When viewed, the wave may appear to form helical waves that propagate up and down within the canal. The wave spirals in the x, y and z axes and moves in three dimensions. This can allow the instrument to undulate within the ECS to cut away material within the ECS. The swaggering can taper as it approaches non-swaggering portions of the instrument 2410. Additionally, changes in diameter and geometry can change the amount of swagger. FIG. 31A shows the instrument at two different locations at two different points in time while the instrument rotates. FIG. 31B shows the area covered by the instrument as it rotates. As the wave propagates, different portions of the instrument extend from the axis of rotation varying amounts (not shown) and may appear as a spiraling body to a human viewer when the instrument is rotating very fast.

Methods of Forming Instruments

The instruments described herein can be formed starting with a blank that is then shaped to achieved a desired result. Referring to FIGS. 32A, 32B, a blank 2510, such as a metal blank, can be shaped to have a substantially uniform geometry or cross section from a shank end 2514 to a tip end 2518. The geometry is asymmetrical down the length of the blank 2510. The center of mass is the same relative to the axis of rotation 2516 along the length of the blank 2510. As the flutes are formed, such as by milling, machining, cutting or grinding, the relative distances between the flutes can be changed or the depths can be changed to achieve the instrument described above with reference to FIG. 27.

Referring to FIGS. 33A, 33B, a blank 2520 is shaped to have a different geometry at the shank end 2524 than the tip end 2528. Here, at the shank end 2524, the blank 2520 has a rectangular or square cross section. At the tip end 2528, the blank 2520 takes on a triangular cross section. Between the triangular cross section and the rectangular cross section, the blank takes on a trapezoidal cross section. The blank 2520 has an axis of rotation 2526. The desired flute pattern can then be formed in the instrument. Such an instrument is described above with respect to FIG. 28.

Referring to FIGS. 34A, 34B, a blank 2530 is cut into a canted shape. At the shank end 2534, the blank 2530 has a center of mass or geometric center that is on a first axis 2540. Toward the tip end 2538, the blank 2530 has a center of mass or geometric center that is on a second axis 2542. The first access 2540 is parallel to the second access 2542, but the two do not overlap. If the instrument were cut perpendicular to either of the axes, the cross section of the instrument would be symmetrical. In some implementations, the blank is formed with a flexible metal, such as a memory metal and the shape is achieved by machining the blank 2530, rather than bending the blank. The instrument is then machined to form the desired cutting surfaces. Such a canted instrument formed from blank 2530 is described in FIG. 29D. In some implementations, the blank is symmetrical from the shank end 2534 to the tip end 2538.

Referring to FIGS. 35A, 35B, a blank 2550 is cut into a curved shape to form a curved instrument in a similar manner as described with respect to FIGS. 34A and 34B. The blank 2550 curves away from an axis 2552 that intersects a center of the blank 2550 at the shank end 2554.

An instrument that is bent into the desired configuration and then annealed (such as is often done with conventional dental tools, regardless of their geometry) may not exhibit the same type of swaggering, i.e., equilateral swaggering, as a similarly shaped instrument that has been shaped by cutting or machining Alternatives A number of implementations of the invention have been described. Nevertheless, it will be understood that various modifications may be made without departing from the spirit and scope of the invention. For example, in other implementations, similar instruments can include 5 or 6 flutes. The shanks and/or metal blanks from which these instruments can be fabricated and have slightly larger diameters providing enough material to facilitate the increased number of flutes. The flutes, therefore, would require fewer spirals per unit length. Instruments of increasing size, or diameter, become increasingly less flexible. Implementing more flutes and/or cutting the flutes deeper into the metal blanks during manufacture can facilitate compensation for the decrease in flexibility. In addition, wider and deeper spaces also provide greater opportunity to haul out debris from the apex to the coronal aspect of the tooth. Flexible materials other than Ni—Ti can be used to form the instrument. Also, although files and reamers are described in this document, an instrument having the features described herein can be applied to either type of device. Accordingly, other embodiments are contemplated.

What is claimed is:

1. An endodontic device, comprising:
a shank configured for attachment to a motor to rotate the endodontic device about an axis of rotation; and
a body extending from the shank by a length, the body being solid and having a tip end and a shank end and a working surface between the shank end and the tip end, the working surface including multiple cutting edges, at least a portion of the body with the working surface being tapered such that the tip end has a diameter that is less than a diameter of the shank end, the body comprising a plurality of transverse cross-sections, each transverse cross-section of the body having a center of mass and multiple sides, the body having a center of mass path defined by the centers of mass of all transverse cross-sections of the body, each side of the multiple sides intersecting two cutting edges of the multiple cutting edges, and wherein at least a portion of the center of mass path between the tip end and the shank end revolves around the axis of rotation.

2. The endodontic device of claim 1, wherein when the endodontic device is rotated by the motor, the endodontic device forms helical waves.

3. The endodontic device of claim 1, wherein the portion of the center of mass path that revolves around the axis of rotation extends from the tip end to the shank end.

4. The endodontic device of claim 1, wherein the plurality of transverse cross-sections includes a transverse cross-section that is triangular.

5. The endodontic device of claim 1, wherein the plurality of transverse cross-sections includes a transverse cross-section at the tip end that has a center of mass that coincides with the axis of rotation.

6. The endodontic device of claim 1, wherein the plurality of transverse cross-sections includes a transverse cross-section at the tip end that has a center of mass that is offset from the axis of rotation.

7. The endodontic device of claim 1, wherein the body is uniformly tapered from the shank end to the tip end.

8. The endodontic device of claim 1, wherein the plurality of transverse cross-sections includes a transverse cross-section that is a quadrilateral.

9. The endodontic device of claim 1, wherein the plurality of transverse cross-sections includes a transverse cross-section that is asymmetrical.

10. The endodontic device of claim 1, wherein the plurality of transverse cross-sections includes a first transverse cross-section and a second transverse cross-section, wherein the first transverse cross-section has a first geometry, and wherein the second transverse cross-section has a second geometry different from the first geometry.

11. The endodontic device of claim 10, wherein each transverse cross-section between the first transverse cross-section and the second transverse cross-section has a gradually changing geometry with respect to each other.

12. The endodontic device of claim 1, wherein the tip end of the body is smooth.

13. The endodontic device of claim 1, wherein the body comprises nickel-titanium.

14. The endodontic device of claim 1, wherein the plurality of transverse cross-sections includes a first transverse cross-section and a second transverse cross-section, wherein a center of mass of the first transverse cross-section is spaced apart from the axis of rotation by a first distance, wherein a center of mass of the second transverse cross-section is spaced apart from the axis of rotation by a second distance, and wherein the first distance is greater than the second distance.

15. The endodontic device of claim 1, wherein each transverse cross-section of the body is defined by a polygonal shape.

16. The endodontic device of claim 15, wherein a ratio of lengths of sides of the polygonal shape remain constant along the length of the body.

17. The endodontic device of claim 15, wherein a ratio of lengths of sides of the polygonal shape vary along the length of the body.

18. The endodontic device of claim 1, wherein the tip end is on the axis of rotation.

19. The endodontic device of claim 1, wherein when the endodontic device is rotated the body forms at least one half-wave of a sinusoid.

20. The endodontic device of claim 19, wherein when the endodontic device is rotated the body forms a plurality of half-waves of a sinusoid.

* * * * *